United States Patent
Salituro et al.

(10) Patent No.: US 9,221,792 B2
(45) Date of Patent: Dec. 29, 2015

(54) N-(4-(AZETIDINE-1-CARBONYL)PHENYL)-(HETERO-) ARYLSULFONAMIDE DERIVATIVES AS PYRUVATE KINASE M2 (PMK2) MODULATORS

(75) Inventors: Francesco G. Salituro, Marlborough, MA (US); Jeffrey O. Saunders, Lincoln, MA (US); Shunqi Yan, Irvine, CA (US)

(73) Assignee: AGIOS PHARMACEUTICALS, INC, Cambridge, MA (US)

( * ) Notice: Subject to any disclaimer, the term of this patent is extended or adjusted under 35 U.S.C. 154(b) by 91 days.

(21) Appl. No.: 13/994,398

(22) PCT Filed: Dec. 16, 2011

(86) PCT No.: PCT/US2011/065633
§ 371 (c)(1),
(2), (4) Date: Oct. 28, 2013

(87) PCT Pub. No.: WO2012/083246
PCT Pub. Date: Jun. 21, 2012

(65) Prior Publication Data
US 2014/0073625 A1   Mar. 13, 2014

Related U.S. Application Data

(60) Provisional application No. 61/424,395, filed on Dec. 17, 2010.

(51) Int. Cl.
| | | |
|---|---|---|
| A61K 31/397 | (2006.01) | |
| A61K 31/00 | (2006.01) | |
| C07D 205/00 | (2006.01) | |
| C07D 215/36 | (2006.01) | |
| C07D 401/12 | (2006.01) | |
| C07D 401/14 | (2006.01) | |
| A61K 31/4709 | (2006.01) | |

(52) U.S. Cl.
CPC ............ C07D 401/12 (2013.01); C07D 215/36 (2013.01); C07D 401/14 (2013.01); A61K 31/4709 (2013.01)

(58) Field of Classification Search
CPC .. C07D 401/12; C07D 401/10; C07D 401/14; A61K 31/4709
USPC ........... 514/210.17, 210.18, 210.02; 546/172; 548/952, 953
See application file for complete search history.

(56) References Cited

U.S. PATENT DOCUMENTS

| | | |
|---|---|---|
| 3,046,122 A | 7/1962 | Oskar Siis et al. |
| 3,097,210 A | 7/1963 | Bicking |
| 3,998,828 A | 12/1976 | Wiedermann |
| 4,235,871 A | 11/1980 | Papahadjopoulos et al. |
| 4,315,940 A | 2/1982 | Hitzel et al. |
| 4,474,599 A | 10/1984 | Rogers et al. |
| 4,501,728 A | 2/1985 | Geho et al. |
| 4,591,548 A | 5/1986 | Delprato |
| 4,593,102 A | 6/1986 | Shanklin, Jr. |
| 4,775,762 A | 10/1988 | Knox et al. |
| 4,837,028 A | 6/1989 | Allen |
| 4,849,424 A | 7/1989 | Ikeda et al. |
| 4,881,965 A | 11/1989 | Yamamoto et al. |
| 4,889,553 A | 12/1989 | Rowson et al. |
| 4,959,094 A | 9/1990 | Wegner et al. |
| 5,019,369 A | 5/1991 | Presant et al. |
| 5,122,530 A | 6/1992 | Tomioka et al. |
| 5,180,732 A | 1/1993 | Tomioka et al. |
| 5,220,028 A | 6/1993 | Iwasawa et al. |
| 5,252,590 A | 10/1993 | Tomioka et al. |
| 5,556,866 A | 9/1996 | Aga et al. |
| 5,834,485 A | 11/1998 | Dyke et al. |
| 5,962,490 A | 10/1999 | Chan et al. |
| 5,965,559 A | 10/1999 | Faull et al. |
| 5,965,569 A | 10/1999 | Camps Garcia et al. |
| 6,020,357 A | 2/2000 | Pinto et al. |
| 6,106,849 A | 8/2000 | Malkan et al. |
| 6,150,356 A | 11/2000 | Lloyd et al. |
| 6,172,005 B1 | 1/2001 | Selby |
| 6,265,588 B1 | 7/2001 | Mullner et al. |

(Continued)

FOREIGN PATENT DOCUMENTS

| | | |
|---|---|---|
| CA | 2235621 A1 | 5/1997 |
| CN | 101296909 A | 10/2008 |

(Continued)

OTHER PUBLICATIONS

International Search Report for PCT/US2010/059778 dated Mar. 17, 2011.

(Continued)

*Primary Examiner* — Shengjun Wang
(74) *Attorney, Agent, or Firm* — Lando & Anastasi LLP

(57) ABSTRACT

Compounds of general Formula (I), and compositions comprising compounds of general formula I that modulate pyruvate kinase M2 (PKM2) are described herein. Also described herein are methods of using the compounds that modulate PKM2 in the treatment of cancer.

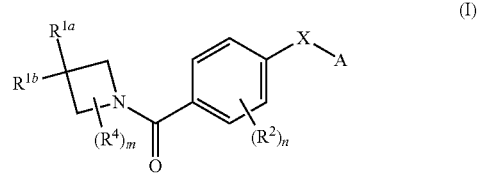

14 Claims, No Drawings

(56) References Cited

U.S. PATENT DOCUMENTS

| | | |
|---|---|---|
| 6,313,127 B1 | 11/2001 | Waterson et al. |
| 6,492,368 B1 | 12/2002 | Dorsch et al. |
| 6,511,977 B1 | 1/2003 | Lloyd et al. |
| 6,818,631 B1 | 11/2004 | Nakagawa et al. |
| 7,288,554 B2 | 10/2007 | Finkelstein et al. |
| 7,524,848 B2 | 4/2009 | Powers et al. |
| 7,572,913 B2 | 8/2009 | McKerracher et al. |
| 7,615,553 B2 | 11/2009 | Van Emelen et al. |
| 7,863,444 B2 | 1/2011 | Calderwood et al. |
| 8,058,313 B2 | 11/2011 | Reddy et al. |
| 8,642,660 B2 | 2/2014 | Goldfarb |
| 8,742,119 B2 | 6/2014 | Salituro et al. |
| 2003/0082877 A1 | 5/2003 | Ootsuka et al. |
| 2003/0095958 A1 | 5/2003 | Bhisetti et al. |
| 2003/0106381 A1 | 6/2003 | Krouth et al. |
| 2003/0158232 A1 | 8/2003 | Cheng et al. |
| 2003/0187001 A1 | 10/2003 | Calderwood et al. |
| 2003/0207882 A1 | 11/2003 | Stocker et al. |
| 2004/0048283 A1 | 3/2004 | Pau et al. |
| 2004/0152648 A1 | 8/2004 | Ullrich et al. |
| 2004/0198979 A1 | 10/2004 | Dhanak et al. |
| 2004/0235755 A1 | 11/2004 | Eigenbrodt et al. |
| 2005/0176675 A1 | 8/2005 | Gorny |
| 2007/0032418 A1 | 2/2007 | Shapiro et al. |
| 2007/0127505 A1 | 6/2007 | Laurila et al. |
| 2007/0280918 A1 | 12/2007 | Schwartz et al. |
| 2008/0004269 A1 | 1/2008 | Xu et al. |
| 2008/0021116 A1 | 1/2008 | Ullrich et al. |
| 2008/0044833 A1 | 2/2008 | Connors |
| 2008/0051414 A1 | 2/2008 | Hurley et al. |
| 2009/0048227 A1 | 2/2009 | Chakravarty et al. |
| 2009/0054453 A1 | 2/2009 | Alcaraz et al. |
| 2009/0163545 A1 | 6/2009 | Goldfarb |
| 2009/0247499 A1 | 10/2009 | Fletcher et al. |
| 2009/0270454 A1 | 10/2009 | Weingarten et al. |
| 2010/0105657 A1 | 4/2010 | Nordvall et al. |
| 2010/0179150 A1 | 7/2010 | Basarab et al. |
| 2010/0331307 A1 | 12/2010 | Salituro et al. |
| 2011/0046083 A1 | 2/2011 | Cantley et al. |
| 2011/0224252 A1 | 9/2011 | Dumeunier et al. |
| 2011/0312931 A1 | 12/2011 | Cioffi et al. |

FOREIGN PATENT DOCUMENTS

| | | |
|---|---|---|
| DE | 3813886 A1 | 11/1989 |
| DE | 19841985 A1 | 3/2000 |
| EP | 0246749 A2 | 11/1987 |
| EP | 0628551 A1 | 12/1994 |
| EP | 1586558 A2 | 10/2005 |
| FR | 2735127 A1 | 12/1996 |
| GB | 1274436 A | 5/1972 |
| IT | 1176770 B | 8/1987 |
| JP | S61129129 A | 6/1986 |
| JP | 06-025177 | 2/1994 |
| JP | H07165708 A | 6/1995 |
| JP | 2002-193710 A | 7/2002 |
| JP | 2007/238458 A | 9/2007 |
| JP | 2008514590 A | 5/2008 |
| WO | 8501289 A1 | 3/1985 |
| WO | 9211761 A1 | 7/1992 |
| WO | 93/13072 A1 | 7/1993 |
| WO | 9630343 A1 | 10/1996 |
| WO | 97/28128 A1 | 8/1997 |
| WO | 97/28129 A1 | 8/1997 |
| WO | 97/28141 A1 | 8/1997 |
| WO | 9744322 A1 | 11/1997 |
| WO | 98/03350 A1 | 1/1998 |
| WO | 99/16751 A1 | 4/1999 |
| WO | 9916751 A1 | 4/1999 |
| WO | 0017202 A1 | 3/2000 |
| WO | 00/53596 A2 | 9/2000 |
| WO | 01/07440 A1 | 2/2001 |
| WO | 0119788 A2 | 3/2001 |
| WO | 0119798 A2 | 3/2001 |
| WO | 0164642 A2 | 9/2001 |
| WO | 0164643 A2 | 9/2001 |
| WO | 02/072077 A2 | 9/2002 |
| WO | 02/095063 A1 | 11/2002 |
| WO | 02100822 A1 | 12/2002 |
| WO | 03022277 A1 | 3/2003 |
| WO | 03037252 A2 | 5/2003 |
| WO | 03/062235 A1 | 7/2003 |
| WO | 03/073999 A2 | 9/2003 |
| WO | 03/076422 A1 | 9/2003 |
| WO | 03093297 A2 | 11/2003 |
| WO | 2004/004730 A2 | 1/2004 |
| WO | 2004014851 A2 | 2/2004 |
| WO | 2004/037251 A1 | 5/2004 |
| WO | 2004/073619 A2 | 9/2004 |
| WO | 2004/074438 A2 | 9/2004 |
| WO | 2004089470 A2 | 10/2004 |
| WO | 2004/110375 A2 | 12/2004 |
| WO | 2005/072642 A1 | 8/2005 |
| WO | 2005/117591 A2 | 12/2005 |
| WO | 2005120474 A2 | 12/2005 |
| WO | 2006/004195 A1 | 1/2006 |
| WO | 2006/016062 A1 | 2/2006 |
| WO | 2006033628 A1 | 3/2006 |
| WO | 2006034341 A2 | 3/2006 |
| WO | 2006-038594 A1 | 4/2006 |
| WO | 2006043950 A1 | 4/2006 |
| WO | 2006052190 A1 | 5/2006 |
| WO | 2006070198 A1 | 7/2006 |
| WO | 2006/122546 A1 | 11/2006 |
| WO | 2006117762 A2 | 11/2006 |
| WO | 2007003934 A2 | 1/2007 |
| WO | 2007023186 A1 | 3/2007 |
| WO | 2007/127505 A2 | 11/2007 |
| WO | 2008/019139 A2 | 2/2008 |
| WO | 2008024284 A2 | 2/2008 |
| WO | 2008/026658 A1 | 3/2008 |
| WO | 2008047198 A1 | 4/2008 |
| WO | 2008/050168 A1 | 5/2008 |
| WO | 2008052190 A2 | 5/2008 |
| WO | 2008073670 A2 | 6/2008 |
| WO | 2009012430 A1 | 1/2009 |
| WO | 2009013126 A1 | 1/2009 |
| WO | 2009/025781 A1 | 2/2009 |
| WO | 2009/053102 A1 | 4/2009 |
| WO | 2009086303 A2 | 7/2009 |
| WO | 2010/042867 A2 | 4/2010 |
| WO | 2010105243 A1 | 9/2010 |
| WO | 2010118063 A2 | 10/2010 |
| WO | 2010/129596 A1 | 11/2010 |
| WO | 2010130638 A1 | 11/2010 |
| WO | 2011002817 A1 | 1/2011 |
| WO | 2011032169 A1 | 3/2011 |
| WO | 2011047432 A1 | 4/2011 |
| WO | 2011/072174 A1 | 6/2011 |
| WO | 2011137089 A1 | 11/2011 |
| WO | 2012/092442 A1 | 7/2012 |

OTHER PUBLICATIONS

International Search Report, Application No. PCT/US2009/060237, dated Jun. 16, 2010.
International Search Report, Application No. PCT/US2011/033852, dated Aug. 3, 2011.
Jiang et al., "Evaluation of thieno[3,2-b]pyrrole[3,2-d]pyridazinones as activators of the tumor cell specific M2 isoform of pyruvate kinase." Bioorg. Med. Chem. Lett., 20 (11), 3387-3393 (2010).
Joshi et al., "Age-related faecal calprotectin, lactoferrin and tumour M2-PK concentrations in healthy volunteers." Ann Clin Biochem.;47(Pt 3):259-63 (2010).
Jurica et al., "The Allosteric Regulation of Pyruvate Kinase by Fructose-1,6-Bisphosphate," Structure 6: 195-210 (1998).
Kao et al., "A Small-Molecule Inhibitor of the Ribonucleolytic Activity of Human Angiogenin That Possesses Antitumor Activity," Proc. Natl. Acad. Sci. USA, 99(15): 10066-10071 (2002).
Kharalkar et al., "Identification of Novel Allosteric Regulators of Human-Erythrocyte Pyruvate Kinase," Chem Biodivers. 4: 2603-2617 (2007).

(56) References Cited

OTHER PUBLICATIONS

Klapars et al., "A General and Efficient Copper Catalyst for the Amidation of Aryl Halides and the N-Arylation of Nitrogen Heterocycles," J. Am. Chem. Soc., 123 (31), 7727-7729 (2001).
Kumar et al., "In vivo factors influencing tumour M2-pyruvate kinase level in human pancreatic cancer cell lines." Tumour Biol.;31(2):69-77 (2010).
Kung et al. "Small Molecule Activation of PKM2 in Cancer Cells Induces Serine Auxotrophy" Chemistry & Biology, 19, 1187-1198, Sep. 21, 2012.
Lee et al., "An Efficient Synthesis of 2,8-Diazabicyclo[4.3.0]-Nonane Derivatives via Intramolecular Cyclization Reaction," Synth. Comm., 25 (23), 3741-3746 (1995).
Lee, "Consolidation Effect of Phenylalanine-administration of Antitumor Activity of A 5 Fluorouracil," Med. J. Kagoshima Univ. 37(3-4): 285-308 (1985).
Lee, et al., "Pyruvate kinase isozyme type M2 (PKM2) interacts and cooperates with Oct-4 in regulating transcription" International J. Biochem. & Cell Biol., vol. 40, # 5,2008, 1043-1054.
Li et al., "Quantitative proteome analysis of multidrug resistance in human ovarian cancer cell line." J Cell Biochem.;109(4):625-33 (2010).
Li et al., "Screening and identification of interactive proteins of SH2D4A." Yi Chuan.;32(7):712-8 (2010). (Abstract Only).
Mass, R. D., "The HER receptor family: a rich target for therapeutic development", Int. J. Radiation Oncology Bio. Phys. vol. 58(3): 932-940, 2004.
Oeda, "On some 2,5-Dialikl-piperazines," Bull. Chem. Soc., 13, 465-470 (1938).
Park, "Prevention of type 2 diabetes mellitus from the viewpoint of genetics." Diabetes Research and Clinical Practice 2004; 66S: S33-S35.
Paudler et al., "3,7-Disubstituted octahydro-1,5-diazocines. Their conversion into tetrahydro-1,5-diazocines and into ring-contracted products," J. Org. Chern., 32 (8), 2425-2430 (1967).
Pollard et al., "Some Amides of Piperazines," J. Am. Chem. Soc., 75 (2), 491 (1953).
Pujol, et. al., "Is there a case for cisplatin in the treatment of smallcell lung cancer? A meta-analysis of randomized trials of a cisplatin-containing regimen versus a regimen without this alkylating agent" British Journal of Cancer, Cancer Research Campaign, vol. 83, issue 1, pp. 8-15, 2000.
Remington's, "Structure Activity Relationship and Drug Design," Pharmaceutical Sciences, pp. 420-425p. 420-425, 1980.
Rich, et. al., "Development of novel targeted therapies in the treatment of malignant glioma" Nature Rev. Drug Disc., Nature Publishing Group, vol. 3, pp. 430-446, 2004.
Root et al., "Genome-Scale Loss-of-Function Screening with a Lentiviral RNAi Library," Nat Methods 3: 715-719 (2006).
Ruan et al., "HSP60, a protein downregulated by IGFBP7 in colorectal carcinoma." J Exp Clin Cancer Res.;29:41 (2010).
Sabatine et al., "Metabolomic Identification of Novel Biomarkers of Myocardial Ischemia," Circulation 112: 3868-3875 (2005).
Schneider, et. al., "Tumor M2-pyruvate kinase in the follow-up of inoperable lung cancer patients: a pilot study." Cancer Letters, Elsevier, vol. 193, pp. 91-98, 2003.
Schroth et al., "RingschluBreaktion von Diacetylen mit Diaminen: Eine Ciniache von 2,3-Dihydro-1,4-diazepinen," Zeitschritt Fur Chemie., 6 (4), 143 (1969).
Seibel et al., "Synthesis and evaluation of B-lactams (piperazones) as elastase inhibitors," Bioorg. Med. Chern. Ltrs., 13 (3),387-389 (2003).
Shi, et al., "Silencing of pkm2 increases the efficacy of docetaxel in human lung cancer xenografts in mice." Cancer Science, vol. 101, # 6, 1447-1453, Jun. 2010.
Stewart et al., "Piperazines. I. Derivatives of Piperazine-1-Carboxylic and -1,4-Dicarboxylic Acid,", J. Org. Chern., 18 (1),1478-1483 (1953).

STN File CA, Registry No. 1023444-33-8, entered STN on May 29, 2008, Chemical Abstracts Index Name "Benzenesulfonamide, 34[[4-(1,3-benzodioxol-5-ylmethyl))-1-piperazinyl]carbonyl]N-(4-butylphenyl)-4-methyl-".
STN File CA, Registry No. 1090629-29-0, entered STN on Dec. 28, 2008, Chemical Abstracts Index Name "Benzenesulfonamide, 34[[4-[(2,5-dimethoxyphenyl)methyl]-1-piperazinyl]carbonyl]N-(4-methoxyphenyl)-4-methyl-".
STN File CA, Registry No. 713505-78-3, entered STN on Jul. 21, 2004, Chemical Abstracts Index Name "1-Piperazinecarboxylic acid, 4-[4-methyl-3-[(phenylamino)sulfonyl]benzoyl]-, ethyl ester".
STN File CA, Registry No. 847757-57-7, entered STN on Apr. 1, 2005, Chemical Abstracts Index Name "Benzenesulfonamide, 3[[4-(1,3-benzodioxol-5-ylmethyl)-1-piperazinyl]carbonyl]-N-(4-ethoxyphenyl)-N,4-dimethyl-" or "Piperazine, 1-(1,3-benzodioxol-5-ylmethyl)-4-[5-[[(4-ethoxyphenyl)methylamino]sulfonyl]-2-methylbenzoyl]-".
Supplemental EP Search Report & Written Opinion for EP 10 79 4667 dated Jan. 15, 2013.
Supplementary Search Report for EP10794668 Mailed Oct. 18, 2012.
Surh, "Cancer Chemoprevention with Dietary Phytochemicals", Nature Reviews Cancer, Nature Publishing Group, vol. 3, p. 768-780, 2003.
Szoka et al., "Comparative properties and methods of preparation of lipid vesicles (liposomes)," Ann. Rev. Biophys. Bioeng., 9, 467-508 (1980).
Tawaka, et al., Caplus an 1998:794998.
Uozumi et al., "Catalytic asymmetric construction of morpholines and piperazines by palladium-catalyzed tandem allylic substitution reactions," J. Org. Chem., 58 (24),6826-6832 (1993).
Vander Heiden et al., "Growth Factors Can Influence Cell Growth and Survival Through Effects on Glucose Metabolism," Mol Cell Bioi. 21: 5899-5912 (2001).
Vander Heiden et al., "Identification of Small Molecule Inhibitors of Pyruvate Kinase M2," Biochemical Pharmacology. 79(8): 1118-1124 (2010).
VanElemen et al, Caplus am 2003:737742.
Villen et al., "Large-Scale Phosphorylation Analysis of Mouse Liver," Proc Nat! Acad Sci USA 104: 1488-1493 (2007).
Walsh et al. "2-oxo-N-aryl-1,2,3,4-tetrahydroquinoline-6-sulfonamides as activators of the tumor cell specific M2 isoform of pyruvate kinase" Bioorg Med Chem Lett. Nov. 1, 2011; 21(21): 6322-6327.
Web posting, Pyruvate kinase M2 isozyme (PKM2), SciBX 5(42), Published online Oct. 25 2012, Abstract only.
Written Opinion of the International Searching Authority for PCT/US2008/009828, dated Dec. 5, 2008.
Yamada and Noguchi, "Nutrient and Hormonal Regulation of Pyruvate Kinase Gene Expression," Biochem J. 337: 1-11 (1999).
Adveenko, et al., "Thiocyanation of N-arylsulfonyl-, N-aroyl-, and N-[(N-arylsulfonyl)benzimidoyl]-1,4- benzoquinone imines" Russian Journal of Organic Chemistry, vol. 45, No. 3 (2009), 408-416.
Baxter I et al: "Preparation and some reactions of 6-arylsulphonimidobenzoxazol-2(3H)-one" Journal of the Chemical Society, Section C: Organic Chemistry, Chemical Society. Letchworth, GB LNKD-DOI:10.1039/J39700000850, Jan. 1, 1970, pp. 850-853.
Behun et al., "The Chemistry of Pyrazine and Its Derivatives. IV. The Alkylation and Arylation of Methylpyrazine," J Org. Chern., 26 (9),3379-3382 (1961).
Benesch et al., "The clinicopathological and prognostic relevance of pyruvate kinase M2 and pAkt expression in breast cancer." Anticancer Res.;30(5):1689-94 (2010).
Berger, et. al., "Treatment of Pancreatic Cancer: Challenge of the Facts" World J. Surg., Societe Internationale de Chirurgie, vol. 27, pp. 1075-1083, 2003.
Bonuccelli et al., "The reverse Warburg effect: Glycolysis inhibitors prevent the tumor promoting effects of caveolin-1 deficient cancer associated fibroblasts." Cell Cycle.;9(10) (2010).
Boxer, et al., "Evaluation of Substituted N,N?-Diarylsulfonamides as Activators of the Tumor Cell Specific M2 Isoform of Pyruvate Kinase", J Med Chem. Feb. 11, 2010; 53(3): 1048.

(56) References Cited

OTHER PUBLICATIONS

Boxer, et al., "Identification of activators for the M2 isoform of human pyruvate kinase Version 3", Sep. 2009, Probe Reports from the NIH Molecular Libraries Program [Internet]. Bethesda (MD): National Center for Biotechnology Information (US).
Budinger et al., "Cellular Energy Utilization and Supply During Hypoxia in Embryonic Cardiac Myocytes," Am J Physiol. 270: L44-53 (1996).
Buschow et al., "MHC class II-associated proteins in B-cell exosomes and potential functional implications for exosome biogenesis." Immunol Cell Biol. (2010).
Cecil Textbook of Medicine, edited by Bennet, J.C., and Plum F., 20th edition, vol. 1, 1004-1010, 1996.
Chabner, et. al., "Chemotherapy and the war on cancer", Nature Rev. Cancer, Nature Publishing Group, vol. 5, pp. 65-72, 2005.
Chan et al., "Synthesis and characterization of poly(amide sulfonamide)s (PASAs)," J Polymer. Sci., 33 (15), 2525-2531 (1995).
Christofk et al., "Pyruvate Kinase M2 is a Phosphotyrosine-Binding Protein," Nature 452: 181-186 (2008).
Christofk et al. , "The M2 Splice Isoform of Pyruvate Kinase is Important for Cancer Metabolism and Tumour Growth," Nature 452: 230-233 (2008).
Clement, et. al., "Production of Intracellular Superoxide Mediates Dithiothreitol-Dependent Inhibition of Apoptotic Cell Death" Antioxidants and Redox Signaling, Mary Ann Liebert, vol. 7, issues 3-4, pp. 456-464, 2005.
Cohen et al., "The development and therapeutic potential of protein kinase inhibitors", Current Opinion in Chemical Biology, 3,459-465, 1999.
Cuzick, et. al., "Overview of the main outcomes in breast-cancer prevention trials" The Lancet, The Lancet Publishing Group, vol. 361, pp. 296-300, 2003.
Database Chemcats, Chemical Abstracts Service, Columbus, OH, US "Bionet Screening Compounds" Key Organics Ltd., Camelford, Cornwall (2001).
Dermer et al., "Another Anniversary for the War on Cancer", Bio/Technology, 1994, 12:320.
Dombrauckas, et al., Structural Basis for Tumor Pyruvate Kinasa M2 Allosteric Regulation and Catalysis, Biochemistry, vol. 44, p. 9717-9429 (2005).
Eigenbrodt et al., "Double Role for Pyruvate Kinase Type M2 in the Expansion of Phosphometabolite Pools Found in Tumor Cells," Crit Rev Oncog. 3: 91-115 (1992). (Abstract only).
Engelman et al., "Allelic Dilution Obscures Detection of a Biologically Significant Resistance Mutation in EGFR-Amplified Lung Cancer," J Clin Invest 116: 2695-2706 (2006).
Eswaran et al., "Crystal Structures and Inhibitor Identification for PTPN5, PTPRR and PTPN7: A Family of Human MApk-Specific Protein Tyrosine Phosphatases," Biochem J. 395: 483-491 (2006).
Extended European Search Report (European Application No. 07836571.5), Dated Sep. 29, 2010.
Fabbro et al. "Protein kinases as targets for anticancer agents: from inhibitors to useful drugs." Pharmacology & Therapeutics 93, 79-98, 2002.
Freshney et al.,Culture of Animal Cells, A Manual of Basic Technique, Alan R. Liss, Inc., 1983, New York, p. 4.
Friedman et al., "Leptin and the regulation of body weight in mammals" Nature. vol. 395, 1996.
Furuya et al., Inactivation of the 3-phosphoglycerate dehydrogenase gene in mice: changes in gene expression and associated regulatory networks resulting from serine deficiency. Funct Integr Genomics (2008) 8:235-249.
Ge et al. "Anaplasma phagocytophilum inhibits human neutrophil apoptosis via upregulation of bfl-1, maintenance of mitochondrial membrane potential and prevention of caspase 3 activation." Cellular Microbiology, 2005, 7(1 ), 29-38.
Golub et al., "Molecular Classification of Cancer: Class Discovery and Class Prediction by Gene Expression Monitoring", Science, 286, 531-537, 1999.

Gupta et al., "Dominant negative mutations affect oligomerisation of human pyruvate kinase M2 isozyme and promote cellular growth and polyploidy." J Biol Chem. (2010).
Hitosugi, et al., "Tyrosine Phosphorylation Inhibits PKM2 to Promote the Warburg Effect and Tumor Growth" Sci. Signal., Nov. 17, 2009, vol. 2, Issue 97, p. ra73.
Hulleman, et al., "Pyruvate kinase M2 and prednisolone resistance in acute lymphoblastic leukemia." Haematologica. Sep. 2009; 94(9): 1322-1324.
Inglese et al., "Quantitative high-throughput screening: A titration-based approach that efficiently identifies biological activities in large chemical libraries," Proc. Natl. Acad. Sci., 103 (31), 11473-11478 (2006).
International Preliminary Report for related application No. PCT/US2011/067752 dated Apr. 11, 2013.
International Preliminary Report on patentability for International Application No. PCT/US2007/017519, mailed Jul. 8, 2008.
International Preliminary Report on Patentability for PCT/US2008/009828, dated Feb. 16, 2010.
International Preliminary Report on Patentability for PCT/US2010/040489 dated Jan. 12, 2012.
International Preliminary Report on Patentability, Application No. PCT/US2009/060237, dated Apr. 12, 2011.
International Search Report & Written Opinion for PCT/US10/030139 dated Dec. 10, 2010.
International Search Report & Written Opinion for PCT/US10/40485 dated Aug. 11, 2010.
International Search Report and the Written Opinion of the International Search Authority (PCT/US07/17519), mailed Jul. 8, 2008.
International Search Report dated Apr. 4, 2012 for related Application PCT/US2011/065633.
International Search Report dated Mar. 5, 2012 for related international application No. PCT/US2011/067752.
International Search Report dated May 3, 2012 for related application PCT/US2011/066595.
International Search Report for Application No. PCT/US12/60099 dated Jan. 8, 2013.
International Search Report for PCT/US10/040486 dated Sep. 1, 2010.
International Search Report for PCT/US2008/009828, dated Dec. 5, 2008.
International Search Report for PCT/US2010/033610 dated Jul. 22, 2010.
Yan et al., "IDH1 and IDH2 Mutations in Gliomas." The New England Journal of Medicine, 19 Feb. 18-22, 2009, vol. 360, No. 8, pp. 765-773.
Yar et al., "An Annulation Reaction for the Synthesis of Morpholines, Thiomorpholines, and Piperazines from !3-Heteroatom Amino Compounds and Vinyl Sulfonium Salts," Angewandte Chemie., 47 (20),3784-3786 (2008).
Ye et al., Pyruvate kinase M2 promotes de novo serine synthesis to sustain mTORC1 activity and cell proliferation, PNAS 109(18), 2012, pp. 6904-6909.
Conti et al. "Su alcuni analoghi assigenati della benzo-tiazine 2-3-diidro-3-cheto-benzo-1-4-ossazine 6-sostitute" Bollettino Scientifico Della Facolta Di Chimica Industriale Di Bologna (1957) vol. XV, No. 2, pp. 33-36.
Crawford et al., Caplus an 2010:1218943.
European Search report for EP Application No. 10 794 667.5 dated Oct. 9, 2013.
European Search Report for European Application No. 11808773.3 dated Apr. 9, 2014.
European Search Report for European Application No. 11811257.2 dated Apr. 23, 2014.
International Search Report for PCT/US2011/065633 dated Jun. 18, 2013.
Komoriya et al. "Design, synthesis, and biological activity of non-basic compounds as factor Xa inhibitors: SAR study of S1 and aryl binding sites" Bioorganic & Medicinal Chemistry 13 (2005) 3927-3954.
Patel et al. "Synthesis of some new idolinone derivatives containing piperazine moiety" Bulgarian Chemical Communications, 2003 Bol 35 No. 4 pp. 242-244.

(56) References Cited

OTHER PUBLICATIONS

Patel et al. "Synthesis of some new idolinone derivatives containing piperazine moiety" Bulgarian Chemical Communications, 2003 Bol 35 No. 4 pp. 242-244 Abstract Only.

Proisy et al. "Rapid Synthesis of 3-Aminoisoquinoline-5-sulfonamides Using the Buchwald-Hartwig Reaction" Synthesis 2009, No. 4, pp. 0561-0566.

Steiner et al. "Synthesis and Antihypertensive Activity of New 6-Heteroaryl-3-hydrazinopyridazine Derivatives" Journal of Medicinal Chemistry (1981) vol. 24, No. 1, pp. 59-63.

STN File CA, Registry No. 321433-63-0, entered STN on Feb. 12, 2001, Chemical Abstracts Index Name "1H-Pyrrole-2-sulfonamide,1[3-chloro-5-(trifluoromethyl)-2-pyridinyl]-N-phenyl" Available though Key Organics (under the BIONET brand) Jan. 1994.

STN File CA, Registry No. 321433-64-1, entered STN on Feb. 12, 2001, Chemical Abstracts Index Name "1H-Pyrrole-2-sulfonamide,1[3-chloro-5-(trifluoromethyl)-2-pyridinyl]-N-(4-methphenyl)" Available though Key Organics (under the BIONET brand) Jan. 1994.

STN File CA, Registry No. 321433-65-2, entered STN on Feb. 12, 2001, Chemical Abstracts Index Name "1H-Pyrrole-2-sulfonamide,1[3-chloro-5-(trifluoromethyl)-2-pyridinyl]-N-(3,5-dimethylphenyl)" Available though Key Organics (under the BIONET brand) Jan. 1994.

STN File CA, Registry No. 321433-66-3, entered STN on Feb. 12, 2001, Chemical Abstracts Index Name "1H-Pyrrole-2-sulfonamide,1[3-chloro-5-(trifluoromethyl)-2-pyridinyl]-N-(4-methoxyphenyl)" Available though Key Organics (under the BIONET brand) Jan. 1994.

STN File CA, Registry No. 321433-68-5, entered STN on Feb. 12, 2001, Chemical Abstracts Index Name "1H-Pyrrole-2-sulfonamide,1[3-chloro-5-(trifluoromethyl)-2-pyridinyl]-N-propyl" Available though Key Organics (under the BIONET brand) Jan. 1994.

STN File CA, Registry No. 321433-69-6, entered STN on Feb. 12, 2001, Chemical Abstracts Index Name "1H-Pyrrole-2-sulfonamide,1[3-chloro-5-(trifluoromethyl)-2-pyridinyl]-N-(2-methoxyethyl)" Available though Key Organics (under the BIONET brand) Jan. 1994.

STN File CA, Registry No. 338397-92-5, entered STN on May 25, 2001, Chemical Abstracts Index Name "1H-Pyrrole-2-sulfonamide, 1[3-chloro-5-(trifluoromethyl)-2-pyridinyl]-N,N-dimethyl" Available though Key Organics (under the BIONET brand) Feb. 1993.

STN File CA, Registry No. 338397-95-8, entered STN on May 25, 2001, Chemical Abstracts Index Name "1H-Pyrrole-2-sulfonamide, N-[(4-chlorophenyl)-1[3-chloro-5-(trifluoromethyl)-2-pyridinyl]" Available though Key Organics (under the BIONET brand) Feb. 1993.

STN File CA, Registry No. 338397-96-9, entered STN on May 25, 2001, Chemical Abstracts Index Name "1H-Pyrrole-2-sulfonic acid, 1[3-chloro-5-(trifluoromethyl)-2-pyridinyl]-4-chlorophenyl ester" Available though Key Organics (under the BIONET brand) Feb. 1993.

STN File CA, Registry No. 338406-58-9, entered STN on May 25, 2001, Chemical Abstracts Index Name "1H-Pyrrole-2-sulfonamide, 1[3-chloro-5-(trifluoromethyl)-2-pyridinyl]-N[2-(trifluoromethyl)phenyl]" Available though Key Organics (under the BIONET brand) Mar. 1993.

STN File CA, Registry No. 338406-64-7, entered STN on May 25, 2001, Chemical Abstracts Index Name "1H-Pyrrole-2-sulfonamide, 1[3-chloro-5-(trifluoromethyl)-2-pyridinyl]-N-(3-pyridinylmethyl)" Available though Key Organics (under the BIONET brand) Mar. 1993.

STN File CA, Registry No. 338406-72-7, entered STN on May 25, 2001, Chemical Abstracts Index Name "1H-Pyrrole-2-sulfonamide, N-[(4-chlorophenyl)methyl]-1[3-chloro-5-(trifluoromethyl)-2-pyridinyl]" Available though Key Organics (under the BIONET brand) Mar. 1993.

STN File CA, Registry No. 338407-11-7, entered STN on May 25, 2001, Chemical Abstracts Index Name "1H=Pyrrole-2-sulfonamide, 1[3-chloro-5-(trifluoromethyl)-2-pyridinyl]-N[3-chloro-4-[[5-(trifluoromethyl)-2-pyridinyl]oxy]phenyl]" Available though Key Organics (under the BIONET brand) Mar. 1993.

STN File CA, Registry No. 338407-13-9, entered STN on May 25, 2001, Chemical Abstracts Index Name "Benzoic acid, 3-[[[1[3-chloro-5-(trifluoromethyl)-2-pyridinyl]-1H-pyrrol-2-yl]sulfonyl]amino]" Available though Key Organics (under the BIONET brand) Mar. 1993.

Supplemental EP Search Report for European Application No. 10714131.9 dated Oct. 17, 2014.

Wong et al. "PKM2, a Central Point of Regulation in Cancer Metabolism" International Journal of Cell Biology (2013) vol. 2013, pp. 1-11.

N-(4-(AZETIDINE-1-CARBONYL) PHENYL)-(HETERO-) ARYLSULFONAMIDE DERIVATIVES AS PYRUVATE KINASE M2 (PMK2) MODULATORS

CLAIM OF PRIORITY

This application is a national stage application under 35 U.S.C. §371 of International Application No. PCT/US2011/065633, filed Dec. 16, 2011, and published as International Publication No. WO 2012/083246 on Jun. 21, 2012, which claims priority from U.S. Ser. No. 61/424,395, filed Dec. 17, 2010; the content of each of these applications is incorporated herein by reference in its entirety.

BACKGROUND OF INVENTION

Cancer cells rely primarily on glycolysis to generate cellular energy and biochemical intermediates for biosynthesis of lipids and nucleotides, while the majority of "normal" cells in adult tissues utilize aerobic respiration. This fundamental difference in cellular metabolism between cancer cells and normal cells, termed the Warburg Effect, has been exploited for diagnostic purposes, but has not yet been exploited for therapeutic benefit.

Pyruvate kinase (PK) is a metabolic enzyme that converts phosphoenolpyruvate to pyruvate during glycolysis. Four PK isoforms exist in mammals: the L and R isoforms are expressed in liver and red blood cells, the M1 isoform is expressed in most adult tissues, and the M2 isoform is a splice variant of M1 expressed during embryonic development. All tumor cells exclusively express the embryonic M2 isoform. A well-known difference between the M1 and M2 isoforms of PK is that M2 is a low-activity enzyme that relies on allosteric activation by the upstream glycolytic intermediate, fructose-1,6-bisphosphate (FBP), whereas M1 is a constitutively active enzyme.

All tumor cells exclusively express the embryonic M2 isoform of pyruvate kinase, suggesting PKM2 as a potential target for cancer therapy. PKM2 is also expressed in adipose tissue and activated T-cells. Phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation will lead to the loss of allosteric control of PKM2 needed for shunting biochemical intermediates from glycolysis into biosynthesis of nucleotides and lipids. Thus, the activation of PKM2 can inhibit the growth and proliferation of cancer cells, activated immune cells, and fat cells. Activation of PKM2 may therefore be effective in the treatment of cancer, obesity, diabetes, autoimmune conditions, and proliferation-dependent diseases, e.g., benign prostatic hyperplasia (BPH).

There is a continuing need for novel treatments of diseases such as cancer, diabetes, obesity, autoimmune conditions, proliferation-dependent diseases (e.g., BPH), and other diseases related to the function of pyruvate kinase (e.g., PKM2).

SUMMARY OF INVENTION

Described herein are compounds that activate pyruvate kinase M2 (PKM2) and pharmaceutically acceptable salts, solvates, and hydrates thereof, for example, compounds that activate PKM2. Also provided are pharmaceutical compositions comprising a compound provided herewith and the use of such compositions in methods of treating diseases and conditions that are related to pyruvate kinase function (e.g., PKM2 function), including, e.g., cancer, diabetes, obesity, autoimmune disorders, and benign prostatic hyperplasia (BPH).

In one embodiment, provided is a compound of formula (I):

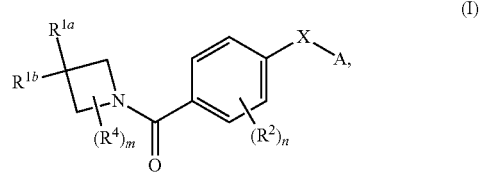

or a pharmaceutically acceptable salt thereof, wherein:

A is aryl or heteroaryl, wherein the aryl or heteroaryl is optionally substituted, and the aryl or heteroaryl is optionally fused to an optionally substituted carbocyclyl or an optionally substituted heterocyclyl;

X is selected from —NH—S(O)$_2$—, —N(alkyl)-S(O)$_2$—, —S(O)$_2$—N(H)—, and —S(O)$_2$—N(alkyl)-;

$R^{1a}$ is selected from hydrogen, alkyl, aryl, and arylalkyl; and $R^{1b}$ is selected from $OR^3$, $N(alkyl)R^3$ and $NHR^3$; or $R^{1a}$ is alken-1-yl and $R^{1b}$ is absent;

each $R^2$ is independently selected from halo, haloalkyl, alkyl, alkoxy and hydroxyl;

$R^3$ is selected from hydrogen, alkyl, optionally substituted aryl, optionally substituted heteroaryl, arylalkyl, C(O)$R^a$, and C(O)N(H)$R^a$, wherein $R^a$ is selected from alkyl, alkenyl, aryl, heteroaryl, arylalkyl and heteroarylalkyl; and wherein any aryl or heteroaryl portion of $R^a$ is optionally substituted;

each $R^4$ is independently selected from haloalkyl, alkyl, alkoxy and hydroxyl n is 0, 1, or 2;

m is 0, 1, or 2.

In another embodiment, provided is a method for treating or preventing (e.g., treating) a disease, condition or disorder as described herein comprising administering a compound provided herein, a pharmaceutically acceptable salt thereof, or pharmaceutical composition thereof.

In another embodiments, provided is a method of increasing the level of PKM2 activity and/or glycolysis in a patient in need thereof. The method comprises the step of administering an effective amount of a compound described herein to the patient in need thereof, thereby increasing the level of PKM2 activity and/or glycolysis in the patient. In some embodiments, a compound or a composition described herein is used to maintain PKM2 in its active conformation or activate pyruvate kinase activity in proliferating cells as a means to divert glucose metabolites into catabolic rather than anabolic processes in the patient.

In another embodiment, provided is a method of inhibiting cell proliferation in a patient in need thereof. The method comprises the step of administering an effective amount of a compound described herein to the patient in need thereof, thereby inhibiting cell proliferation in the patient. In one aspect this method can inhibit growth of a transformed cell, more specifically a cancer cell. In another aspect the method generally inhibits growth of a PKM2-dependent cell that undergoes aerobic glycolysis.

In another embodiment, provided is a method of treating a patient suffering from or susceptible to a disease or disorder associated with reduced PKM2 activity or reduced glycolysis in a patient in need thereof. The method comprises the step of administering an effective amount of a compound described herein to the patient in need thereof, thereby treating, preventing or ameliorating the disease or disorder in the patient. In certain embodiment the compound described herein is provided in a pharmaceutical composition. In certain embodiments, the method includes the step of identifying or selecting a patient who would benefit from activation of PKM2 prior to treatment. Identifying or selecting such a patient can be on the basis of the level of PKM2 activity in a cell of the patient. In one aspect, the selected patient is suffering from or susceptible to unwanted cell growth or proliferation, e.g., cancer, obesity, diabetes, atherosclerosis, restenosis, and autoimmune diseases. In another aspect, the selected patient is suffering from a cancer associated with PKM2 function.

In another embodiment, the compound described herein is administered at a dosage and frequency sufficient to increase lactate production or oxidative phosphorylation.

DETAILED DESCRIPTION

The details of construction and the arrangement of components set forth in the following description or illustrated in the drawings are not meant to be limiting. Embodiments can be practiced or carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

DEFINITIONS

The term "halo" or "halogen" refers to any radical of fluorine, chlorine, bromine or iodine.

The term "alkyl" refers to a monovalent hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. In certain aspects, the term "alkyl" refers to a monovalent hydrocarbon chain that may be a straight chain or branched chain, containing 1 to 6 carbon atoms. In other aspects, the term "alkyl" refers to a monovalent hydrocarbon chain that may be a straight chain or branched chain, containing 1 to 4 carbon atoms.

The term "haloalkyl" refers to an alkyl in which one or more hydrogen atoms are replaced by halo, and includes alkyl moieties in which all hydrogens have been replaced by halo (e.g., perfluoroalkyl).

The term "alkenyl" refers to a monovalent straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. In certain aspects, the term "alkenyl" refers to a monovalent straight or branched hydrocarbon chain containing 2-6 carbon atoms and having one or more double bonds. In other aspects, the term "alkenyl" refers to a monovalent straight or branched hydrocarbon chain containing 2-4 carbon atoms and having one or more double bonds.

The term "alkynyl" refers to a monovalent straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The terms "alkylamino" and "dialkylamino" refer to —NH (alkyl) and —NH(alkyl)$_2$ radicals respectively.

The term "aralkylamino" refers to a —NH(aralkyl) radical.

The term "alkylaminoalkyl" refers to a (alkyl)NH-alkyl-radical.

The term "dialkylaminoalkyl" refers to a (alkyl)$_2$N-alkyl-radical.

The term "mercapto" refers to an —SH radical.

The term "thioalkoxy" refers to an —S-alkyl radical.

The term "thioaryloxy" refers to an —S-aryl radical.

The term "alkoxy" refers to an —O-alkyl radical.

The term "aryl" refers to a monocyclic, bicyclic, or tricyclic aromatic hydrocarbon ring system. Examples of aryl moieties include, but are not limited to, phenyl, naphthyl, and anthracenyl.

The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "carbocyclyl" refers to a non-aromatic, monocyclic, bicyclic, or tricyclic hydrocarbon ring system. Carbocyclyl groups include fully saturated ring systems (e.g., cycloalkyls), and partially saturated ring systems.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). Examples of cycloalkyl moieties include, but are not limited to, cyclopropyl, cyclohexyl, methylcyclohexyl, adamantyl, and norbornyl.

The term "heteroaryl" refers to a fully aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms selected independently from N, O, or S if monocyclic, bicyclic, or tricyclic, respectively).

The term "heterocyclyl" refers to a nonaromatic, 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The heteroatom may optionally be the point of attachment of the heterocyclyl substituent. Examples of heterocyclyl include, but are not limited to, tetrahydrofuranyl, tetrahydropyranyl, piperidinyl, morpholino, pyrrolinyl, pyrimidinyl, and pyrrolidinyl.

Bicyclic and tricyclic ring systems containing one or more heteroatoms and both aromatic and non-aromatic rings are considered to be heterocyclyl groups according to the present definition. Such bicyclic or tricyclic ring systems may be alternately characterized as being an aryl or a heteroaryl fused to a carbocyclyl or heterocyclyl, particularly in those instances where the ring bound to the rest of the molecule is required to be aromatic.

The terms "heteroarylalkyl" and "heteroaralkyl", as used herein, refers to an alkyl group substituted with a heteroaryl group.

The term "heterocyclylalkyl", as used herein, refers to an alkyl group substituted with a heterocyclyl group.

The term "acyl" refers to an alkylcarbonyl, cycloalkylcarbonyl, arylcarbonyl, heterocyclylcarbonyl, or heteroarylcarbonyl substituent, any of which may be further substituted (e.g., by one or more substituents).

All ring systems (i.e., aryl, heteroaryl, carbocyclyl, cycloalkyl, heterocyclyl, etc.) or ring system portions of groups (e.g., the aryl portion of an aralkyl group) are optionally substituted at one or more substitutable carbon atoms with substituents independently selected from: halo, —C≡N, $C_1$-$C_4$ alkyl, =O, $C_3$-$C_7$ cycloalkyl, $C_1$-$C_4$ alkyl, —OH, —O—($C_1$-$C_4$ alkyl)-, —SH, —S—($C_1$-$C_4$ alkyl), —($C_1$-$C_4$ alkyl)-N($R^b$)($R^b$), —N($R^b$)($R^b$), —O—($C_1$-$C_4$ alkyl)-N($R^b$)($R^b$), —($C_1$-$C_4$ alkyl)-O—($C_1$-$C_4$ alkyl)-N($R^b$)($R^b$), —C(O)—N($R^b$)($R^b$), —($C_1$-$C_4$ alkyl)-C(O)—N($R^b$)($R^b$), —O-(heteroaryl), —O-(heterocycle), —O-phenyl, -heteroaryl, -heterocycle, and -phenyl, wherein:
  each $R^b$ is independently selected from hydrogen, and —$C_1$-$C_4$ alkyl; or
  two $R^b$ are taken together with the nitrogen atom to which they are bound to form a 4- to 8-membered saturated heterocycle optionally comprising one additional heteroatom selected from N, S, S(=O), S(=O)$_2$, and O,
  any alkyl substituent is optionally further substituted with one or more of —OH, —O—($C_1$-$C_4$ alkyl), halo, —NH$_2$, —NH($C_1$-$C_4$ alkyl), or —N($C_1$-$C_4$ alkyl)$_2$; and
  any carbon atom on a phenyl, cycloalkyl, heteroaryl or heterocycle substituent is optionally further substituted with one or more of —($C_1$-$C_4$ alkyl), —($C_1$-$C_4$ fluoroalkyl), —OH, —O—($C_1$-$C_4$ alkyl), —O—($C_1$-$C_4$ fluoroalkyl), halo, —NH$_2$, —NH($C_1$-$C_4$ alkyl), or —N($C_1$-$C_4$ alkyl)$_2$;

All heterocyclyl ring systems (and any heterocyclyl substituents on any ring system) is optionally substituted on one or more any substitutable nitrogen atom with —$C_1$-$C_4$ alkyl, or fluoro-substituted $C_1$-$C_4$ alkyl.

The term "substituted" refers to the replacement of a hydrogen atom by another group.

The term "oxo" refers to an oxygen atom, which forms a carbonyl when attached to carbon, an N-oxide when attached to nitrogen, and a sulfoxide or sulfone when attached to sulfur.

The term "selective" is meant at least 2-fold, 3-fold, 4-fold, 5-fold, 6-fold, or 10-fold greater activation of PKM2 than PKM1.

The term "activator" as used herein means an agent that (measurably) increases the activity of PKM2 or causes PKM2 activity to increase to a level that is greater than PKM2's basal levels of activity. For example, the activator may mimic the effect caused by a natural ligand (e.g., FBP). The activator effect caused by a compound provided herein may be to the same, or to a greater, or to a lesser extent than the activating effect caused by a natural ligand, but the same type of effect is caused. A compound provided herein can be evaluated to determine if it is an activator by measuring either directly or indirectly the activity of the pyruvate kinase when subjected to said compound. The activity of PKM2 can be measured, for example, by monitoring the concentration of a substrate such as ATP or NADH.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

Compounds

Provided herein is a compound of Formula (I) or a pharmaceutically acceptable salt thereof as described above in the Summary of the Invention.

In one embodiment, provided is a compound of Formula I, wherein m is 0 (i.e., there are no $R^4$ substituents on the azetindinyl ring), the compound having Formula (Ia):

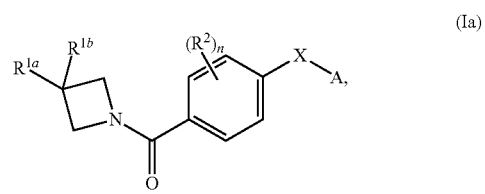

(Ia)

or a pharmaceutically acceptable salt thereof, wherein:
A is aryl or heteroaryl, wherein the aryl or heteroaryl is optionally substituted; and the aryl or heteroaryl is optionally fused to an optionally substituted carbocyclyl or an optionally substituted heterocyclyl;
X is selected from —N(H)—S(O)$_2$—, —N(alkyl)-S(O)$_2$—, —S(O)$_2$—N(alkyl)- and —S(O)$_2$—N(H)—;
$R^{1a}$ is selected from hydrogen, alkyl, aryl, and arylalkyl; and $R^{1b}$ is selected from OR$^3$, N(alkyl)R$^3$ and NHR$^3$; or
$R^{1a}$ is alken-1-yl and $R^{1b}$ is absent;
each $R^2$ is independently selected from halo, haloalkyl, alkyl, alkoxy and hydroxyl;
$R^3$ is selected from hydrogen, alkyl, optionally substituted aryl, optionally substituted heteroaryl, arylalkyl, C(O)R$^a$, and C(O)N(H)R$^a$, wherein R$^a$ is selected from alkyl, alkenyl, aryl, heteroaryl, arylalkyl and heteroarylalkyl; and wherein any aryl or heteroaryl portion of R$^a$ is optionally substituted; and n is 0, 1, or 2.

In certain aspects of the above embodiment, A is an optionally substituted bicyclic heteroaryl. In a more specific aspect, A is quinolin-8-yl and the compound has the structure set forth in formula (II), or a pharmaceutically acceptable salt thereof:

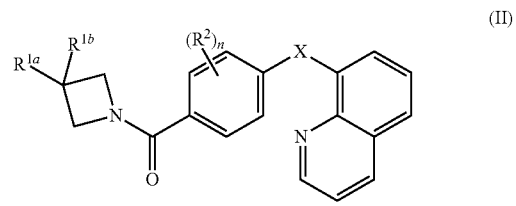

(II)

wherein:
$R^{1a}$, $R^{1b}$, $R^2$, $R^3$, X, and n are as defined for Formula Ia.

In certain embodiments of Formula I, Ia or II, $R^{1a}$ is hydrogen.

In certain embodiments of Formula I, Ia or II, $R^{1a}$ is optionally substituted phenyl.

In some embodiments of Formula I, Ia or II, $R^{1a}$ is alkyl. In one aspect of these embodiments, $R^{1a}$ is methyl.

In certain embodiments of Formula I, Ia or II, $R^{1a}$ is arylalkyl, wherein the aryl portion is optionally substituted. In one aspect of these embodiments, $R^{1a}$ is optionally substituted benzyl.

In some embodiments of Formula I, Ia or II, $R^{1b}$ is —OR$^3$. In one aspect of these embodiments, $R^{1b}$ is hydroxyl. In an alternate aspect $R^{1b}$ is —O-alkyl. In a more specific aspect, $R^{1b}$ is methoxy. In still another aspect $R^{1b}$ is optionally substituted phenoxy. In another aspect $R^{1b}$ is optionally substituted benzoxy. In another aspect $R^{1b}$ is optionally substituted —OC(O)-benzyl. In still another aspect, $R^{1b}$ is optionally substituted —OC(O)-pyridinyl. In another aspect, $R^{1b}$ is —OC(O)NH(alkyl). In a more specific aspect, $R^{1b}$ is —OC(O)NH(CH(CH$_3$)$_2$). In another aspect, $R^{1b}$ is optionally substituted —OC(O)NH(heteroaryl). In a more specific aspect, $R^{1b}$ is optionally substituted —OC(O)NH(pyridinyl).

In some embodiments of Formula I, Ia or II, $R^{1b}$ is NHR$^3$ or N(alkyl)R$^3$. In one aspect of these embodiments, $R^{1b}$ is NHR$^3$. In an alternate aspect $R^{1b}$ is N(CH$_3$)R$^3$. In another aspect of these embodiments R$^3$ is optionally substituted aryl. In a more specific aspect, R$^3$ is optionally substituted phenyl. In another aspect of these embodiments R$^3$ is optionally substituted aralkyl. In a more specific aspect, R$^3$ is optionally substituted benzyl. In another aspect of these embodiments R$^3$ is optionally substituted heteroaryl. In a more specific aspect, R$^3$ is optionally substituted pyridinyl. In another aspect of these embodiments R$^3$ is optionally substituted —C(O)-heteroaryl. In a more specific aspect, R$^3$ is optionally substituted —C(O)-pyridinyl. In another aspect of these embodiments R$^3$ is optionally substituted —C(O)—NH-heteroaryl. In a more specific aspect, R$^3$ is optionally substituted —C(O)—NH-pyridinyl. In still another aspect of these embodiments R$^3$ is —C(O)—NH-alkyl or —C(O)—NH-alkenyl. In a more specific aspect, R$^3$ is —C(O)—NH—CH(CH$_3$)$_2$. In another more specific aspect, R$^3$ is —C(O)—NH—CH$_2$—CH=CH$_2$.

In certain embodiments of Formula I, Ia or II, n is 0 or 1. In one aspect of an embodiment where n is 1, R$^2$ is selected from fluoro, methyl, and methoxy.

In certain embodiments of Formula I, Ia or II, X is —NH—S(O)$_2$ or —S(O)$_2$—NH.

In certain embodiments of Formula II, $R^{1a}$ is phenyl or benzyl, wherein the ring portion of $R^{1a}$ is optionally substituted; and is $R^{1b}$ is hydroxyl. In certain aspects of this embodiment n is 0 or 1; and R$^2$, when present, is selected from methyl, and methoxy. In other aspects of this embodiment, X is —NH—S(O)$_2$.

In some embodiments of Formula II, $R^{1a}$ is hydrogen, and $R^{1b}$ is selected from —NH-phenyl, phenoxy, —NH-pyridin-2-yl, —N(CH$_3$)-phenyl, wherein the phenyl or pyridinyl portion of $R^{1b}$ is optionally substituted. In certain aspects of this embodiment n is 0 or 1; and R$^2$, when present, is selected from methyl, and methoxy. In other aspects of this embodiment, the phenyl or pyridinyl portion of $R^{1b}$ is optionally substituted with methoxy.

In yet another embodiment, the compound is selected from any one of the compounds set forth in Table 1, below:

TABLE 1

Exemplary Compounds of Formula I:

| Compound | Structure |
|---|---|
| 100 | 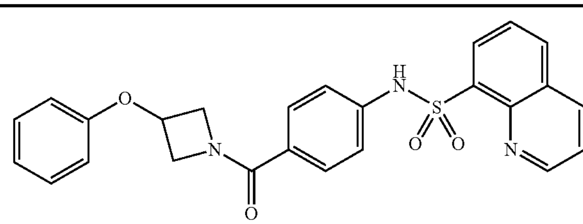 |
| 101 | 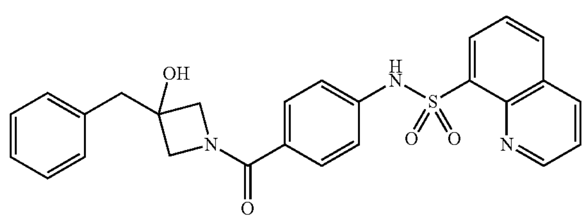 [SMILES: O=C(c1ccc(NS(=O)(=O)c2cccc3cccnc23)cc1)N1CC(O)(Cc2ccccc2)C1] |
| 102 | 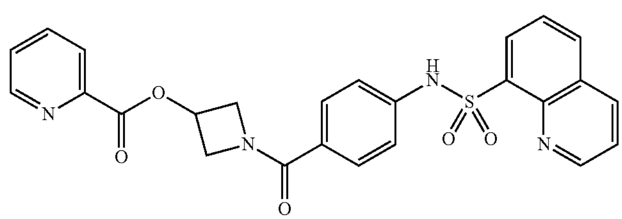 [SMILES: O=C(OC1CN(C(=O)c2ccc(NS(=O)(=O)c3cccc4cccnc34)cc2)C1)c1ccccn1] |
| 103 | 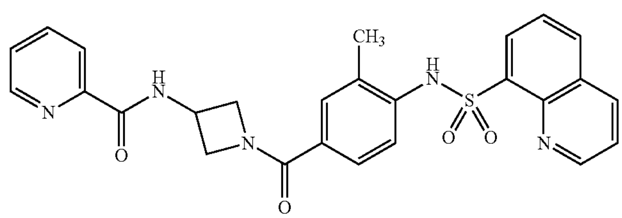 [SMILES: Cc1cc(C(=O)N2CC(NC(=O)c3ccccn3)C2)ccc1NS(=O)(=O)c1cccc2cccnc12] |

9
10
TABLE 1-continued
Exemplary Compounds of Formula I:
| Compound | Structure |
|---|---|
| 104 | 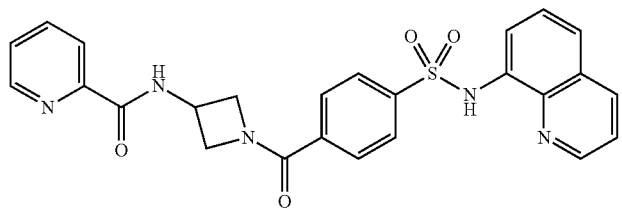 [SMILES: O=C(NC1CN(C(=O)c2ccc(S(=O)(=O)Nc3cccc4cccnc34)cc2)C1)c1ccccn1] |
| 105 | 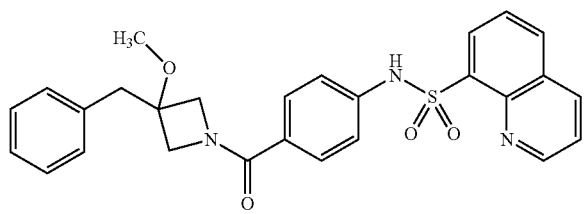 [SMILES: COC1(Cc2ccccc2)CN(C(=O)c2ccc(NS(=O)(=O)c3cccc4cccnc34)cc2)C1] |
| 106 | 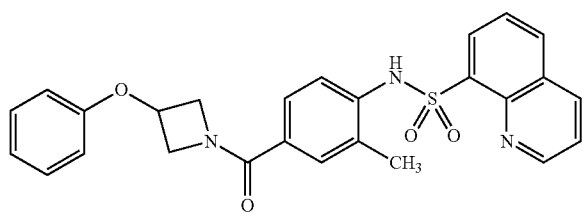 [SMILES: Cc1cc(C(=O)N2CC(Oc3ccccc3)C2)ccc1NS(=O)(=O)c1cccc2cccnc12] |
| 107 | 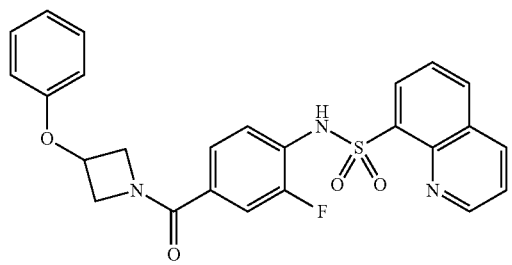 [SMILES: O=C(c1ccc(NS(=O)(=O)c2cccc3cccnc23)c(F)c1)N1CC(Oc2ccccc2)C1] |
| 108 | 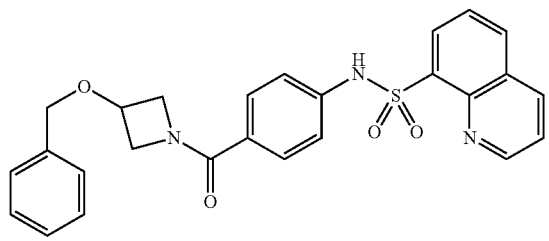 [SMILES: O=C(c1ccc(NS(=O)(=O)c2cccc3cccnc23)cc1)N1CC(OCc2ccccc2)C1] |
| 109 | 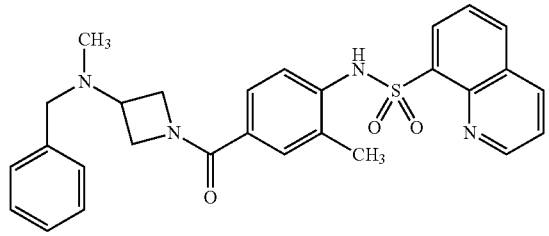 [SMILES: Cc1cc(C(=O)N2CC(N(C)Cc3ccccc3)C2)ccc1NS(=O)(=O)c1cccc2cccnc12] |

TABLE 1-continued

Exemplary Compounds of Formula I:

| Compound | Structure |
|---|---|
| 110 | 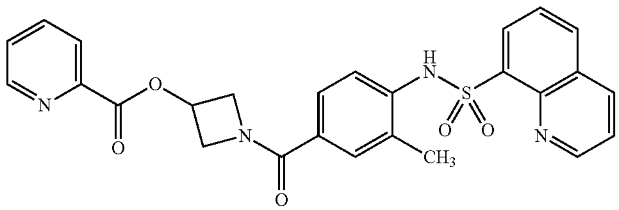 [SMILES: Cc1cc(C(=O)N2CC(OC(=O)c3ccccn3)C2)ccc1NS(=O)(=O)c1cccc2cccnc12] |
| 111 | 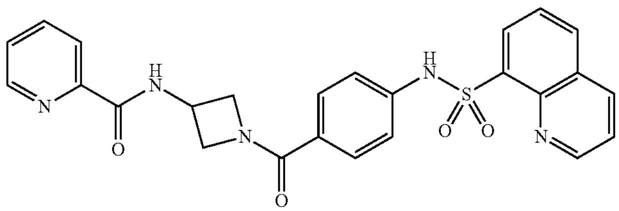 [SMILES: O=C(NC1CN(C(=O)c2ccc(NS(=O)(=O)c3cccc4cccnc34)cc2)C1)c1ccccn1] |
| 112 | 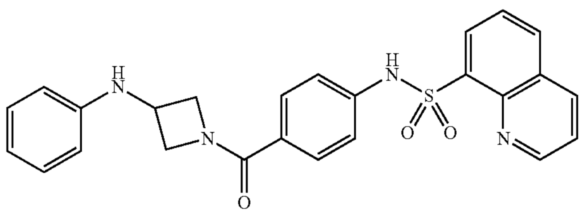 [SMILES: O=C(c1ccc(NS(=O)(=O)c2cccc3cccnc23)cc1)N1CC(Nc2ccccc2)C1] |
| 113 | 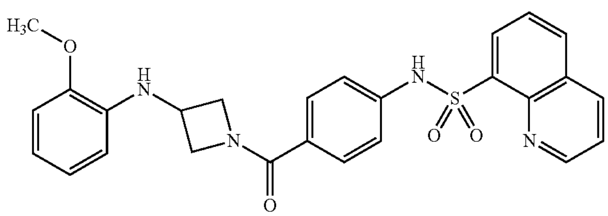 [SMILES: COc1ccccc1NC1CN(C(=O)c2ccc(NS(=O)(=O)c3cccc4cccnc34)cc2)C1] |
| 114 | 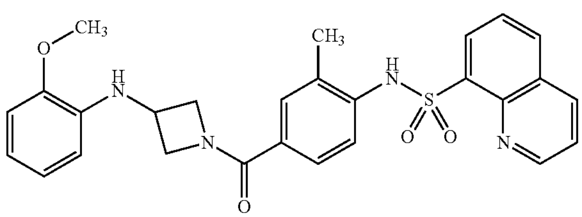 [SMILES: COc1ccccc1NC1CN(C(=O)c2ccc(NS(=O)(=O)c3cccc4cccnc34)c(C)c2)C1] |
| 115 | 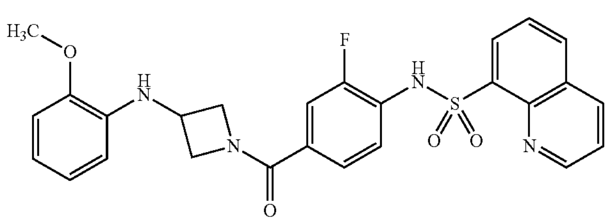 [SMILES: COc1ccccc1NC1CN(C(=O)c2ccc(NS(=O)(=O)c3cccc4cccnc34)c(F)c2)C1] |
| 116 | 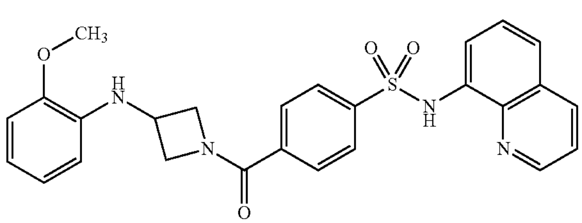 [SMILES: COc1ccccc1NC1CN(C(=O)c2ccc(S(=O)(=O)Nc3cccc4cccnc34)cc2)C1] |

TABLE 1-continued
Exemplary Compounds of Formula I:
| Compound | Structure |
|---|---|
| 117 | 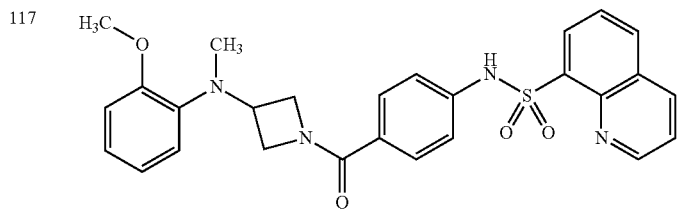 |
| 118 | 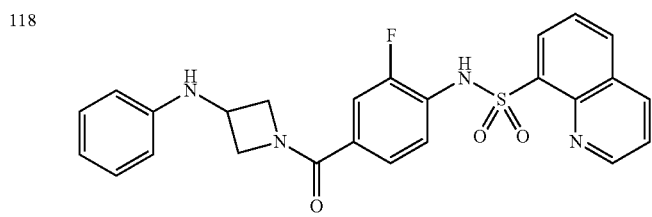 |
| 119 | 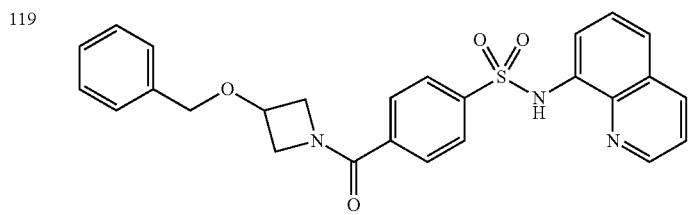 |
| 120 | 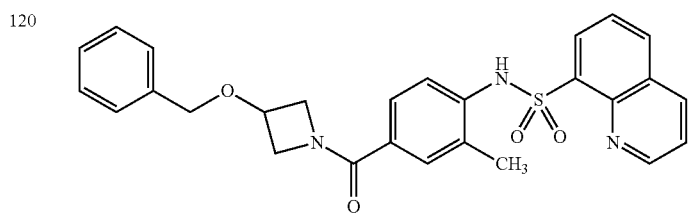 |
| 121 | 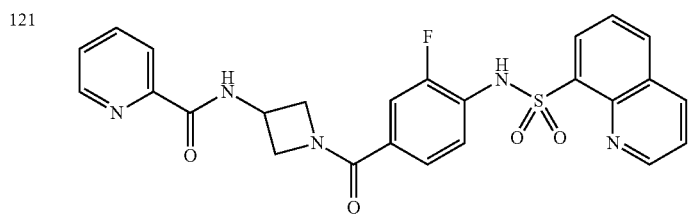 |
| 122 | 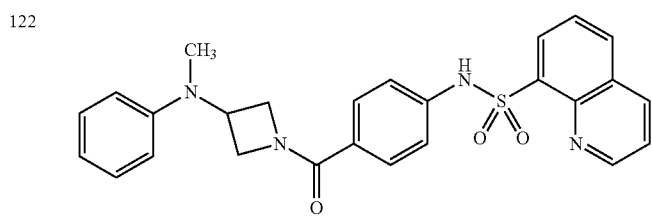 |
| 123 | 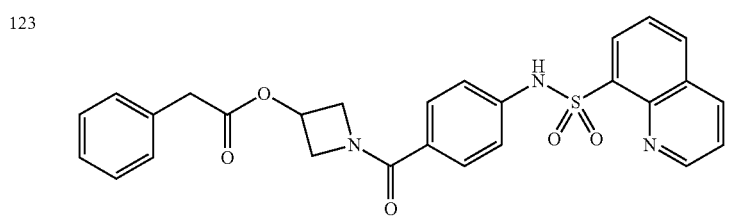 |

15
TABLE 1-continued
Exemplary Compounds of Formula I:
| Compound | Structure |
|---|---|
| 124 | 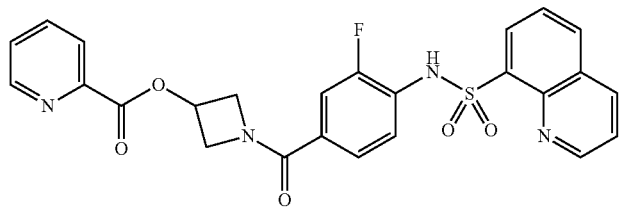 [SMILES: O=C(OC1CN(C(=O)c2ccc(NS(=O)(=O)c3cccc4cccnc34)c(F)c2)C1)c1ccccn1] |
| 125 | 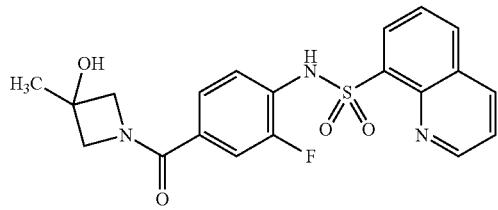 [SMILES: CC1(O)CN(C(=O)c2ccc(NS(=O)(=O)c3cccc4cccnc34)c(F)c2)C1] |
| 126 | 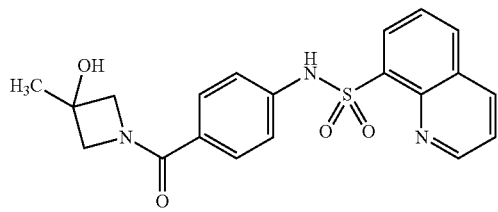 [SMILES: CC1(O)CN(C(=O)c2ccc(NS(=O)(=O)c3cccc4cccnc34)cc2)C1] |
| 127 | 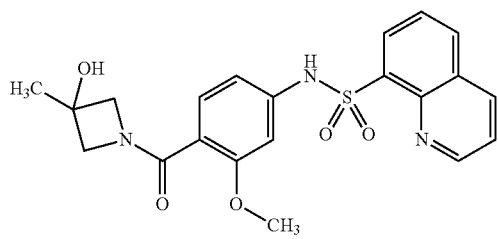 [SMILES: COc1cc(NS(=O)(=O)c2cccc3cccnc23)ccc1C(=O)N1CC(C)(O)C1] |
| 128 | 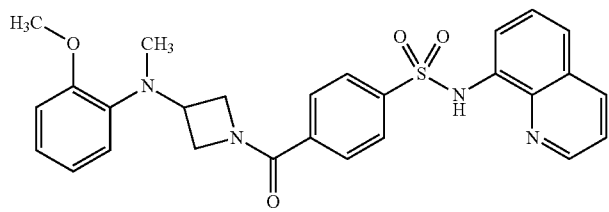 [SMILES: COc1ccccc1N(C)C1CN(C(=O)c2ccc(S(=O)(=O)Nc3cccc4cccnc34)cc2)C1] |
| 129 | 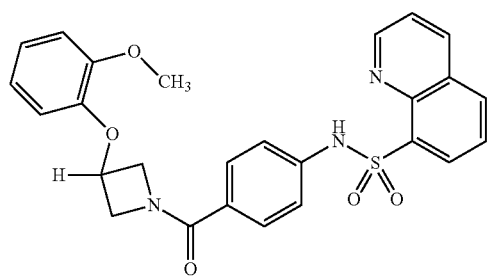 [SMILES: COc1ccccc1OC1CN(C(=O)c2ccc(NS(=O)(=O)c3cccc4cccnc34)cc2)C1] |

TABLE 1-continued
Exemplary Compounds of Formula I:
| Compound | Structure |
|---|---|
| 130 | 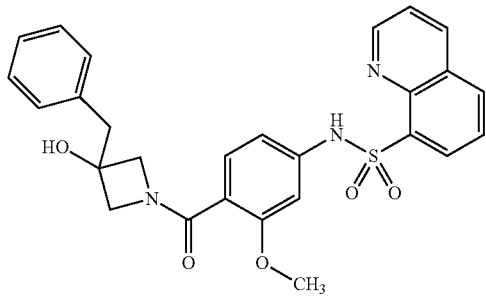 [SMILES: COc1cc(NS(=O)(=O)c2cccc3cccnc23)ccc1C(=O)N1CC(O)(Cc2ccccc2)C1] |
| 131 | 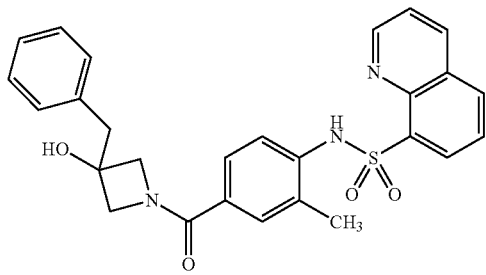 [SMILES: Cc1cc(C(=O)N2CC(O)(Cc3ccccc3)C2)ccc1NS(=O)(=O)c1cccc2cccnc12] |
| 132 | 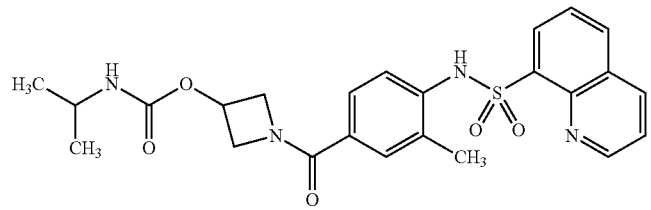 [SMILES: Cc1cc(C(=O)N2CC(OC(=O)NC(C)C)C2)ccc1NS(=O)(=O)c1cccc2cccnc12] |
| 133 | 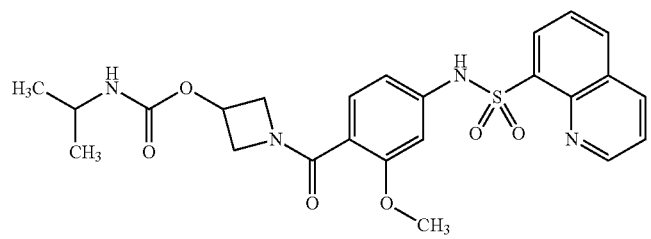 [SMILES: COc1cc(NS(=O)(=O)c2cccc3cccnc23)ccc1C(=O)N1CC(OC(=O)NC(C)C)C1] |
| 134 | 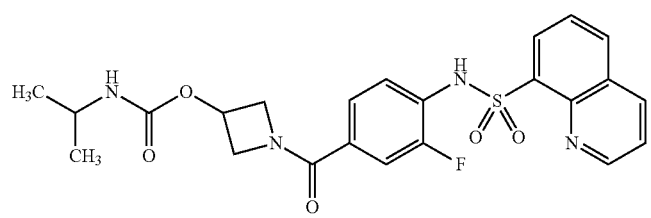 [SMILES: CC(C)NC(=O)OC1CN(C(=O)c2ccc(NS(=O)(=O)c3cccc4cccnc34)c(F)c2)C1] |
| 135 | 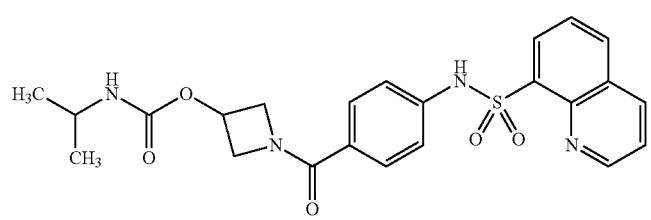 [SMILES: CC(C)NC(=O)OC1CN(C(=O)c2ccc(NS(=O)(=O)c3cccc4cccnc34)cc2)C1] |

TABLE 1-continued
Exemplary Compounds of Formula I:
| Compound | Structure |
|---|---|
| 136 | 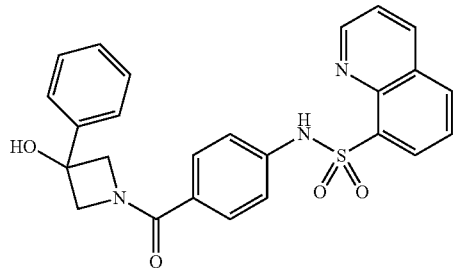 [SMILES: O=C(c1ccc(NS(=O)(=O)c2cccc3cccnc23)cc1)N1CC(O)(c2ccccc2)C1] |
| 137 | 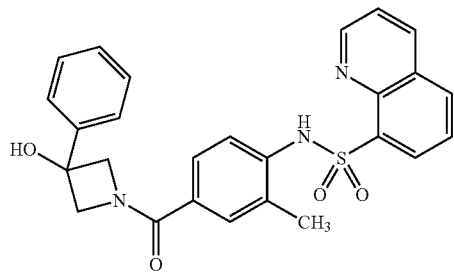 [SMILES: Cc1cc(C(=O)N2CC(O)(c3ccccc3)C2)ccc1NS(=O)(=O)c1cccc2cccnc12] |
| 138 | 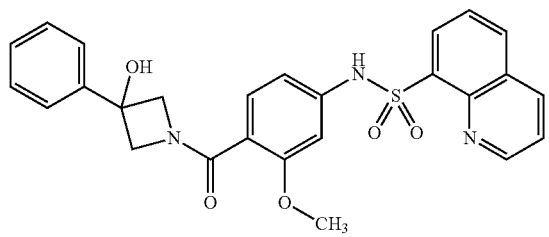 [SMILES: COc1cc(NS(=O)(=O)c2cccc3cccnc23)ccc1C(=O)N1CC(O)(c2ccccc2)C1] |
| 139 | 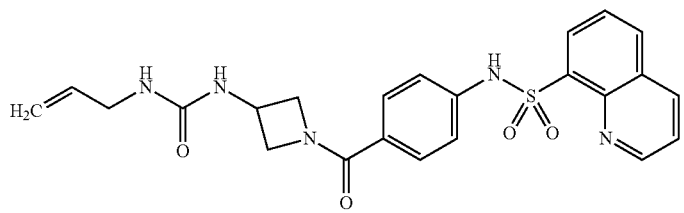 [SMILES: C=CCNC(=O)NC1CN(C(=O)c2ccc(NS(=O)(=O)c3cccc4cccnc34)cc2)C1] |
| 140 | 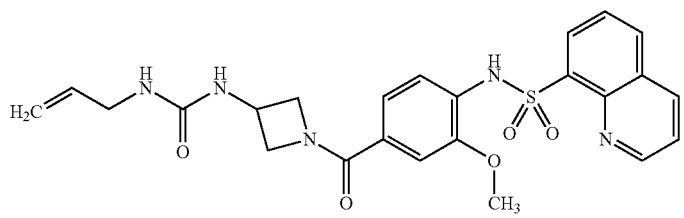 [SMILES: C=CCNC(=O)NC1CN(C(=O)c2ccc(NS(=O)(=O)c3cccc4cccnc34)c(OC)c2)C1] |
| 141 | 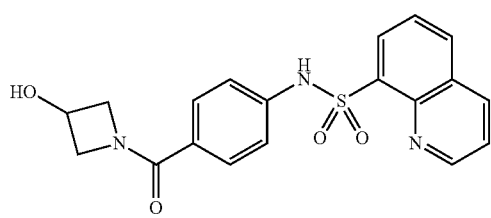 [SMILES: O=C(c1ccc(NS(=O)(=O)c2cccc3cccnc23)cc1)N1CC(O)C1] |

TABLE 1-continued
Exemplary Compounds of Formula I:
| Compound | Structure |
|---|---|
| 142 | 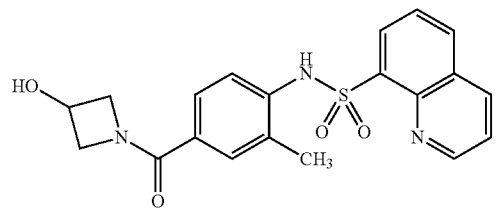 [SMILES: Cc1cc(C(=O)N2CC(O)C2)ccc1NS(=O)(=O)c1cccc2cccnc12] |
| 143 | 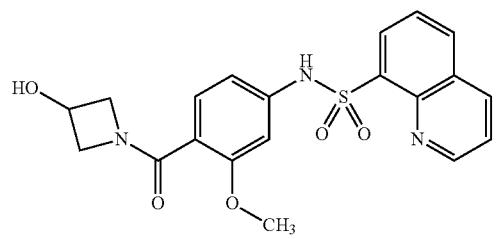 [SMILES: COc1cc(NS(=O)(=O)c2cccc3cccnc23)ccc1C(=O)N1CC(O)C1] |
| 144 | 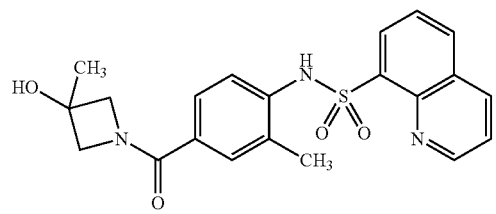 [SMILES: Cc1cc(C(=O)N2CC(C)(O)C2)ccc1NS(=O)(=O)c1cccc2cccnc12] |
| 145 | 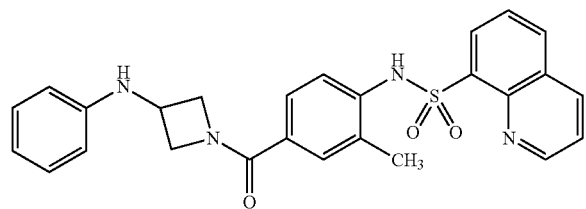 [SMILES: Cc1cc(C(=O)N2CC(Nc3ccccc3)C2)ccc1NS(=O)(=O)c1cccc2cccnc12] |
| 146 | 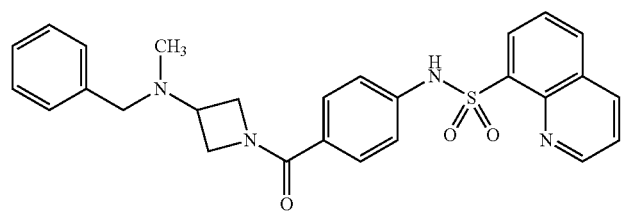 [SMILES: CN(Cc1ccccc1)C1CN(C(=O)c2ccc(NS(=O)(=O)c3cccc4cccnc34)cc2)C1] |
| 147 | 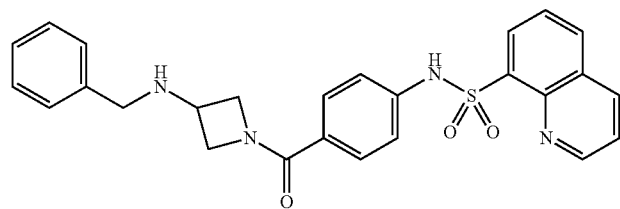 [SMILES: O=C(c1ccc(NS(=O)(=O)c2cccc3cccnc23)cc1)N1CC(NCc2ccccc2)C1] |
| 148 | 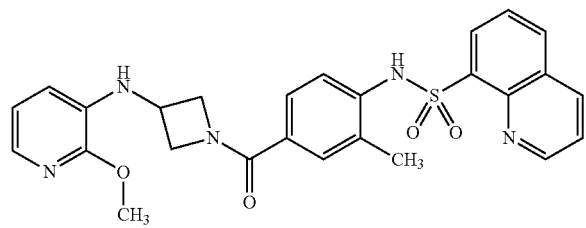 [SMILES: COc1ncccc1NC1CN(C(=O)c2ccc(NS(=O)(=O)c3cccc4cccnc34)c(C)c2)C1] |

TABLE 1-continued

Exemplary Compounds of Formula I:

| Compound | Structure |
|---|---|
| 149 | 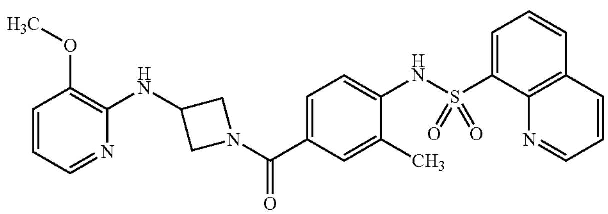 [SMILES: COc1cccnc1NC1CN(C(=O)c2ccc(NS(=O)(=O)c3cccc4cccnc34)c(C)c2)C1] |
| 150 | 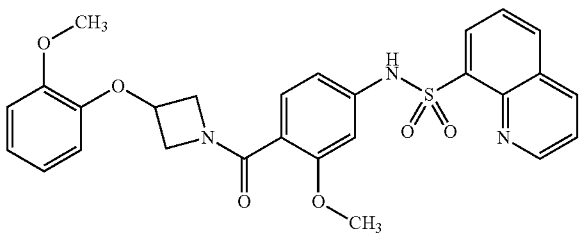 [SMILES: COc1ccccc1OC1CN(C(=O)c2ccc(NS(=O)(=O)c3cccc4cccnc34)cc2OC)C1] |
| 151 | 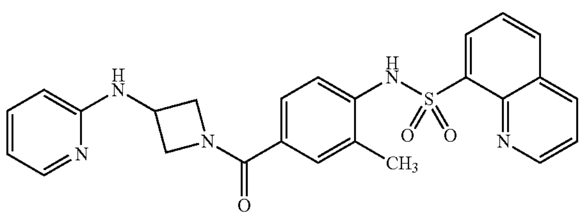 [SMILES: Cc1cc(C(=O)N2CC(Nc3ccccn3)C2)ccc1NS(=O)(=O)c1cccc2cccnc12] |
| 152 | 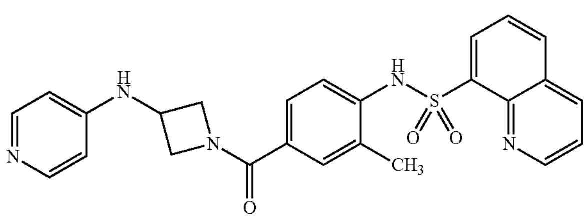 [SMILES: Cc1cc(C(=O)N2CC(Nc3ccncc3)C2)ccc1NS(=O)(=O)c1cccc2cccnc12] |
| 153 | 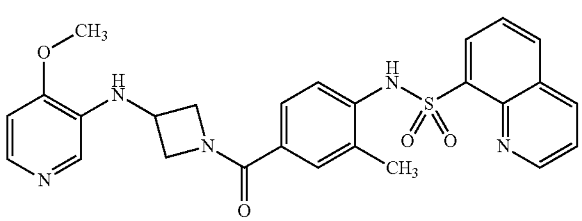 [SMILES: COc1ccncc1NC1CN(C(=O)c2ccc(NS(=O)(=O)c3cccc4cccnc34)c(C)c2)C1] |
| 154 | 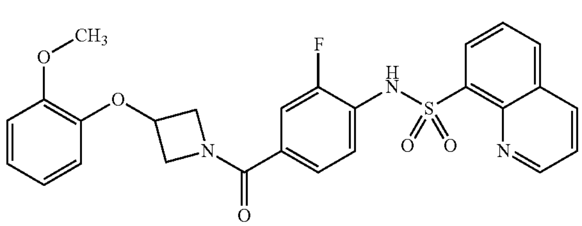 [SMILES: COc1ccccc1OC1CN(C(=O)c2ccc(NS(=O)(=O)c3cccc4cccnc34)c(F)c2)C1] |
| 155 | 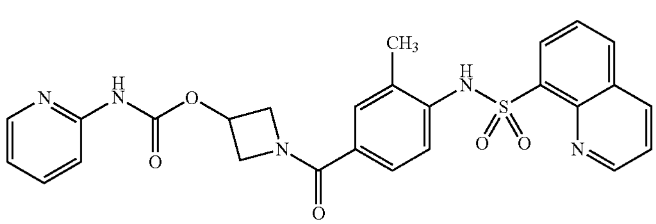 [SMILES: Cc1cc(C(=O)N2CC(OC(=O)Nc3ccccn3)C2)ccc1NS(=O)(=O)c1cccc2cccnc12] |

TABLE 1-continued

Exemplary Compounds of Formula I:

| Compound | Structure |
|---|---|
| 156 | 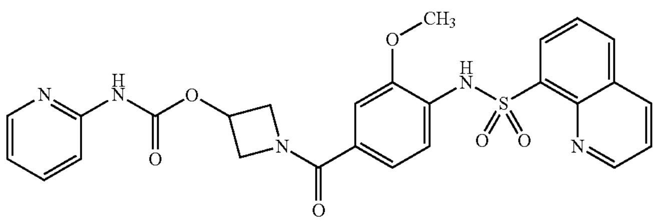 [SMILES: COc1cc(C(=O)N2CC(OC(=O)Nc3ccccn3)C2)ccc1NS(=O)(=O)c1cccc2cccnc12] |
| 157 | 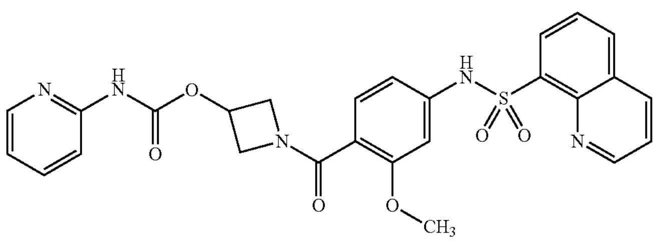 [SMILES: COc1cc(NS(=O)(=O)c2cccc3cccnc23)ccc1C(=O)N1CC(OC(=O)Nc2ccccn2)C1] |
| 158 | 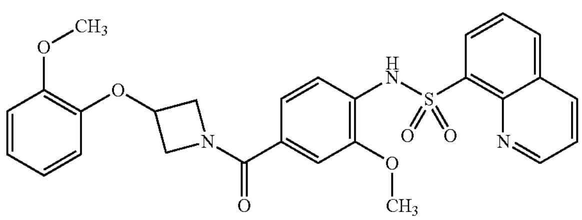 [SMILES: COc1cc(C(=O)N2CC(Oc3ccccc3OC)C2)ccc1NS(=O)(=O)c1cccc2cccnc12] |
| 159 | 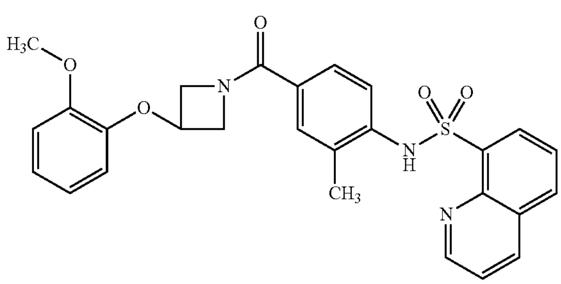 [SMILES: COc1ccccc1OC1CN(C(=O)c2ccc(NS(=O)(=O)c3cccc4cccnc34)c(C)c2)C1] |
| 160 | 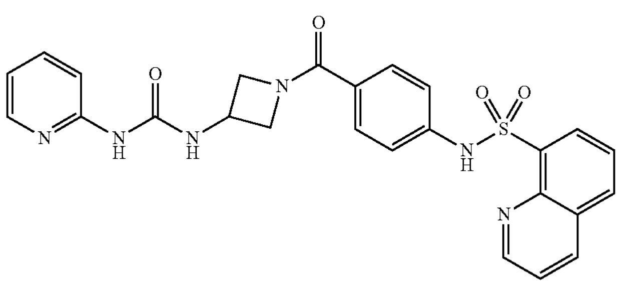 [SMILES: O=C(Nc1ccccn1)NC1CN(C(=O)c2ccc(NS(=O)(=O)c3cccc4cccnc34)cc2)C1] |
| 161 | 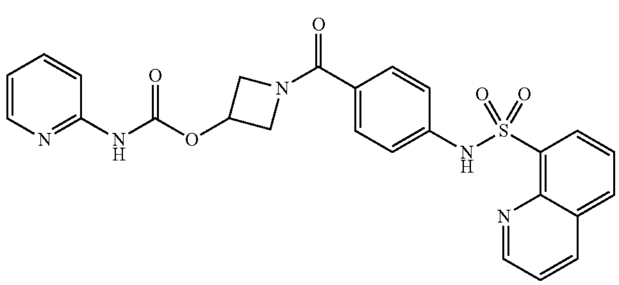 [SMILES: O=C(Nc1ccccn1)OC1CN(C(=O)c2ccc(NS(=O)(=O)c3cccc4cccnc34)cc2)C1] |

TABLE 1-continued

Exemplary Compounds of Formula I:

| Compound | Structure |
|---|---|
| 162 | 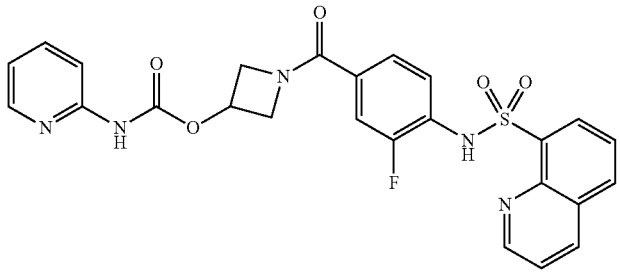 [SMILES: O=C(Nc1ccccn1)OC1CN(C(=O)c2ccc(NS(=O)(=O)c3cccc4cccnc34)c(F)c2)C1] |
| 163 | 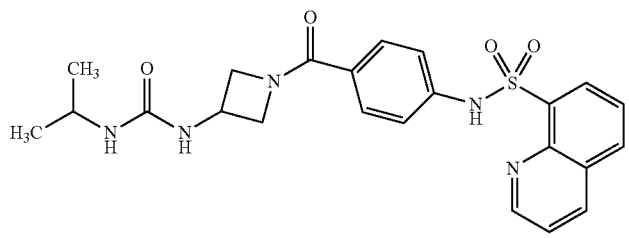 [SMILES: CC(C)NC(=O)NC1CN(C(=O)c2ccc(NS(=O)(=O)c3cccc4cccnc34)cc2)C1] |
| 164 | 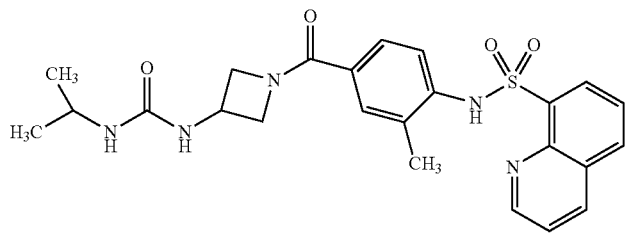 [SMILES: Cc1cc(C(=O)N2CC(NC(=O)NC(C)C)C2)ccc1NS(=O)(=O)c1cccc2cccnc12] |
| 165 | 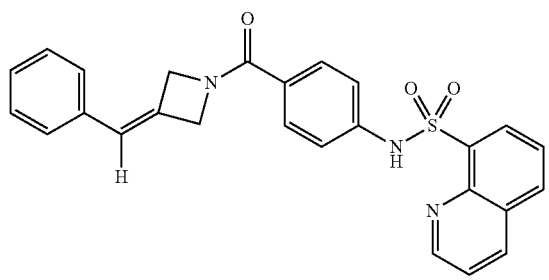 [SMILES: O=C(c1ccc(NS(=O)(=O)c2cccc3cccnc23)cc1)N1CC(=Cc2ccccc2)C1] |
| 166 | 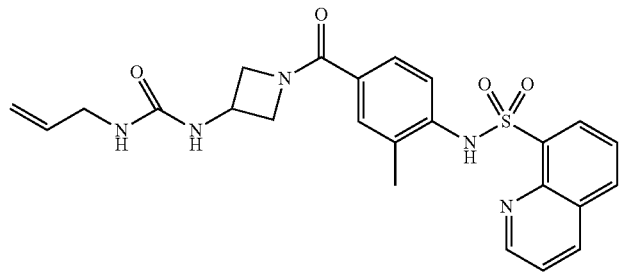 [SMILES: C=CCNC(=O)NC1CN(C(=O)c2ccc(NS(=O)(=O)c3cccc4cccnc34)c(C)c2)C1] |

The compounds described herein can be made using a variety of synthetic techniques, general and specific examples of which are set forth in Example section.

As can be appreciated by the skilled artisan, methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Ency-*

*clopedia of Reagents for Organic Synthesis*, John Wiley and Sons (1995), and subsequent editions thereof.

The compounds provided herein may contain one or more asymmetric centers and thus occur as racemates and racemic mixtures, single enantiomers, individual diastereomers and diastereomeric mixtures. All such isomeric forms of these compounds are expressly included within the scope. Unless otherwise indicated when a compound is named or depicted by a structure without specifying the stereochemistry and has one or more chiral centers, it is understood to represent all possible stereoisomers of the compound. The compounds provided herewith may also contain linkages (e.g., carbon-carbon bonds) or substituents that can restrict bond rotation, e.g., restriction resulting from the presence of a ring or double bond. Accordingly, all cis/trans and E/Z isomers are expressly included.

The compounds provided herein (e.g., of Formula I) may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like. The compounds provided herein may also be represented in multiple tautomeric forms, in such instances, expressly includes all tautomeric forms of the compounds described herein, even though only a single tautomeric form may be represented (e.g., alkylation of a ring system may result in alkylation at multiple sites; all such reaction products are expressly included). All such isomeric forms of such compounds are expressly included. All crystal forms of the compounds described herein are expressly included.

The compounds provided herein include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

The compounds provided herein may be modified by appending appropriate functionalities to enhance selected biological properties, e.g., targeting to a particular tissue. Such modifications are known in the art and include those which increase biological penetration into a given biological compartment (e.g., blood, lymphatic system, central nervous system), increase oral availability, increase solubility to allow administration by injection, alter metabolism and alter rate of excretion.

In an alternate embodiment, the compounds described herein may be used as platforms or scaffolds that may be utilized in combinatorial chemistry techniques for preparation of derivatives and/or chemical libraries of compounds. Such derivatives and libraries of compounds have biological activity and are useful for identifying and designing compounds possessing a particular activity. Combinatorial techniques suitable for utilizing the compounds described herein are known in the art as exemplified by Obrecht, D. and Villalgrodo, J. M., *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, A. W., *Curr. Opin. Chem. Bio.*, (1997) 1, 60. Thus, one embodiment relates to a method of using the compounds described herein for generating derivatives or chemical libraries comprising: 1) providing a body comprising a plurality of wells; 2) providing one or more compounds identified by methods described herein in each well; 3) providing an additional one or more chemicals in each well; 4) isolating the resulting one or more products from each well. An alternate embodiment relates to a method of using the compounds described herein for generating derivatives or chemical libraries comprising: 1) providing one or more compounds described herein attached to a solid support; 2) treating the one or more compounds identified by methods described herein attached to a solid support with one or more additional chemicals; 3) isolating the resulting one or more products from the solid support. In the methods described above, "tags" or identifier or labeling moieties may be attached to and/or detached from the compounds described herein or their derivatives, to facilitate tracking, identification or isolation of the desired products or their intermediates. Such moieties are known in the art. The chemicals used in the aforementioned methods may include, for example, solvents, reagents, catalysts, protecting group and deprotecting group reagents and the like. Examples of such chemicals are those that appear in the various synthetic and protecting group chemistry texts and treatises referenced herein.

Methods of Evaluating Compounds

The compounds described herein can be evaluated for ability to modulate PKM2 (e.g., activate PKM2) by methods known in the art. In some embodiments, compounds described herein are evaluated for ability to modulate PKM2 (e.g., activate PKM2) in serine deficient conditions. In some embodiments, exemplary methods include contacting the compound with a cell-based assay which allows assessment of the ability to modulate (e.g., activate) PKM2. E.g., the candidate compound can be contacted with a cell and measuring the consumption of oxygen or production of lactate. A change in cellular phosphoenolpyruvate, a change in glycerol-phosphate, a change in ribose or deoxyribose, a change in lipid synthesis, or a change in glucose conversion to lipid or nucleic acids or amino acids or protein can also be used to evaluate a compound for its ability to modulate PKM2 (e.g., activate PKM2). The evaluation could also include measuring a change in pyruvate or a determination of an alteration in mitochondrial membrane potential, e.g., as measured by fluorescent potentiometric dyes.

PKM1 and PKM2 for use in the screening/testing method may be produced by any method known in the art for expression of recombinant proteins. For example, nucleic acids that encode the desired polypeptide may be introduced into various cell types or cell-free systems for expression. Eukaryotic (e.g., COS, HEK293T, CHO, and NIH cell lines) and prokaryotic (e.g., *E. coli*) expression systems may be generated in which a PKM sequence is introduced into a plasmid or other vector, which is then used to transform living cells. Constructs in which the PKM cDNA contains the entire open reading frame, or biologically active fragment thereof, are inserted in the correct orientation into an expression plasmid and may be used for protein expression. Prokaryotic and eukaryotic expression systems allow for the expression and recovery of fusion proteins in which the PKM protein is covalently linked to a tag molecule on either the amino terminal or carboxy terminal side, which facilitates identification and/or purification. Examples of tags that can be used include hexahistidine, HA, FLAG, and c-myc epitope tags. An enzymatic or chemical cleavage site can be engineered between the PKM protein and the tag molecule so that the tag can be removed following purification.

The activity of the PKM enzyme measured in the screening/testing assay may be measured by, e.g., monitoring the concentration of a substrate (e.g., ATP or NADH) present in the reaction mixture. Pyruvate, produced by the enzymatic activity of pyruvate kinase, is converted into lactate by lactate dehydrogenase, which requires the consumption of NADH (NADH→NAD+). Thus, the activity of PKM2 can be indirectly measured by monitoring the consumption of NADH through, e.g., fluorescence assays. Additionally, the activity of the PKM2 enzyme can be directly monitored by measuring the production of ATP, as ATP is produced when phosphoenolpyruvate is converted to pyruvate. Methods for monitoring the amount of substrate in a reaction mixture include, e.g., absorbance, fluorescence, Raman scattering, phosphorescence, luminescence, luciferase assays, and radioactivity.

The screening procedure requires the presence of specific components in the reaction mixture. Components utilized in the assay include, e.g., a nucleoside diphosphate (e.g., ADP), phosphoenolpyruvate, NADH, lactate dehydrogenase, FBP, a reducing agent (e.g., dithiothreitol), a detergent (e.g., Brij 35), glycerol, and a solvent (e.g., DMSO). Exemplary reaction conditions are found in Table 1.

TABLE 1

| Component of Reaction Condition | Amount in Activation Assay |
|---|---|
| ADP | 0.1-5.0 mM |
| Phosphoenolpyruvate | 0.1-5.0 mM |
| NADH | 10-1000 µM |
| Lactate dehydrogenase | 0.1-10 units |
| Fructose-1,6-bisphosphate | 0 |
| DTT | 0.1-50 mM |
| Brij 35 | 0.01-1% |
| Glycerol | 0.1-10% |
| Pyruvate Kinase M2 (used for screen) | 1-100 pg |
| DMSO | 1-10% |

Compounds useful as PKM2 activators are those that demonstrate specificity and activation of PKM2 enzyme in the absence of FBP to a level greater than that of 10, 15, 20, 25, 30, 35, 40, 45, 50, 55, 60, 65, 70, 75, 80, 85, 90, 95, 99, or 100% in the presence of FBP. Furthermore, compounds can be evaluated in the presence or absence of a phosphotyrosine peptide. Phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation even in the presence of a phosphotyrosine peptide will lead to the loss of allosteric control of PKM2 needed for shunting the biochemical intermediates from glycolysis into biosynthesis of other intermediates. This, in turn, will lead to inhibition of growth of cancer cells, activated immune cells and fat cells.

Methods of Treatment

In one embodiment, provided is a method for treating or preventing a disease, condition or disorder as described herein (e.g., treating) comprising administering a compound, a pharmaceutically acceptable salt of a compound or pharmaceutical composition comprising a compound described herein (e.g., a compound of formula (I), (II), or in FIG. 1).

The compounds and compositions described herein can be administered to cells in culture, e.g., in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, a second therapeutic agent to a subject, e.g., a patient, or application or administration of the compound to an isolated tissue or cell, e.g., cell line, from a subject, e.g., a patient, who has a disorder (e.g., a disorder as described herein), a symptom of a disorder, with the purpose to cure, heal, alleviate, relieve, alter, remedy, ameliorate, improve or affect the disorder, or one or more symptoms of the disorder.

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, the term "prevent" is defined as the application or administration of a compound, alone or in combination with, a second therapeutic agent to a subject, e.g., a patient, or application or administration of the compound to an isolated tissue or cell, e.g., cell line, from a subject, e.g., a patient, who has a predisposition toward a disorder, with the purpose to prevent the occurrence of at least one symptom of the disorder or to delay onset of at least one symptom of the disorder).

As used herein, an amount of a compound effective to prevent a disorder, or a "a prophylactically effective amount" of the compound refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders (e.g., tumors arising from prostate, colon, lung, breast and liver origin), hematopoietic neoplastic disorders, e.g., leukemias, metastatic tumors. Prevalent cancers include: breast, prostate, colon, lung, liver, and pancreatic cancers. Treatment with the compound may be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Without being bound by theory, applicants believe that altered PKM2 levels characterize a subset of all types of cancers, without regard to their cellular nature or location in the body. Thus, the compounds and methods disclosed herein are useful to treat any type of cancer that is characterized by altered PKM2 levels.

Cancer Combination Therapies

In some embodiments, a compound described herein is administered together with one or more additional cancer treatments. Exemplary cancer treatments include, for example: chemotherapy, targeted therapies such as antibody therapies, immunotherapy, and hormonal therapy. Examples of each of these treatments are provided below.

Chemotherapy

In some embodiments, a compound described herein is administered with one or more chemotherapies. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, toposimerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, endamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Satraplatin, Streptozocin, Talaporfin, Tegafur-uracil, Temoporfin, Temozolomide, Teniposide, Tesetaxel, Testolactone, Tetranitrate, Thiotepa, Tiazofurin, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted Therapy

In some embodiments, a compound described herein is administered with one or more targeted therapies. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary anbibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Immunotherapy

In some embodiments, a compound described herein is administered with one or more immunotherapies. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal Therapy

In some embodiments, a compound described herein is administered with one or more hormonal therapies. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Obesity and Fat Disorders

A compound or composition described herein can be used to treat or prevent obesity, e.g., in a human subject, e.g., a child or adult subject. "Obesity" refers to a condition in which a subject has a body mass index of greater than or equal to 30. Many compounds described herein can be used to treat or prevent an over-weight condition. "Over-weight" refers to a condition in which a subject has a body mass index of greater or equal to 25.0. The body mass index (BMI) and other definitions are according to the "NIH Clinical Guidelines on the Identification and Evaluation, and Treatment of Over-weight and Obesity in Adults" (1998). Treatment with the compound may be in an amount effective to alter the weight of the subject, e.g., by at least 2, 5, 7, 10, 12, 15, 20, 25, 30, 25, 40, 45, 50, or 55%. Treatment with a compound may be in an amount effective to reduce the body mass index of the subject, e.g., to less than 30, 28, 27, 25, 22, 20, or 18. The compounds can be used to treat or prevent aberrant or inappropriate weight gain, metabolic rate, or fat deposition, e.g., anorexia, bulimia, obesity, diabetes, or hyperlipidemia (e.g., elevated triglycerides and/or elevated cholesterol), as well as disorders of fat or lipid metabolism.

A compound or composition described herein can be administered to treat obesity associated with Prader-Willi Syndrome (PWS). PWS is a genetic disorder associated with obesity (e.g., morbid obesity).

A compound or composition described herein can be used to reduce body fat, prevent increased body fat, reduce cholesterol (e.g., total cholesterol and/or ratios of total cholesterol to HDL cholesterol), and/or reduce appetite in individuals having PWS associated obesity, and/or reduce comorbidities such as diabetes, cardiovascular disease, and stroke.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound provided herewith, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions provided herewith include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions provided herewith may be administered orally, parenterally, by inhalation spray, topically, rectally, nasally, buccally, vaginally or via an implanted reservoir, preferably by oral administration or administration by injection. The pharmaceutical compositions provided herewith may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions provided herewith may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions provided herewith may also be administered in the form of suppositories for rectal administration. These compositions can be prepared by mixing a compound provided herewith with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions provided herewith is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds provided herewith include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions provided herewith may also be topically applied to the lower intestinal tract by rectal suppository formulation or in a suitable enema formulation. Topically-transdermal patches are also included.

The pharmaceutical compositions provided herewith may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions provided herewith comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds provided herewith. Alternatively, those agents may be part of a single dosage form, mixed together with the compounds provided herewith in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions provided herewith will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination provided herewith may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Patient Selection and Monitoring

The compounds described herein can modulate PKM2. Accordingly, a patient and/or subject can be selected for treatment using a compound described herein by first evaluating the patient and/or subject to determine whether the subject is in need of modulation of PKM2, and if the subject is determined to be in need of modulation of PKM2, then administering to the subject a compound described herein.

A subject can be evaluated as being in need of modulation of PKM2 using methods known in the art, e.g., by measuring the presence and/or activity of PKM2 in the patient. In some embodiments, the activity and/or level of PKM2 is evaluated in the cancer.

A patient receiving a compound described herein can be monitored, for example, for improvement in the condition and/or adverse effects. Improvement of a patient's condition can be evaluated, for example, by monitoring the growth, absence of growth, or regression of the cancer (e.g., a tumor). In some embodiments, the patient is evaluated using a radiological assay or evaluation of hemolytic parameters.

EXAMPLES

Example 1

Synthesis of Compounds of Formula II, Wherein $R^{1a}$ is Benzyl $R^{1b}$ and is Hydroxyl or Methoxy Compounds of Formula II, wherein $R^{1a}$ is benzyl $R^{1b}$ and is hydroxyl or methoxy are produced by Scheme 1 as follows:

Scheme 1:

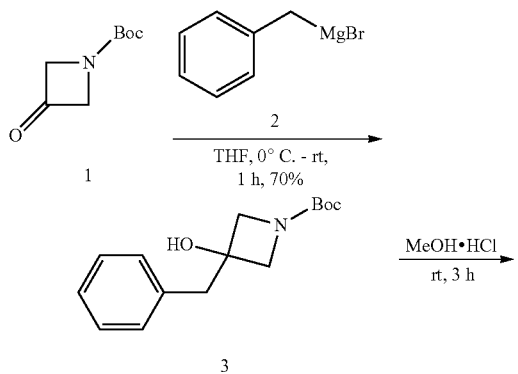

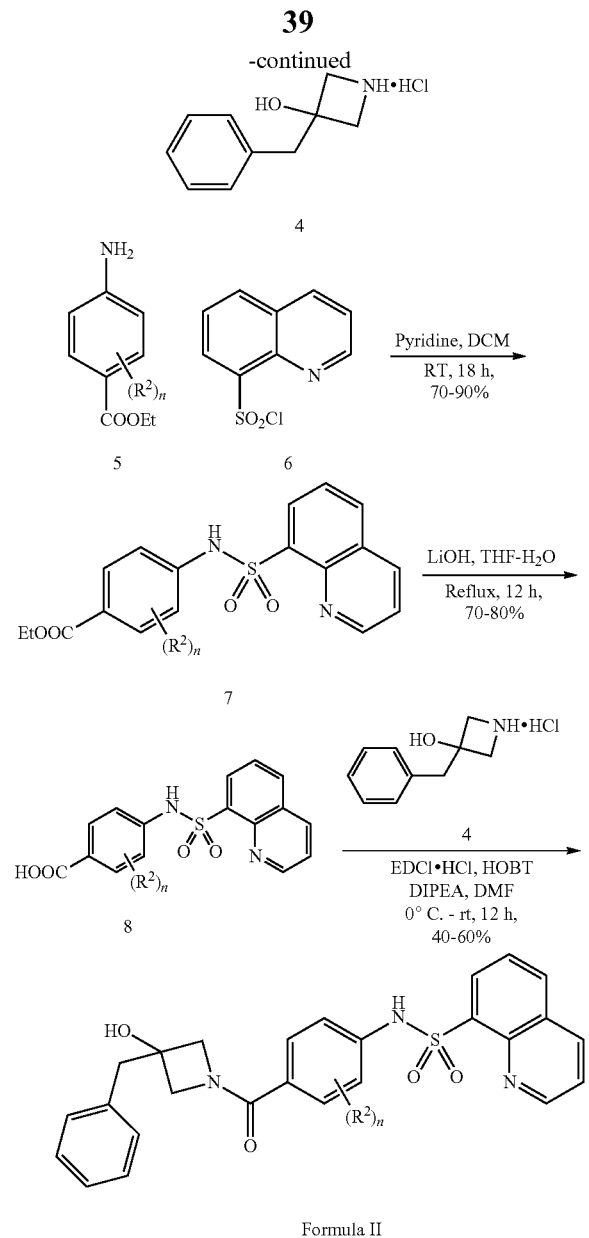

Procedure for Preparation of 3-benzylazetidin-3-ol hydrochloride (4)

tert-butyl 3-benzyl-3-hydroxyazetidine-1-carboxylate 3 (2.0 gm, 7.59 mmol) was taken into a round bottomed flask and was added methanolic-HCl (25 mL, 20%) and was stirred for 3 h at room temperature. After completion of the reaction (monitored by TLC), the solvent was removed under vacuum to get a white solid as a crude product. The crude product was washed with ethyl acetate repeatedly and then dried well to obtain compound 4 as a white solid (1.36 gm, 90%) which was used without further purification.

General Procedure for Preparation of Compound 7

To stirred a solution of amine 5 (30.16 mmol) in a 1:1 mixture of DCM-pyridine (50+50 ml) was added quinoline-8-sulfonyl chloride (6) (8.24 g, 36.19 mmol) under nitrogen atmosphere. The resultant solution was stirred overnight at room temperature. On completion of the reaction (monitored by TLC), the reaction mixture was diluted with dichloromethane (150 ml), washed with water (3×50 mL), 1N HCl solution (3×50 ml) and brine (50 ml). The organic extracts were dried over anhydrous sodium sulfate, filtered and concentrated under vacuum to obtain the crude product. Crude product was co-distilled with toluene to remove the remnants of pyridine and dried to get ester (7) (70-90%) as an off-white solid. This product was used as such for the next step without further purification.

General Procedure for Preparation of Compound 8

A stirred solution of ester 7 (10.05 mmol) in a mixture of THF-water (50+50 ml) was added LiOH (2.11 g, 50.25 mmol) and the resultant solution was refluxed overnight. After completion of the reaction (monitored by TLC), the reaction mixture was extracted with ethyl acetate (3×50 ml) and then acidified with dilute HCl. The resultant suspension was filtered and residue was co-distilled with toluene. The product was then dried under vacuum to get carboxylic acid 8 (70-80%) as an off-white solid.

Procedure for Preparation of tert-butyl 3-benzyl-3-hydroxyazetidine-1-carboxylate (3)

1-Boc-3-azetidinone (1) (2.0 gm, 11.68 mmol) was dissolved in dry THF (20 ml) under nitrogen and cooled to 0° C. Then the solution was added 2.0 M solution of Benzyl magnesium bromide (2) in THF (8.76 ml, 17.52 mmol) under nitrogen atmosphere. The reaction mixture was then allowed to warm to room temperature and stirred for 1 h. The reaction completion was monitored by TLC. The reaction was quenched by the addition of saturated ammonium chloride solution and extracted ethyl acetate. The organic layer was dried over anhydrous sodium sulfate, filtered and concentrated under vacuum. Crude product was then purified by column chromatography to give compound 3 (2.15 gm, 70%). $^1$H NMR (400 MHz, DMSOd$_6$) δ: 1.40 (s, 9H), 2.25 (s, 2H), 4.00 (d, 2H), 4.35 (d, 2H), 6.05 (s, 1H), 7.18 (m, 3H), 7.25 (d, 2H); MS: m/z 263.90 (M+1)$^+$.

General Procedure for Compounds of Formula II, Wherein $R^{1a}$ is Benzyl $R^{1b}$ and is Hydroxyl or Methoxy To a stirred solution of the carboxylic acid 8 (0.61 mmol) in DMF at 0° C. under nitrogen atmosphere, EDCI (0.129 gm, 0.671 mmol), HOBt (0.91 gm, 0.671 mmol) and DIPEA (0.31 ml, 1.83 mmol) were added and the resultant solution was stirred at room temperature for 30 min. Amine hydrochloride 4 (0.61 mmol) was then added at 0° C. and stirred overnight at room temperature. After completion of the reaction (monitored by TLC), the reaction mixture was poured into 1.0 M HCl and extracted with EtOAc. The organic layer was washed with sat. aq. NaHCO$_3$, dried over NaSO$_4$ and filtered. The solvent was removed by rotary evaporation and the product was isolated by chromatography on silica gel (60-120 silica gel, 2% MeOH-DCM) or preparative HPLC to yield amide final compound (40-60%) as an off-white solid.

Compound 101: N-(4-(3-benzyl-3-hydroxyazetidine-1-carbonyl)phenyl)quinoline-8-sulfonamide

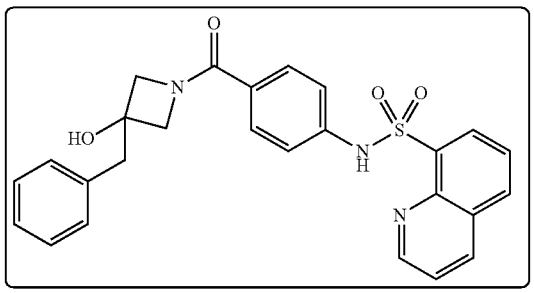 [SMILES: O=C(c1ccc(NS(=O)(=O)c2cccc3cccnc23)cc1)N1CC(O)(Cc2ccccc2)C1]

¹H NMR (400 MHz, DMSOd₆) δ: 2.2 (dd, 3H), 4.1-4.2 (dd, 2H), 4.5 (d, 1H), 4.8 (d, 1H), 6.1 (s, 1H), 7.16-7.4 (m, 5H), 7.37-7.57 (m, 3H), 7.79-7.84 (m, 2H), 8.2-8.40 (m, 3H), 9.10 (d, 1H), 10.5 (s, 1H); HPLC purity: 96.0%; MS: m/z 474.0 (M+1)+.

Compound 105: N-(4-(3-benzyl-3-methoxyazetidine-1-carbonyl)phenyl)quinoline-8-sulfonamide

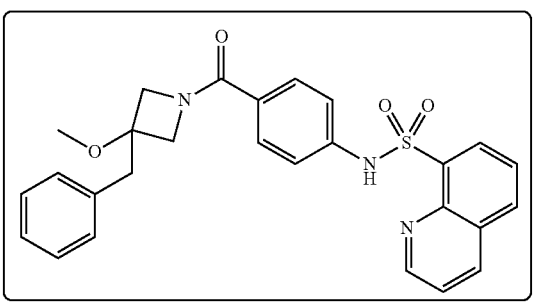 [SMILES: COC1(Cc2ccccc2)CN(C(=O)c2ccc(NS(=O)(=O)c3cccc4cccnc34)cc2)C1]

¹H NMR (400 MHz, DMSOd₆) δ: 3.8 (s, 3H), 3.9 (s, 2H), 4.1 (s, 2H), 7.16-7.4 (m, 5H), 7.37-7.57 (m, 3H), 7.79-7.84 (m, 2H), 8.2-8.40 (m, 3H), 9.10 (d, 1H), 10.5 (s, 1H); HPLC purity: 97.0%; MS: m/z 488.1 (M+1)⁺.

Compound 131: N-(4-(3-benzyl-3-hydroxyazetidine-1-carbonyl)-2-methylphenyl) quinoline-8-sulfonamide

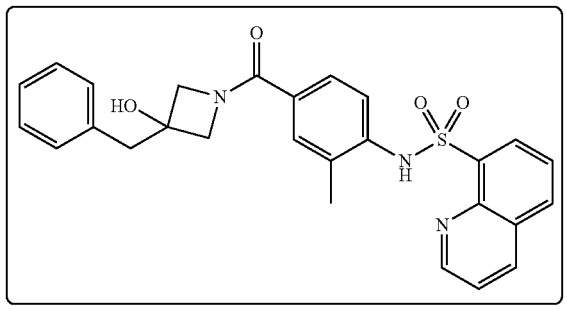 [SMILES: Cc1cc(C(=O)N2CC(O)(Cc3ccccc3)C2)ccc1NS(=O)(=O)c1cccc2cccnc12]

¹H NMR (400 MHz, DMSOd₆) δ: 2.1 (s, 3H), 2.2 (s, 2H), 2.6 (s, 2H), 2.7 (s, 2H), 7.16-7.4 (m, 5H), 7.37-7.57 (m, 3H), 7.79-7.84 (m, 2H), 8.2-8.40 (m, 3H), 9.10 (d, 1H), 10.5 (s, 1H); HPLC purity: 96.9%; MS: m/z 488.1 (M+1)⁺.

Compound 130: N-(4-(3-benzyl-3-hydroxyazetidine-1-carbonyl)-3-methoxyphenyl)quinoline-8-sulfonamide

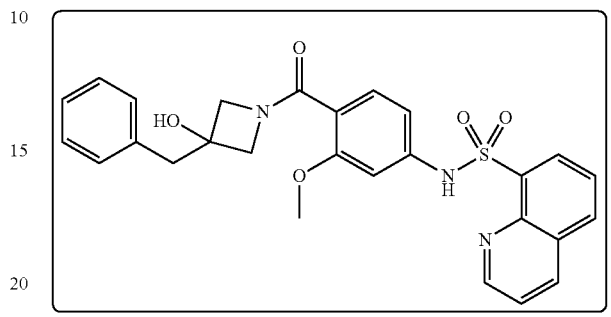

¹H NMR (400 MHz, DMSOd₆) δ: 2.2 (s, 2H), 2.6 (s, 2H), 2.7 (s, 2H), 3.9 (s, 3H), 7.16-7.4 (m, 5H), 7.37-7.57 (m, 3H), 7.79-7.84 (m, 2H), 8.2-8.40 (m, 3H), 9.10 (d, 1H), 10.5 (s, 1H); HPLC purity: 96.9%; MS: m/z 504.2 (M+1)⁺.

Example 2

Synthesis of Compounds of Formula II Wherein $R^{1a}$ is H and $R^{1b}$ is —N(CH₃)-Benzyl or —NH-Benzyl Compounds of Formula II wherein $R^{1a}$ is H and $R^{1b}$ is —N(CH₃)-benzyl or —NH-benzyl are produced according to Scheme 2:

Scheme 2:

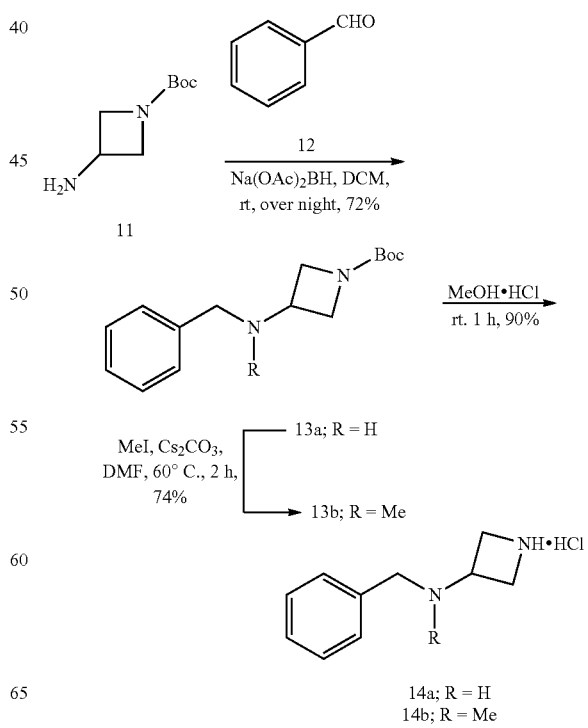

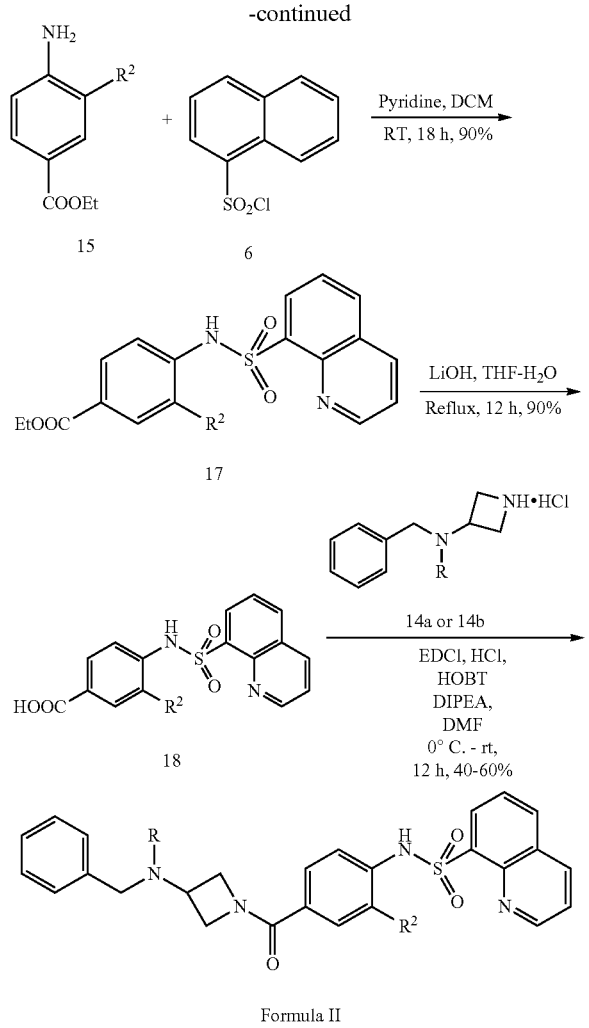

Formula II

Procedure for Preparation of tert-butyl 3-(benzylamino)azetidine-1-carboxylate (13a)

1-Boc-3-aminoazetidine (11) (2.2 gm, 12.78 mmol) was dissolved in DCM (20 ml) under nitrogen and cooled to 0° C. Then the solution was added benzaldehyde (12; 1.35 gm, 12.78 mmol) followed by sodium triacetoxyborohydride (8.13 gm, 38.34 mmol) under nitrogen atmosphere. The reaction mixture was then allowed to warm to room temperature and stirred over night. The reaction's completion was monitored by TLC. After completion of the reaction it was quenched by the addition of water (5 ml) and extracted with DCM. The organic layer was washed with brine (10 ml), dried over anhydrous sodium sulfate, filtered and concentrated under vacuum. Crude product was then purified by column chromatography to give compound (13a) (2.46 gm, 72%). $^1$H NMR (400 MHz, CDCl$_3$) δ: 1.40 (s, 9H), 3.60 (m, 3H), 3.73 (s, 2H), 4.05 (m, 2H), 7.3 (m, 5H); MS: m/z 263.20 (M+1)$^+$.

Procedure for Preparation of tert-butyl 3-(benzyl(methyl)amino)azetidine-1-carboxylate (13b)

A solution of tert-butyl 3-(benzylamino)azetidine-1-carboxylate (13a) (0.55 gm, 2.09 mmol) in DMF was added methyl iodide (0.26 ml, 4.18 mmol) and cesium carbonate (1.36 gm, 4.18 mmol). The resultant reaction mixture was then warmed to 60° C. and stirred for 2 h. The reaction mixture was then diluted with ethyl acetate (100 ml), washed with water (3×25 ml), brine, dried over sodium sulfate and concentrated under vacuum. The crude product was purified by column chromatography to give compound (13b) (2.46 gm, 72%). $^1$H NMR (400 MHz, CDCl$_3$) δ: 1.40 (s, 9H), 3.40 (m, 5H), 4.00 (m, 2H), 4.20 (m, 2H), 5.2 (m, 1H), 7.50 (m, 3H), 7.70 (d, 2H); MS: m/z 277.10 (M+1)$^+$.

General Procedure for N-Boc Deprotection (14a & 14b)

Amine (13a or 13b) (2.0 gm) was taken into a round bottomed flask and was added methanolic-HCl (25 mL, 20%) and was stirred for 1 h at room temperature. After completion of the reaction (monitored by TLC), the solvent was removed under vacuum to get a white solid as a crude product. The crude product was washed with ethyl acetate repeatedly and then dried well to obtain compound 14a or 14b, respectively as a white solid (90%) and was used further without purification.

General Procedure for Preparation of Compound 17

To stirred a solution of amine 15 (30.16 mmol) in a 1:1 mixture of DCM-pyridine (50+50 ml) was added quinoline-8-sulfonyl chloride (6) (8.24 g, 36.19 mmol) under nitrogen atmosphere. The resultant solution was stirred overnight at room temperature. On completion of the reaction (monitored by TLC), the reaction mixture was diluted with dichloromethane (150 ml), washed with water (3×50 mL), 1N HCl solution (3×50 ml) and brine (50 ml). The organic extracts were dried over anhydrous sodium sulfate, filtered and concentrated under vacuum to obtain the crude product. Crude product was co-distilled with toluene to remove the remnants of pyridine and dried to get ester 17 (70-90%) as an off-white solid. This product was used as such for the next step without further purification.

General Procedure for Preparation of Compound 18

A stirred solution of ester 17 (10.05 mmol) in a mixture of THF-water (50+50 ml) was added LiOH (2.11 g, 50.25 mmol) and the resultant solution was refluxed overnight. After completion of the reaction (monitored by TLC), the reaction mixture was extracted with ethyl acetate (3×50 ml) and then acidified with dilute HCl. The resultant suspension was filtered and residue was co-distilled with toluene. The product was then dried under vacuum to get carboxylic acid 18 (70-80%) as an off-white solid.

General Procedure for Compounds of Formula II Wherein R$^{1a}$ is H and R$^{1b}$ is —N(CH$_3$)-Benzyl or —NH-Benzyl To a stirred solution of the carboxylic acid 18 (0.61 mmol) in DMF at 0° C. under nitrogen atmosphere, EDCI (0.129 gm, 0.671 mmol), HOBt (0.91 gm, 0.671 mmol) and DIPEA (0.31 ml, 1.83 mmol) were added and the resultant solution was stirred at room temperature for 30 min. Amine hydrochloride 14a or 14b) (0.61 mmol) was then added at 0° C. and stirred overnight at room temperature. After completion of the reaction (monitored by TLC), the reaction mixture was poured into 1.0 M HCl and extracted with EtOAc. The organic layer was washed with sat. aq. NaHCO$_3$, dried over NaSO$_4$ and filtered. The solvent was removed by rotary evaporation and the product was isolated by chromatography on silica gel (60-120 silica gel, 2% MeOH-DCM) or preparative HPLC to yield final compound (50-60%) as an off-white solid.

Compound 147: N-(4-(3-(benzylamino)azetidine-1-carbonyl)phenyl)quinoline-8-sulfonamide

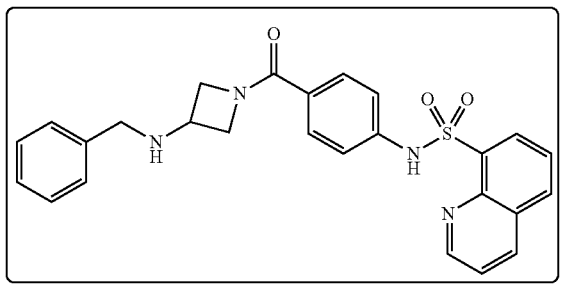 [SMILES: O=C(c1ccc(NS(=O)(=O)c2cccc3cccnc23)cc1)N1CC(NCc2ccccc2)C1]

$^1$H NMR (400 MHz, DMSOd$_6$) δ: 1.8-1.85 (m, 1H), 2.2 (dd, 2H), 2.6 (dd, 2H), 2.7 (s, 2H), 7.16-7.4 (m, 5H), 7.37-7.57 (m, 4H), 7.79-7.84 (m, 2H), 8.2-8.40 (m, 2H), 9.10 (d, 1H), 10.4 (s, 1H); HPLC purity: 96.9%; MS: m/z 473.1 (M+1)$^+$.

Compound 109: N-(4-(3-(benzyl(methyl)amino) azetidine-1-carbonyl)-2-methylphenyl)quinoline-8-sulfonamide

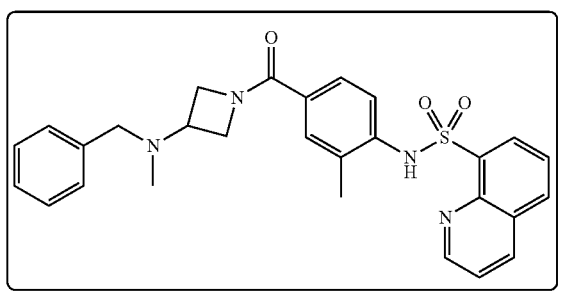 [SMILES: Cc1cc(C(=O)N2CC(N(C)Cc3ccccc3)C2)ccc1NS(=O)(=O)c1cccc2cccnc12]

$^1$H NMR (400 MHz, DMSOd$_6$) δ: 1.8-1.85 (m, 1H), 2.1 (s, 3H), 2.2 (dd, 2H), 2.6 (dd, 2H), 2.7 (s, 2H), 3.1 (s, 3H), 7.16-7.4 (m, 5H), 7.37-7.57 (m, 3H), 7.79-7.84 (m, 2H), 8.2-8.40 (m, 2H), 9.10 (d, 1H), 10.4 (s, 1H); HPLC purity: 96.9%; MS: m/z 488.1 (M+1)$^+$.

Example 3

Synthesis of Compounds of Formula II Wherein R$^{1a}$ is Hydrogen and R$^{1b}$ is —O-Benzyl Compounds of Formula II wherein R$^{1a}$ is hydrogen and R$^{1b}$ is —O-benzyl are prepared according to Scheme 3:

Scheme 3:

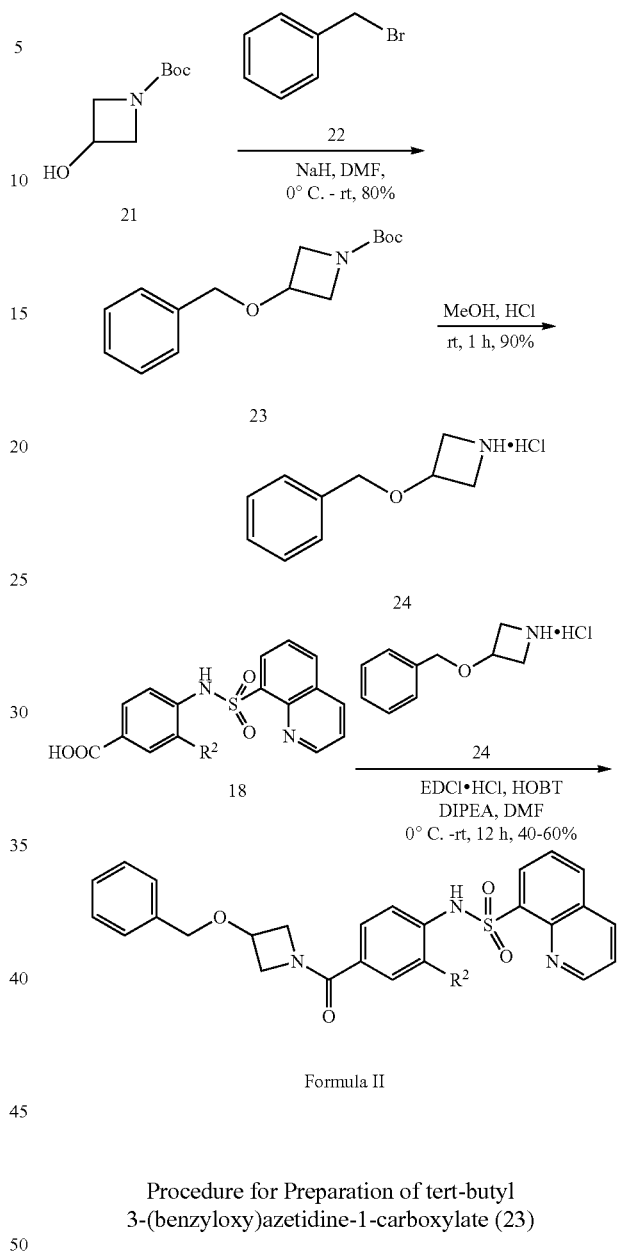

Formula II

Procedure for Preparation of tert-butyl 3-(benzyloxy)azetidine-1-carboxylate (23)

tert-butyl 3-hydroxyazetidine-1-carboxylate (21) (1 gm, 5.77 mmol) was dissolved in dry DMF (15 ml) and was cooled to 0° C. under nitrogen and was added sodium hydride (0.35 gm, 8.66 mmol). The reaction mixture was allowed to stir at room temperature for 30 min and was added benzylbromide (22; 1.08 gm, 6.35 mmol) at 0° C. The reaction mixture was then allowed warm to room temperature and stirred for 2 h. After completion of the reaction it was quenched by the addition of sat. ammonium chloride solution and extracted with ether. The organic layer was then dried over sodium sulfate and concentrated under vacuum. The crude product was purified column chromatography to yield compound 23 (1.21 gm, 80%).

$^1$H NMR ((400 MHz, DMSOd$_6$) δ: 1.4 (s, 9H), 3.65 (m, 2H), 4.00 (t, 2H), 4.30 (m, 1H), 4.40 (s, 2H), 7.35 (m, 5H); MS: m/z 264.20 (M+1)$^+$.

Procedure for Preparation of 3-(benzyloxy)azetidine hydrochloride 24 tert-butyl 3-(benzyloxy)azetidine-1-carboxylate 23 (1.0 gm) was taken into a round bottomed flask and was added methanolic-HCl (15 mL, 20%) and was stirred for 1 h at room temperature. After completion of the reaction (monitored by TLC), the solvent was removed under vacuum to get a white solid as a crude product. The crude product was washed with ethyl acetate repeatedly and then dried well to obtain compound 24 as a white solid (92%) and was used further without purification.

General Procedure for Compound of Formula II Wherein $R^{1a}$ is Hydrogen and $R^{1b}$ is —O-Benzyl To a stirred solution of the carboxylic acid 18 (0.61 mmol) (prepared as in Example 2) in DMF at 0° C. under nitrogen atmosphere, EDCI (0.129 gm, 0.671 mmol), HOBt (0.91 gm, 0.671 mmol) and DIPEA (0.31 ml, 1.83 mmol) were added and the resultant solution was stirred at room temperature for 30 min. Amine hydrochloride 24 (0.61 mmol) was then added at 0° C. and stirred overnight at room temperature. After completion of the reaction (monitored by TLC), the reaction mixture was poured into 1.0 M HCl and extracted with EtOAc. The organic layer was washed with sat. aq. NaHCO₃, dried over NaSO₄ and filtered. The solvent was removed by rotary evaporation and the product was isolated by chromatography on silica gel (60-120 silica gel, 2% MeOH-DCM) or preparative HPLC to yield final compound (50-60%) as an off-white solid.

Compound 108: N-(4-(3-(benzyloxy)azetidine-1-carbonyl)phenyl)quinoline-8-sulfonamide

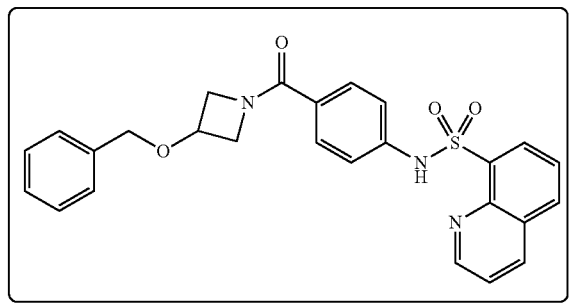 [SMILES: O=C(c1ccc(NS(=O)(=O)c2cccc3cccnc23)cc1)N1CC(OCc2ccccc2)C1]

¹H NMR (400 MHz, DMSOd₆) δ: 2.6 (s, 2H), 2.2 (dd, 2H), 4.1-4.2 (dd, 3H), 7.16-7.4 (m, 5H), 7.37-7.57 (m, 3H), 7.79-7.84 (m, 2H), 8.2-8.40 (m, 3H), 9.10 (d, 1H), 10.5 (s, 1H); HPLC purity: 98.9%; MS: m/z 474.1 (M+1)⁺.

Compound 120: N-(4-(3-(benzyloxy)azetidine-1-carbonyl)-2-methylphenyl)quinoline-8-sulfonamide

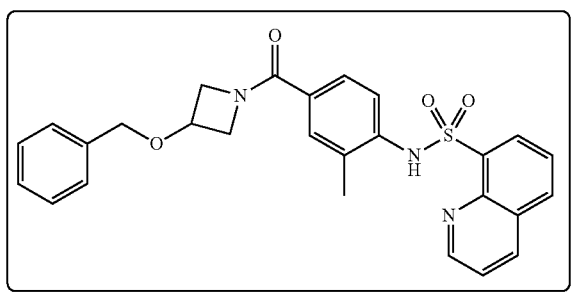 [SMILES: Cc1cc(C(=O)N2CC(OCc3ccccc3)C2)ccc1NS(=O)(=O)c1cccc2cccnc12]

¹H NMR (400 MHz, DMSOd₆) δ: 2.2 (s, 3H), 2.6 (s, 2H), 2.2 (dd, 2H), 4.1-4.2 (dd, 3H), 7.16-7.4 (m, 5H), 7.37-7.57 (m, 3H), 7.79-7.84 (m, 2H), 8.2-8.40 (m, 3H), 9.10 (d, 1H), 10.5 (s, 1H); HPLC purity: 98.5%; MS: m/z 488.3 (M+1)⁺.

Example 4

Syntheses of Compounds of Formula II Wherein $R^{1a}$ is Hydrogen and $R^{1b}$ is —NH—C(O)—$R^a$ Compounds of Formula II wherein $R^{1a}$ is Hydrogen and $R^{1b}$ is —NH—C(O)—Ar are prepared as set forth in Scheme 4:

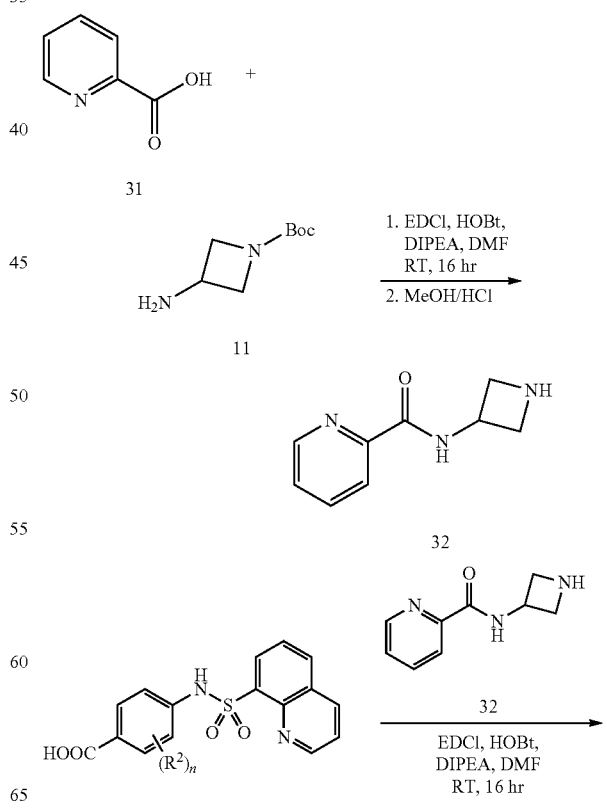

-continued

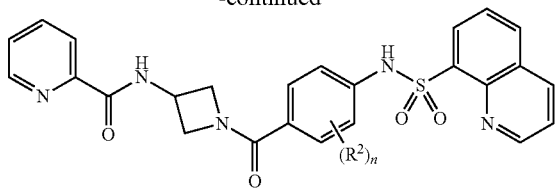

Formula II

General Procedure for the Synthesis of Urea 32

EDCI (3.8 g, 19.8 mmol) and HOBT (2.67 g, 19.8 mmol) were added to a stirred solution of the acid 31 (19.8 mmol) in anhydrous DMF. The temperature of the mixture was reduced to 0° C., at which time DIPEA (11 ml, 59.45 mmol) was added under nitrogen atmosphere and the resultant solution (or suspension) was stirred at room temperature for 30 min. 3-amino-1-Boc azetidine (11; 19.8 mmol) was then added at 0° C. The reaction mixture was then brought to room temperature and stirred overnight. After completion of the reaction, the reaction mixture was diluted with water and extracted with ethyl acetate (3×70 ml). The organic layer was washed with water (3×50 ml), dried over anhydrous sodium sulfate, filtered and concentrated over the rotary evaporator to get the crude product. Crude product was purified by column chromatography (60-120 silica gel, 2% MeOH-DCM) to get pure product, Boc-32 (81%; not shown) as an off-white solid, which was subjected to the treatment with methanolic HCl (100 ml) for 2 hr at RT. After the complete cleavage of Boc-group, the solvent was removed under low pressure, to give the crude product as an HCl salt. The aqueous solution of the salt was washed with diethylether and basified with NaHCO$_3$ (pH 10). The desired product was then partitioned into ethyl acetate, dried with anhydrous Na$_2$SO$_4$ and the solvent removed under low pressure to get the free amine 32 as off white solid (95%).

General Procedure for the Synthesis of Amides 22a-c

EDCI (48 mg, 0.2525 mmol) and HOBT (34 mg, 0.2525 mmol) were added to a stirred solution of 8 (0.2525 mmol; prepared as in Example 1) in anhydrous DMF. The temperature of the mixture was reduced to 0° C., at which time DIPEA (139 µl, 0.7575 mmol) was added under nitrogen atmosphere and the resultant solution (or suspension) was stirred at room temperature for 30 min. Amine 32 (0.2525 mmol) was then added at 0° C. The reaction mixture was then brought to room temperature and stirred overnight. After completion of the reaction, the reaction mixture was diluted with water and extracted with ethyl acetate (3×15 ml). The organic layer was washed with water (3×10 ml), dried over anhydrous sodium sulfate, filtered and concentrated over the rotary evaporator to get the crude product. Crude product was purified by either by silica column chromatography or preparative HPLC to obtain the pure products in 45-65% yields.

Compound 103: N-(1-(3-Methyl-4-(quinoline-8-sulfonamido)benzoyl)azetidin-3-yl)picolinamide

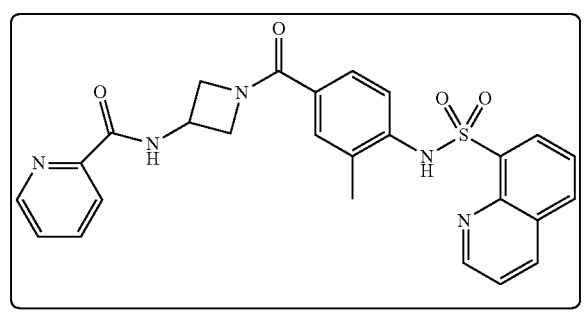 [SMILES: Cc1cc(C(=O)N2CC(NC(=O)c3ccccn3)C2)ccc1NS(=O)(=O)c1cccc2cccnc12]

$^1$H NMR (400 MHz, CDCl$_3$) δ: 2.1 (s, 3H), 4.2 (d, 2H), 4.4 (d, 2H), 5.2 (m, 1H), 7.0-8.0 (m, 8H), 8.0-8.4 (m, 4H), 9.1 (m, 1H); HPLC Purity: 97.5%; LCMS, m/z found 502.1 (M+1)$^+$.

Compound 111: N-(1-(4-(Quinoline-8-sulfonamido)benzoyl)azetidin-3-yl)picolinamide

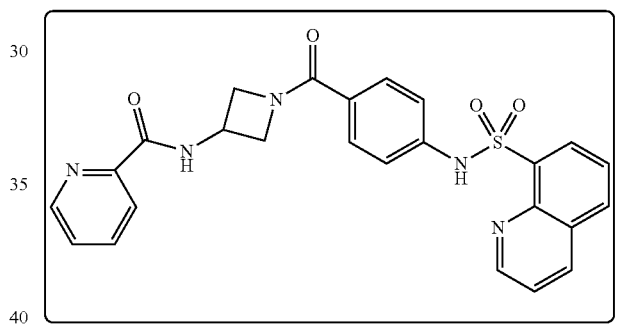

$^1$H NMR (400 MHz, CDCl$_3$) δ: 4.2 (d, 2H), 4.4 (d, 2H), 5.2 (m, 1H), 7.0-8.0 (m, 8H), 8.0-8.4 (m, 5H), 9.1 (m, 1H); HPLC Purity: 98.6%; LCMS, m/z found 488.2 (M+1)$^+$.

Compound 121: N-(1-(3-Fluoro-4-(quinoline-8-sulfonamido)benzoyl)azetidin-3-yl)picolinamide (22c)

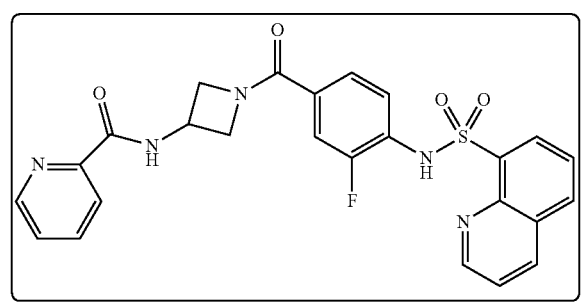 [SMILES: O=C(NC1CN(C(=O)c2ccc(NS(=O)(=O)c3cccc4cccnc34)c(F)c2)C1)c1ccccn1]

$^1$H NMR (400 MHz, CDCl$_3$) δ: 4.2 (d, 2H), 4.4 (d, 2H), 5.2 (m, 1H), 7.0-8.0 (m, 8H), 8.0-8.4 (m, 4H), 9.1 (m, 1H); HPLC Purity: 99.0%; LCMS, m/z found 506.3 (M+1)$^+$.

Example 5

Syntheses of Compounds of Formula II, Wherein $R^{1a}$ is Hydrogen and $R^{1b}$ is —NH—C(O)—NH—$R^a$ Compounds of Formula II, wherein $R^{1a}$ is hydrogen and $R^{1b}$ is —NH—C(O)—NH—$R^a$ are prepared according to Scheme 5:

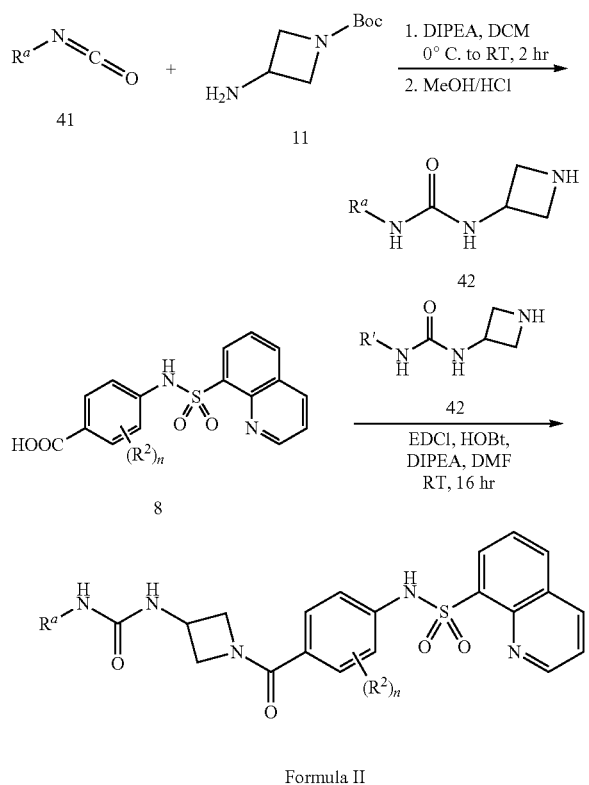

Formula II

General Procedure for the Synthesis of Urea 42

To a stirred solution of 3-amino-1-Boc azetidine (11; 100 mg, 0.5813 mmol) and DIPEA (160 mg, 0.8719 mmol) in DCM (2 ml) at 0° C. was slowly added isocyanate 41. The resulting mixture was stirred for 2 hr at RT. After completion of the reaction, the reaction mixture was dilute with water and the product was extracted in DCM (2×20 ml). The organic layer was washed with water (2×15 ml), dried over anhydrous sodium sulfate, filtered and concentrated over the rotary evaporator to get the crude product. Crude product was purified by column chromatography (60-120 silica gel, 2% MeOH-DCM) to get pure product, Boc-42 (59%; not shown) as an off-white solid, which was subjected to the treatment with methanolic HCl (10 ml) for 2 hr at RT. After the complete cleavage of Boc-group, the solvent was removed under low pressure, to give the crude product as an HCl salt. The aqueous solution of the salt was washed with diethylether and basified with NaHCO$_3$ (pH 10). The desired product was then partitioned into ethyl acetate, dried over anhydrous Na$_2$SO$_4$ and the solvent removed under low pressure to get the free amine 42 as off white solid (87%).

General Procedure for the Synthesis of Compounds of Formula II, Wherein $R^{1a}$ is Hydrogen and $R^{1b}$ is —NH—C(O)—NH—$R^a$ EDCI (48 mg, 0.2525 mmol) and HOBT (34 mg, 0.2525 mmol) were added to a stirred solution of 8 (0.2525 mmol; prepared as in Example 1) in anhydrous DMF. The temperature of the mixture was reduced to 0° C., at which time DIPEA (139 µl, 0.7575 mmol) was added under nitrogen atmosphere and the resultant solution (or suspension) was stirred at room temperature for 30 min. Amine 42 (0.2525 mmol) was then added at 0° C. The reaction mixture was then brought to room temperature and stirred overnight. After completion of the reaction, the reaction mixture was diluted with water and extracted with ethyl acetate (3×15 ml). The organic layer was washed with water (3×10 ml), dried over anhydrous sodium sulfate, filtered and concentrated over the rotary evaporator to get the crude product. Crude product was purified by either by silica column chromatography or preparative HPLC to obtain the pure products in 53-63% yields.

Compound 139: N-(4-(3-(3-Allylureido)azetidine-1-carbonyl)phenyl)quinoline-8-sulfonamide

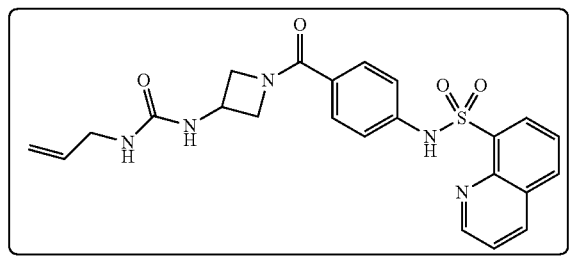 [SMILES: C=CCNC(=O)NC1CN(C(=O)c2ccc(NS(=O)(=O)c3cccc4cccnc34)cc2)C1]

$^1$H NMR (400 MHz, CDCl$_3$) δ: 4.2 (d, 2H), 4.3 (s, 2H), 4.4 (d, 2H), 5.0 (m, 1H), 5.2 (m, 2H), 5.9 (m, 1H), 7.0-8.0 (m, 5H), 8.0-8.4 (m, 4H), 9.1 (m, 1H); HPLC Purity: 97.8%; LCMS, m/z found 484.3 (M+1)$^+$.

Compound 140: N-(4-(3-(3-Allylureido)azetidine-1-carbonyl)-2-methoxyphenyl)quinoline-8-sulfonamide

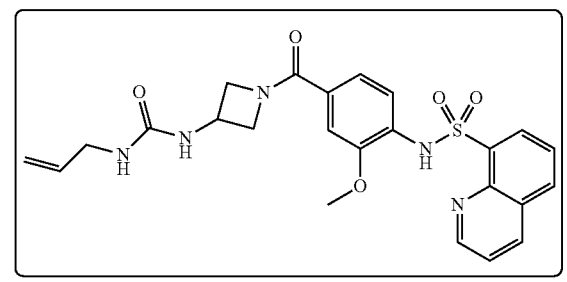 [SMILES: C=CCNC(=O)NC1CN(C(=O)c2ccc(NS(=O)(=O)c3cccc4cccnc34)c(OC)c2)C1]

$^1$H NMR (400 MHz, CDCl$_3$) δ: 3.9 (s, 3H), 4.2 (d, 2H), 4.3 (s, 2H), 4.4 (d, 2H), 5.0 (m, 1H), 5.2 (m, 2H), 5.9 (m, 1H), 7.0-8.0 (m, 4H), 8.0-8.4 (m, 4H), 9.1 (m, 1H); HPLC Purity: 99.1%; LCMS, m/z found 496.2 (M+1)$^+$.

Compound 166: N-(4-(3-(3-Allylureido)azetidine-1-carbonyl)-2-methylphenyl)quinoline-8-sulfonamide

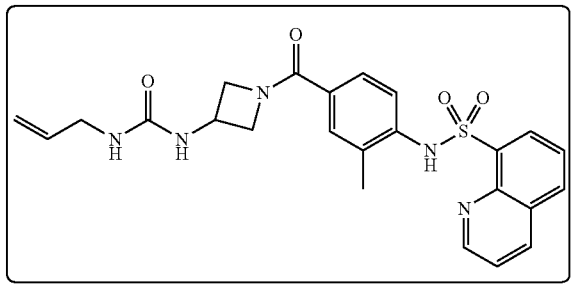 [SMILES: C=CCNC(=O)NC1CN(C(=O)c2ccc(NS(=O)(=O)c3cccc4cccnc34)c(C)c2)C1]

$^1$H NMR (400 MHz, CDCl$_3$) δ: 2.1 (s, 3H), 4.2 (d, 2H), 4.3 (s, 2H), 4.4 (d, 2H), 5.0 (m, 1H), 5.2 (m, 2H), 5.9 (m, 1H), 7.0-8.0 (m, 4H), 8.0-8.4 (m, 4H), 9.1 (m, 1H); HPLC Purity: 98.6%; LCMS, m/z found 480.3 (M+1)$^+$.

Compound 160: N-(4-(3-(3-(Pyridin-2-yl)ureido)azetidine-1-carbonyl)phenyl)quinoline-8-sulfonamide

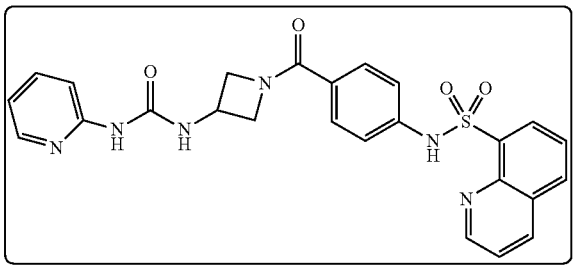 [SMILES: O=C(Nc1ccccn1)NC1CN(C(=O)c2ccc(NS(=O)(=O)c3cccc4cccnc34)cc2)C1]

$^1$H NMR (400 MHz, CDCl$_3$) δ: 4.2 (d, 2H), 4.4 (d, 2H), 5.2 (m, 1H), 7.0-8.0 (m, 8H), 8.0-8.2 (m, 5H), 9.1 (m, 1H); HPLC Purity: 99.2%; LCMS, m/z found 503.1 (M+1)$^+$.

Example 6

Syntheses of Compounds of Formula II Wherein R$^{1a}$ is Hydrogen and R$^{1b}$ is —O—C(O)—R$^a$ Compounds of Formula II wherein R$^{1a}$ is hydrogen and R$^{1b}$ is —O—C(O)—R$^a$ are prepared according to Scheme 6.

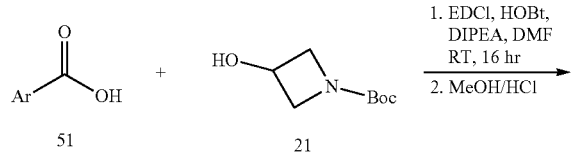

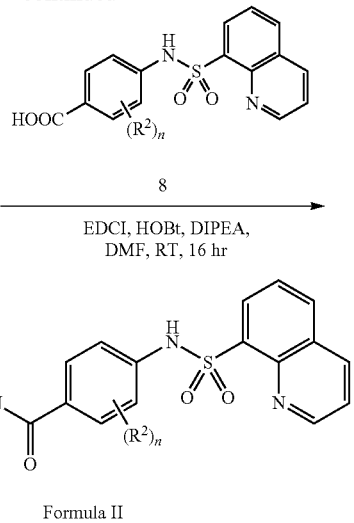

Formula II

General Procedure for the Synthesis of Ester 52

EDCI (48 mg, 0.2525 mmol) and HOBT (34 mg, 0.2525 mmol) were added to a stirred solution of the Ar—COOH (0.2525 mmol) in anhydrous DMF. The temperature of the mixture was reduced to 0° C., at which time DIPEA (139 μl, 0.7575 mmol) was added under nitrogen atmosphere and the resultant solution (or suspension) was stirred at room temperature for 30 min. 3-Hydroxy-1-Boc azetidine 21 (0.2525 mmol) was then added at 0° C. The reaction mixture was then brought to room temperature and stirred overnight. After completion of the reaction, the reaction mixture was diluted with water and extracted with ethyl acetate (3×15 ml). The organic layer was washed with water (3×10 ml), dried over anhydrous sodium sulfate, filtered and concentrated over the rotary evaporator to get crude product. The crude product was purified by column chromatography (60-120 silica gel, 2% MeOH-DCM) to get pure product, Boc-52 (66%; not shown) as an off-white solid, which was subjected to the treatment with methanolic HCl (10 ml) for 2 hr at RT. After the complete cleavage of Boc-group, the solvent was removed under low pressure, to give the crude product as an HCl salt. The aqueous solution of the salt was washed with diethylether and basified with NaHCO$_3$ (pH 10). The desired product was then partitioned into ethyl acetate, dried over anhydrous Na$_2$SO$_4$ and the solvent removed under low pressure to get the free amine 52 as off white solid (83%).

General Procedure for the Synthesis of Compounds of Formula II Wherein R$^{1a}$ is Hydrogen and R$^{1b}$ is —O—C(O)—R$^a$ EDCI (48 mg, 0.2525 mmol) and HOBT (34 mg, 0.2525 mmol) were added to a stirred solution of the carboxylic acid 8 (0.2525 mmol; prepared as in Example 1) in anhydrous DMF. The temperature of the mixture was reduced to 0° C., at which time DIPEA (139 μl, 0.7575 mmol) was added under nitrogen atmosphere and the resultant solution (or suspension) was stirred at room temperature for 30 min. Amine 52 (0.2525 mmol) was then added at 0° C. The reaction mixture was then brought to room temperature and stirred overnight. After completion of the reaction, the reaction mixture was diluted with water and extracted with ethyl acetate (3×15 ml).

The organic layer was washed with water (3×10 ml), dried over anhydrous sodium sulfate, filtered and concentrated over the rotary evaporator to get crude product. Crude product was purified by either by silica column chromatography or preparative HPLC to obtain the pure products in 47-68% yields.

Compound 102: 1-(4-(Quinoline-8-sulfonamido)benzoyl)azetidin-3-yl picolinate

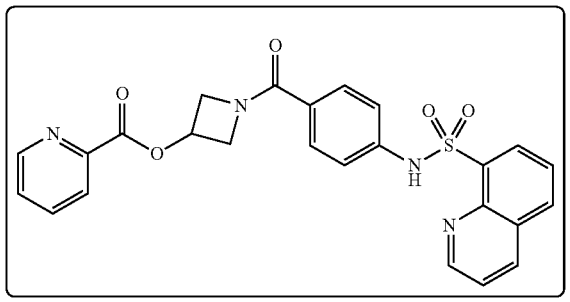 [SMILES: O=C(OC1CN(C(=O)c2ccc(NS(=O)(=O)c3cccc4cccnc34)cc2)C1)c1ccccn1]

$^1$H NMR (400 MHz, CDCl$_3$) δ: 4.2-4.8 (m, 4H), 5.5 (m, 1H), 7.2-7.7 (m, 7H), 8.0-8.7 (m, 6H), 9.1 (m, 1H); HPLC Purity: 91.0%; LCMS, m/z found 489.3 (M+1)$^+$.

Compound 110: 1-(3-Methyl-4-(quinoline-8-sulfonamido)benzoyl)azetidin-3-yl picolinate

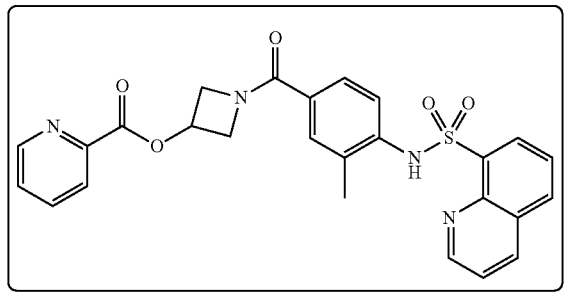 [SMILES: Cc1cc(C(=O)N2CC(OC(=O)c3ccccn3)C2)ccc1NS(=O)(=O)c1cccc2cccnc12]

$^1$H NMR (400 MHz, CDCl$_3$) δ: 2.1 (s, 3H), 4.2-4.8 (m, 4H), 5.5 (m, 1H), 7.2-7.7 (m, 6H), 8.0-8.7 (m, 6H), 9.1 (m, 1H); HPLC Purity: 98.4%; LCMS, m/z found 503.1 (M+1)$^+$.

Compound 123: 1-(4-(Quinoline-8-sulfonamido)benzoyl)azetidin-3-yl 2-phenylacetate

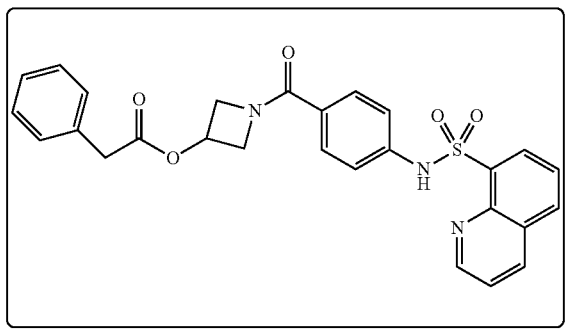 [SMILES: O=C(Cc1ccccc1)OC1CN(C(=O)c2ccc(NS(=O)(=O)c3cccc4cccnc34)cc2)C1]

$^1$H NMR (400 MHz, CDCl$_3$) δ: 3.6 (m, 1H), 4.2 (d, 2H), 4.4-4.6 (d, 2H), 5.3 (m, 2H), 7.2-7.8 (m, 7H), 8.0-8.7 (m, 7H), 9.1 (m, 1H); HPLC Purity: 97.0%; LCMS, m/z found 502.2 (M+1)$^+$.

Compound 124: 1-(3-Fluoro-4-(quinoline-8-sulfonamido)benzoyl)azetidin-3-yl picolinate

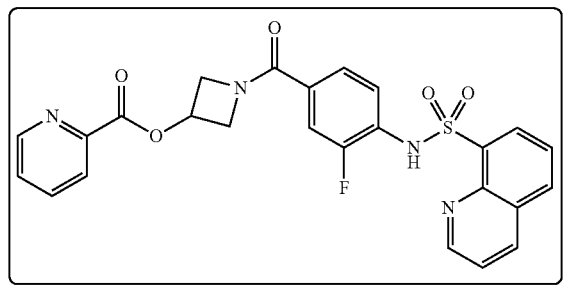 [SMILES: O=C(OC1CN(C(=O)c2ccc(NS(=O)(=O)c3cccc4cccnc34)c(F)c2)C1)c1ccccn1]

$^1$H NMR (400 MHz, CDCl$_3$) δ: 4.2 (d, 2H), 4.6 (d, 2H), 4.7 (m, 1H), 7.2-7.8 (m, 6H), 8.0-8.7 (m, 6H), 9.1 (m, 1H); HPLC Purity: 99.0%; LCMS, m/z found 507.4 (M+1)$^+$.

Example 7

Syntheses of Compounds of Formula II Wherein $R^{1a}$ is Hydrogen and $R^{1b}$ is —O—C(O)—NH—$R^a$ Compounds of Formula II wherein $R^{1a}$ is hydrogen and $R^{1b}$ is —O—C(O)—NH—$R^a$ are prepared according to Scheme 7.

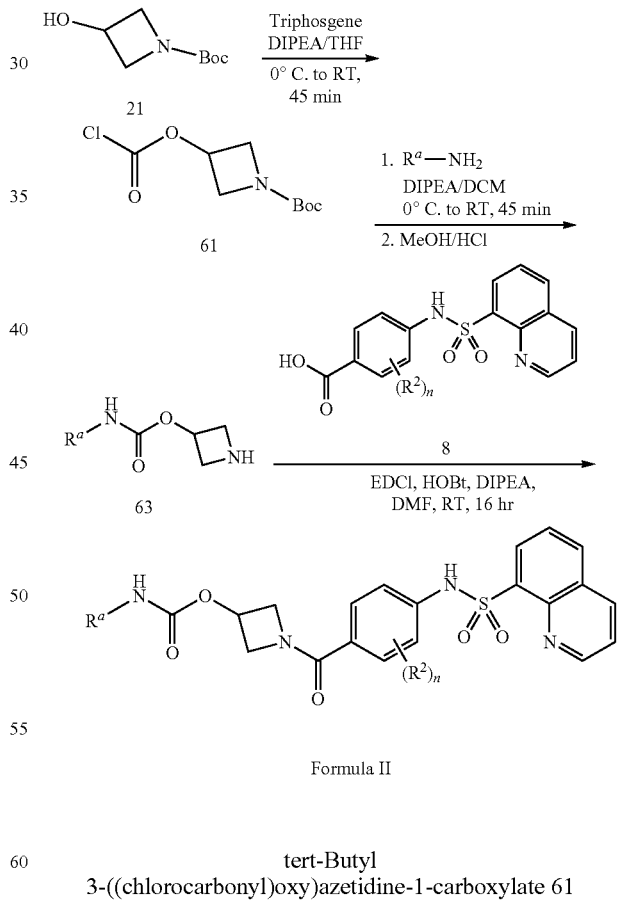

tert-Butyl 3-((chlorocarbonyl)oxy)azetidine-1-carboxylate 61

To a stirred solution of 3-hydroxy-1-Boc azetidine (21; 350 mg, 2.023 mmol) and DIPEA (1.3 ml, 7.080 mmol) in THF (5 ml) at 0° C. was slowly added triphosgene (898 mg, 3.034 mmol). The resulting mixture was stirred for 2 hr at RT. After completion of the reaction, the reaction mixture was filtered and washed with fresh THF to get rid of inorganic salts. The filtrate was concentrated under reduced pressure to get crude product 61 in 55% yield. The crude product, thus obtained, was immediately used for the next reaction.

General Procedure for the Synthesis of Carbamate 63

To a stirred solution of amine 62 (100 mg, 1.694 mmol) and DIPEA (0.47 ml, 2.541 mmol) in DCM (2 ml) at 0° C. was slowly added a solution of compound 61 (477 mg, 2.033 mmol) in DCM (1 ml). The resulting mixture was stirred for 2 hr at RT. After completion of the reaction, the reaction mixture was dilute with water and the product was extracted in DCM (2×20 ml). The organic layer was washed with water (2×15 ml), dried over anhydrous sodium sulfate, filtered and concentrated over the rotary evaporator to get the crude product. Crude product was purified by column chromatography (60-120 silica gel, 2% MeOH-DCM) to get pure product, Boc-63 (54%; not shown) as an off-white solid, which was subjected to the treatment with methanolic HCl (10 ml) for 2 hr at RT. After the complete cleavage of Boc-group, the solvent was removed under low pressure, to give the crude product as an HCl salt. The aqueous solution of the salt was washed with diethylether and basified with NaHCO$_3$ (pH 10). The desired product was then partitioned into ethyl acetate, dried over anhydrous Na$_2$SO$_4$ and the solvent removed under low pressure to get the free amine 63 as off white solid (88%).

General Procedure for the Synthesis of Compounds of Formula II Wherein $R^{1a}$ is Hydrogen and $R^{1b}$ is —O—C(O)—NH—$R^a$ EDCI (58 mg, 0.3048 mmol) and HOBT (41 mg, 0.3048 mmol) were added to a stirred solution of the acid 8 (100 mg, 0.3048 mmol; prepared as in Example 1) in anhydrous DMF. The temperature of the mixture was reduced to 0° C., at which time DIPEA (196 µl, 1.067 mmol) was added under nitrogen atmosphere and the resultant solution (or suspension) was stirred at room temperature for 30 min. Amine 63 (0.3048 mmol) was then added at 0° C. The reaction mixture was then brought to room temperature and stirred overnight. After completion of the reaction, the reaction mixture was diluted with water and extracted with ethyl acetate (3×15 ml). The organic layer was washed with water (3×10 ml), dried over anhydrous sodium sulfate, filtered and concentrated over the rotary evaporator to get the crude product. Crude product was purified by either by silica column chromatography or preparative HPLC to obtain the pure products in 53-78% yields.

Compound 132: 1-(3-Methyl-4-(quinoline-8-sulfonamido)benzoyl)azetidin-3-yl isopropylcarbamate

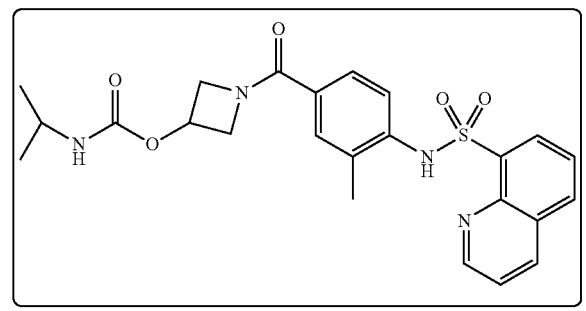 [SMILES: Cc1cc(C(=O)N2CC(OC(=O)NC(C)C)C2)ccc1NS(=O)(=O)c1cccc2cccnc12]

$^1$H NMR (400 MHz, CDCl$_3$) δ: 1.2 (s, 3H), 2.2 (d, 3H), 2.6 (d, 3H), 3.8 (m, 1H), 4.2 (d, 2H), 4.7 (d, 2H), 5.2 (m, 1H), 7.2-7.8 (m, 5H), 8.0-8.7 (m, 3H), 9.1 (m, 1H); HPLC Purity: 99.0%; LCMS, m/z found 483.1 (M+1)$^+$.

Compound 133: 1-(2-Methoxy-4-(quinoline-8-sulfonamido)benzoyl)azetidin-3-yl isopropylcarbamate

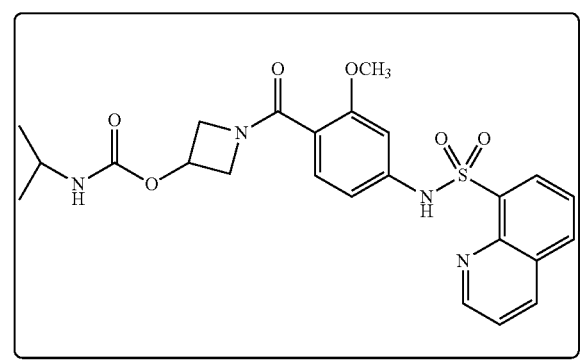 [SMILES: COc1cc(NS(=O)(=O)c2cccc3cccnc23)ccc1C(=O)N1CC(OC(=O)NC(C)C)C1]

$^1$H NMR (400 MHz, CDCl$_3$) δ: 1.6 (d, 6H), 3.9 (s, 3H), 4.2 (d, 2H), 4.7 (d, 2H), 5.2 (m, 1H), 6.3-7.0 (m, 3H), 7.6-8.4 (m, 5H), 9.1 (m, 1H); HPLC Purity: 99.7%; LCMS, m/z found 499.1 (M+1)$^+$.

Compound 134: 1-(3-Fluoro-4-(quinoline-8-sulfonamido)benzoyl)azetidin-3-yl isopropylcarbamate

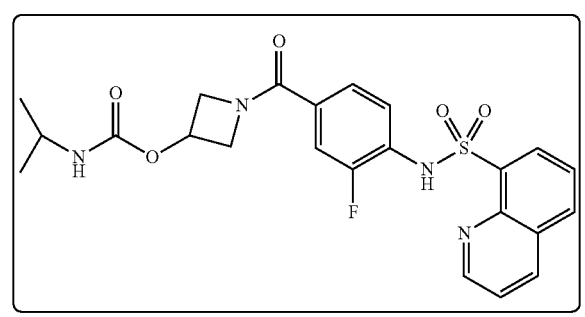 [SMILES: CC(C)NC(=O)OC1CN(C(=O)c2ccc(NS(=O)(=O)c3cccc4cccnc34)c(F)c2)C1]

$^1$H NMR (400 MHz, CDCl$_3$) δ: 1.4 (d, 6H), 3.7 (m, 1H), 3.8 (d, 2H), 4.2 (d, 2H), 5.2 (m, 1H), 7.0-7.6 (m, 5H), 8.0-8.4 (m, 3H), 9.1 (m, 1H); HPLC Purity: 98.6%; LCMS, m/z found 509 (M+Na)$^+$.

Compound 135: 1-(4-(Quinoline-8-sulfonamido)benzoyl)azetidin-3-yl isopropylcarbamate

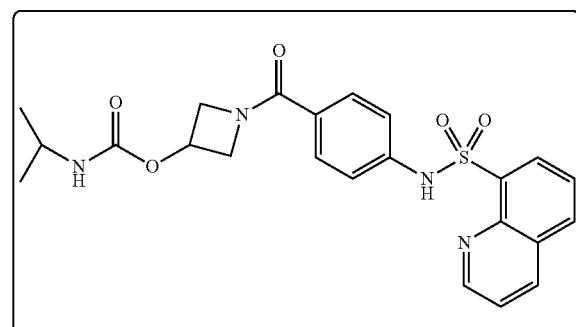

$^1$H NMR (400 MHz, CDCl$_3$) δ: 1.4 (d, 6H), 3.8 (m, 1H), 4.1 (d, 2H), 4.4 (d, 2H), 5.2 (m, 1H), 7.0-7.6 (m, 5H), 8.0-8.4 (m, 4H), 9.1 (m, 1H); HPLC Purity: 98.6%; LCMS, m/z found 469.2 (M+1)$^+$.

Compound 155: 1-(3-Methyl-4-(quinoline-8-sulfonamido)benzoyl)azetidin-3-yl pyridin-2-ylcarbamate

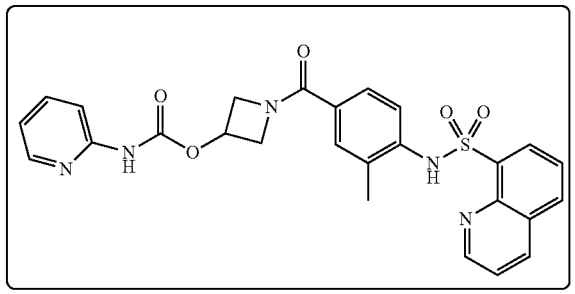 [SMILES: Cc1cc(C(=O)N2CC(OC(=O)Nc3ccccn3)C2)ccc1NS(=O)(=O)c1cccc2cccnc12]

$^1$H NMR (400 MHz, CDCl$_3$) δ: 2.1 (s, 3H), 3.8 (m, 1H), 4.1 (d, 2H), 4.4 (d, 2H), 5.2 (m, 1H), 7.0-7.6 (m, 7H), 8.0-8.4 (m, 5H), 9.1 (m, 1H); HPLC Purity: 96.1%; LCMS, m/z found 518.3 (M+1)$^+$.

Compound 156: 1-(3-Methoxy-4-(quinoline-8-sulfonamido)benzoyl)azetidin-3-yl pyridin-2-ylcarbamate (40f)

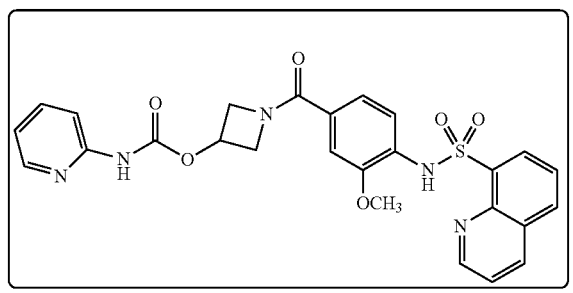 [SMILES: COc1cc(C(=O)N2CC(OC(=O)Nc3ccccn3)C2)ccc1NS(=O)(=O)c1cccc2cccnc12]

$^1$H NMR (400 MHz, CDCl$_3$) δ: 3.6 (s, 3H), 4.1 (d, 2H), 4.4 (d, 2H), 5.2 (m, 1H), 7.0-7.6 (m, 7H), 8.0-8.4 (m, 5H), 9.1 (m, 1H); HPLC Purity: 99.1%; LCMS, m/z found 534.3 (M+1)$^+$.

Compound 157: 1-(2-Methoxy-4-(quinoline-8-sulfonamido)benzoyl)azetidin-3-yl pyridin-2-ylcarbamate

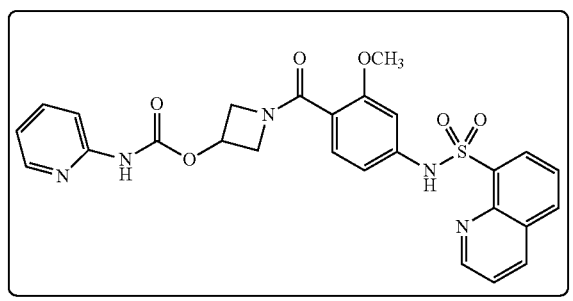 [SMILES: COc1cc(NS(=O)(=O)c2cccc3cccnc23)ccc1C(=O)N1CC(OC(=O)Nc2ccccn2)C1]

$^1$H NMR (400 MHz, CDCl$_3$) δ: 3.8 (s, 3H), 4.2 (d, 2H), 4.4 (d, 2H), 5.2 (m, 1H), 6.6-7.6 (m, 7H), 8.0-8.4 (m, 5H), 9.1 (m, 1H); HPLC Purity: 96.1%; LCMS, m/z found 534.3 (M+1)$^+$.

Compound 161: 1-(4-(Quinoline-8-sulfonamido)benzoyl)azetidin-3-ylpyridin-2-ylcarbamate

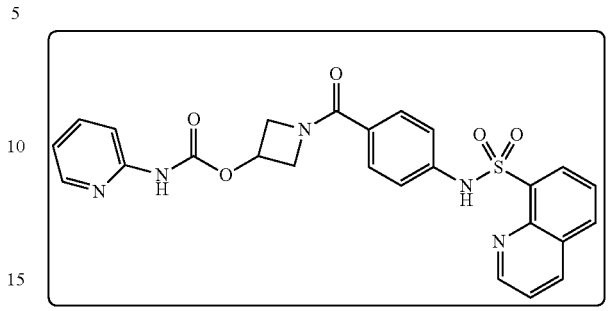

$^1$H NMR (400 MHz, CDCl$_3$) δ: 4.2 (d, 2H), 4.4 (d, 2H), 5.2 (m, 1H), 7.0-8.0 (m, 9H), 8.0-8.4 (m, 4H), 9.1 (m, 1H); HPLC Purity: 98.3%; LCMS, m/z found 504.3 (M+1)$^+$.

Compound 162: 1-(3-Fluoro-4-(quinoline-8-sulfonamido)benzoyl)azetidin-3-yl pyridin-2-ylcarbamate

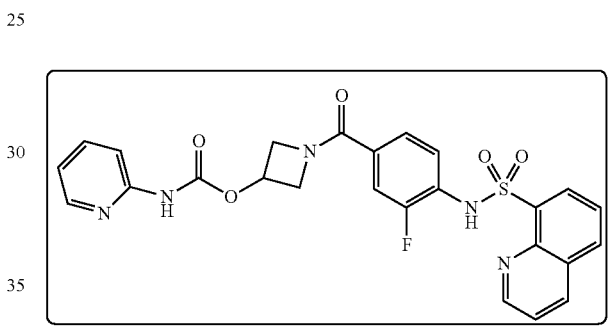

$^1$H NMR (400 MHz, CDCl$_3$) δ: 4.2 (d, 2H), 4.4 (d, 2H), 5.2 (m, 1H), 7.0-8.0 (m, 8H), 8.0-8.4 (m, 4H), 9.1 (m, 1H); HPLC Purity: 98.8%; LCMS, m/z found 522.3 (M+1)$^+$.

Example 8

PKM2 Assay

Procedure:
PKM2 stock enzyme solution was diluted in Reaction Buffer
2 µL of compound was added into each well first, and then 180 µL of the Reaction Mix was added.
Reaction mixture with compound (without ADP) were incubated for 30 minutes at 4° C.
Plates were re-equilibrated to room temperature prior to adding 20 µL ADP to initiate the reaction.
Reaction progress was measured as changes in absorbance at 340 nm wavelength at room temperature (25° C.)
Reaction Mix: PKM2 (50 ng/well), ADP (0.7 mM), PEP (0.15 mM), NADH (180 µM), LDH (2 units) in Reaction Buffer
Reaction Buffer: 100 mM KCl, 50 mM Tris pH 7.5, 5 mM MgCl2, 1 mM DTT, 0.03% BSA.

Certain compounds of Formula I were tested in the above-described assay. The results are shown in Table 2, below. A compound described herein may be tested for its ability to activate PKM2. The activation activity of these compounds is represented as an AC$_{50}$ in Table 2 and throughout the application. As shown in Table 2, "A" refers to an activator of PKM2 with an $EC_{50}$<100 nM. "B" refers to an activator of PKM2 with an $EC_{50}$ between 100 nM and 1 µM. "C" refers to an activator of PKM2 with an $EC_{50}$ between 1 µM and 10 µM. "D" refers to an activator of PKM2 with an $EC_{50}$ greater than 10 µM. "NA" refers to data that is not available.

TABLE 2

$AC_{50}$ Values for Exemplary Compounds of Formula I

| Compound | $AC_{50}$ |
|---|---|
| 100 | B |
| 101 | A |
| 102 | C |
| 103 | B |
| 104 | D |
| 105 | B |
| 106 | A |
| 107 | B |
| 108 | B |
| 109 | B |
| 110 | B |
| 111 | C |
| 112 | A |
| 113 | A |
| 114 | A |
| 115 | B |
| 116 | D |
| 117 | B |
| 118 | B |
| 119 | C |
| 120 | B |
| 121 | C |
| 122 | A |
| 123 | B |
| 124 | C |
| 125 | D |
| 126 | D |
| 127 | C |
| 128 | D |
| 129 | B |
| 130 | A |
| 131 | A |
| 132 | B |
| 133 | B |
| 134 | C |
| 135 | C |
| 136 | B |
| 137 | B |
| 138 | A |
| 139 | C |
| 140 | C |
| 141 | D |
| 142 | C |
| 143 | D |
| 144 | C |
| 145 | A |
| 146 | B |
| 147 | B |
| 148 | B |
| 149 | A |
| 150 | A |
| 151 | A |
| 152 | NA |
| 153 | B |
| 154 | B |
| 155 | B |
| 156 | B |
| 157 | B |
| 158 | A |
| 159 | A |
| 160 | B |
| 161 | C |
| 162 | D |
| 163 | C |
| 164 | B |
| 165 | B |
| 166 | NA |

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A compound of formula (I):

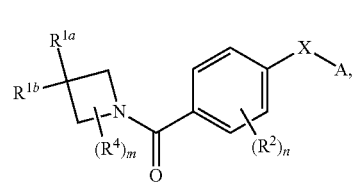

or a pharmaceutically acceptable salt thereof, wherein:

A is bicyclic heteroaryl;

X is selected from $-NH-S(O)_2-$ and $-S(O)_2-N(H)-$;

$R^{1a}$ is selected from hydrogen, alkyl, and arylalkyl; and $R^{1b}$ is selected from $OR^3$, $N(alkyl)R^3$ and $NHR^3$; or $R^{1a}$ is alken-1-yl and $R^{1b}$ is absent;

each $R^2$ is independently selected from halo, haloalkyl, alkyl, alkoxy and hydroxyl;

$R^3$ is selected from hydrogen, alkyl, optionally substituted aryl, optionally substituted heteroaryl, arylalkyl, $C(O)R^a$, and $C(O)N(H)R^a$, wherein $R^a$ is selected from alkyl, alkenyl, aryl, heteroaryl, arylalkyl and heteroarylalkyl; and wherein any aryl or heteroaryl portion of $R^a$ is optionally substituted;

each $R^4$ is independently selected from haloalkyl, alkyl, alkoxy and hydroxyl n is 0, 1, or 2; and m is 0, 1, or 2.

2. The compound of claim 1, wherein m is 0, the compound having Formula (Ia):

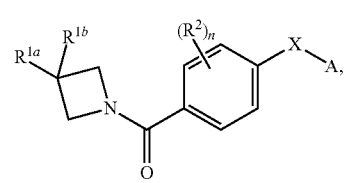

or a pharmaceutically acceptable salt thereof.

3. The compound of claim 1, wherein A is quinolin-8-yl, wherein the compound is a compound of Formula II:

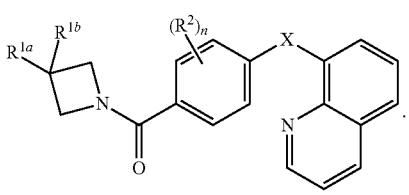
(II)

4. The compound of claim 1, wherein $R^{1a}$ is selected from hydrogen, optionally substituted phenyl, methyl and optionally substituted benzyl.

5. The compound of claim 1, wherein $R^{1b}$ is selected from hydroxyl, methoxy, optionally substituted benzoxy, optionally substituted —OC(O)-benzyl, optionally substituted —OC(O)-pyridinyl, —OC(O)NH(CH(CH$_3$)$_2$), optionally substituted —OC(O)NH(pyridinyl), —NH(optionally substituted phenyl), —N(CH$_3$)(optionally substituted phenyl), —NH(optionally substituted benzyl), —NH(optionally substituted pyridinyl), —NH(C(O)-pyridinyl), —NH(C(O)—NH—CH(CH$_3$)$_2$), and —NH(C(O)—NH—CH$_2$—CH=CH$_2$).

6. The compound of claim 1, wherein n is 0 or 1, provided that when n is 1, $R^2$ is selected from fluoro, methyl, and methoxy.

7. The compound of claim 3, wherein:
X is —NH—S(O)$_2$—;
$R^{1a}$ is phenyl or benzyl, wherein the ring portion of $R^{1a}$ is optionally substituted;
$R^{1b}$ is hydroxyl; and
n is 0 or 1.

8. The compound of claim 3, wherein:
X is —NH—S(O)$_2$—;
$R^{1a}$ is hydrogen;
$R^{1b}$ is selected from —NH-phenyl, phenoxy, —NH-pyridin-2-yl, and —N(CH$_3$)-phenyl, wherein the phenyl or pyridinyl portion of $R^{1b}$ is optionally substituted; and
n is 0 or 1.

9. The compound of claim 1, wherein n is 1 and $R^2$ selected from methyl and methoxy.

10. The compound of claim 1, selected from any one of the compounds in the table below:

| Compound | Structure |
|---|---|
| 100 | 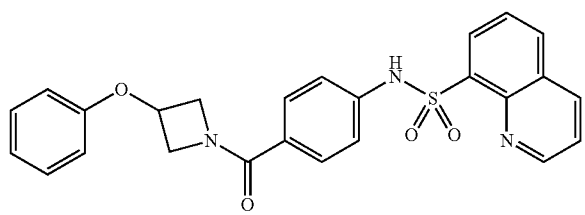 [SMILES: O=C(c1ccc(NS(=O)(=O)c2cccc3cccnc23)cc1)N1CC(Oc2ccccc2)C1] |
| 101 | 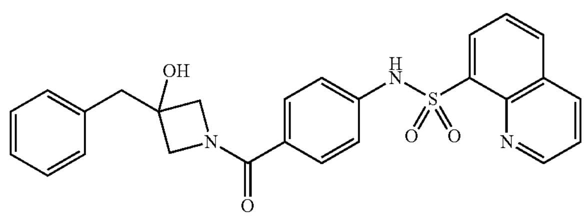 [SMILES: O=C(c1ccc(NS(=O)(=O)c2cccc3cccnc23)cc1)N1CC(O)(Cc2ccccc2)C1] |
| 102 | 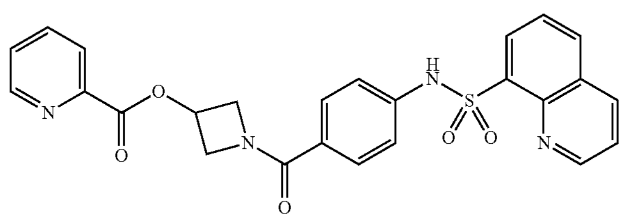 [SMILES: O=C(OC1CN(C(=O)c2ccc(NS(=O)(=O)c3cccc4cccnc34)cc2)C1)c1ccccn1] |
| 103 | 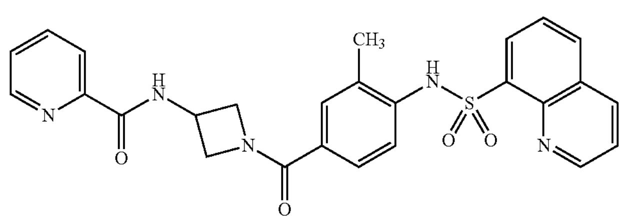 [SMILES: Cc1cc(C(=O)N2CC(NC(=O)c3ccccn3)C2)ccc1NS(=O)(=O)c1cccc2cccnc12] |

| Compound | Structure |
|---|---|
| 104 | 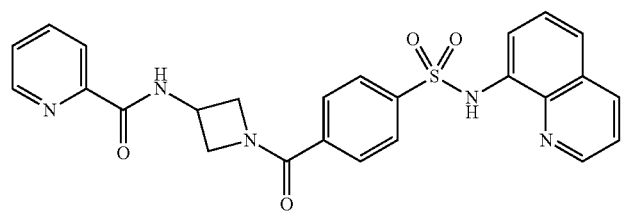 [SMILES: O=C(NC1CN(C(=O)c2ccc(S(=O)(=O)Nc3cccc4cccnc34)cc2)C1)c1ccccn1] |
| 105 | 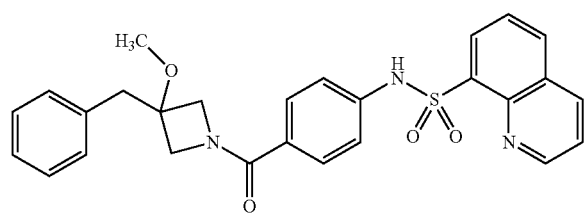 [SMILES: COC1(Cc2ccccc2)CN(C(=O)c2ccc(NS(=O)(=O)c3cccc4cccnc34)cc2)C1] |
| 106 | 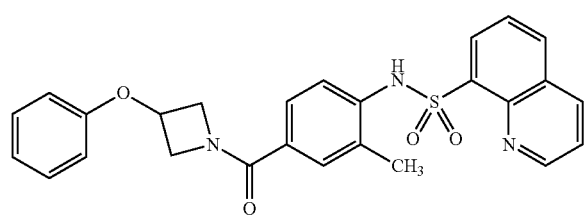 [SMILES: Cc1cc(C(=O)N2CC(Oc3ccccc3)C2)ccc1NS(=O)(=O)c1cccc2cccnc12] |
| 107 | 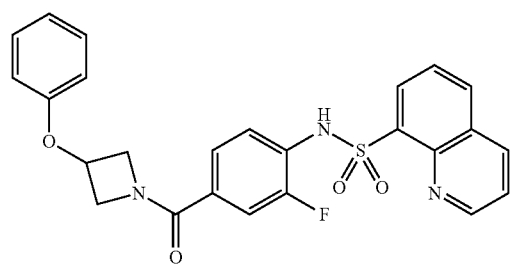 [SMILES: O=C(c1ccc(NS(=O)(=O)c2cccc3cccnc23)c(F)c1)N1CC(Oc2ccccc2)C1] |
| 108 | 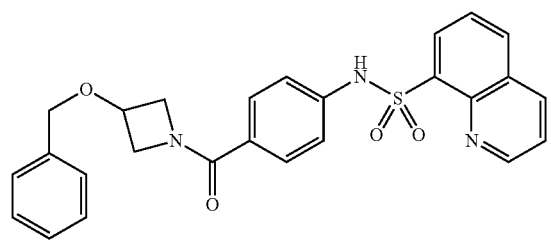 [SMILES: O=C(c1ccc(NS(=O)(=O)c2cccc3cccnc23)cc1)N1CC(OCc2ccccc2)C1] |
| 109 | 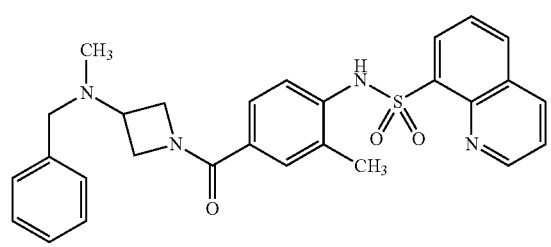 [SMILES: Cc1cc(C(=O)N2CC(N(C)Cc3ccccc3)C2)ccc1NS(=O)(=O)c1cccc2cccnc12] |

| Compound | Structure |
|---|---|
| 110 | 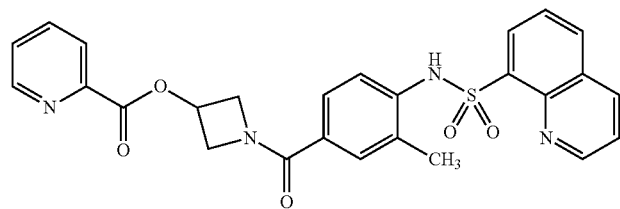 [SMILES: Cc1cc(C(=O)N2CC(OC(=O)c3ccccn3)C2)ccc1NS(=O)(=O)c1cccc2cccnc12] |
| 111 | 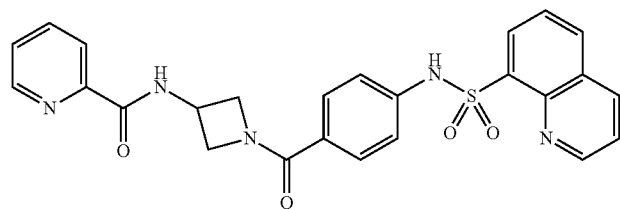 [SMILES: O=C(NC1CN(C(=O)c2ccc(NS(=O)(=O)c3cccc4cccnc34)cc2)C1)c1ccccn1] |
| 112 | 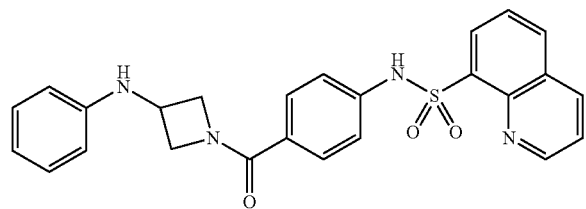 [SMILES: O=C(c1ccc(NS(=O)(=O)c2cccc3cccnc23)cc1)N1CC(Nc2ccccc2)C1] |
| 113 | 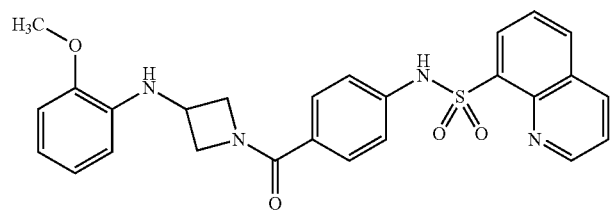 [SMILES: COc1ccccc1NC1CN(C(=O)c2ccc(NS(=O)(=O)c3cccc4cccnc34)cc2)C1] |
| 114 | 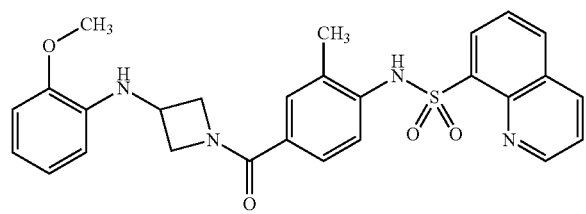 [SMILES: COc1ccccc1NC1CN(C(=O)c2ccc(NS(=O)(=O)c3cccc4cccnc34)c(C)c2)C1] |
| 115 | 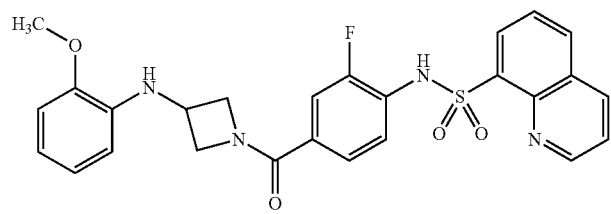 [SMILES: COc1ccccc1NC1CN(C(=O)c2ccc(NS(=O)(=O)c3cccc4cccnc34)c(F)c2)C1] |
| 116 | 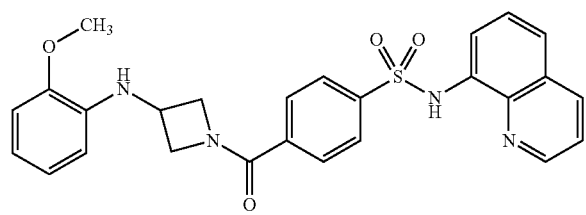 [SMILES: COc1ccccc1NC1CN(C(=O)c2ccc(S(=O)(=O)Nc3cccc4cccnc34)cc2)C1] |

-continued
| Compound | Structure |
|---|---|
| 117 | 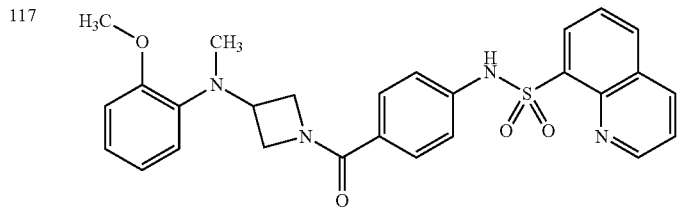 |
| 118 | 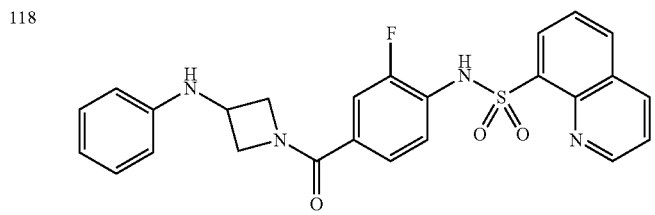 |
| 119 | 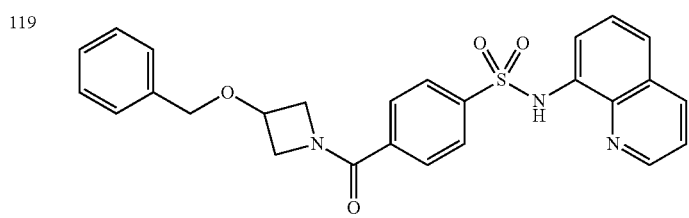 |
| 120 | 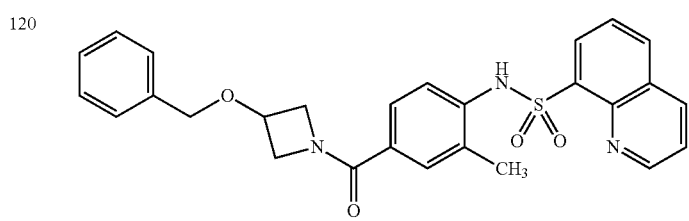 |
| 121 | 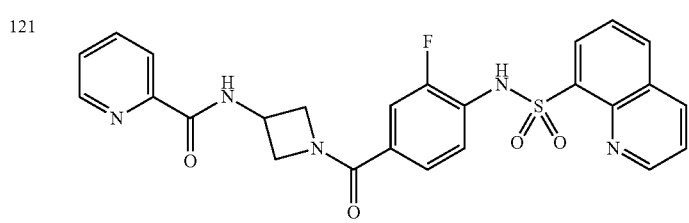 |
| 122 | 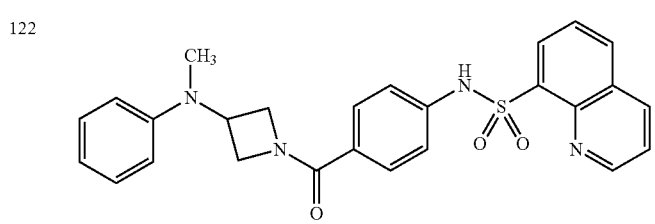 |
| 123 | 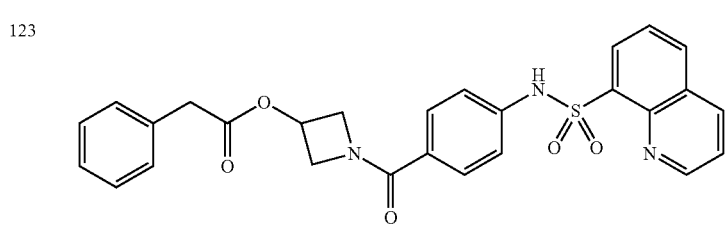 |

| Compound | Structure |
|---|---|
| 124 | 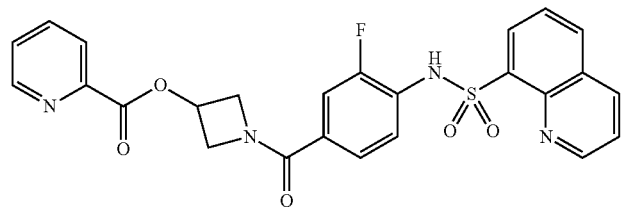 [SMILES: O=C(OC1CN(C(=O)c2ccc(NS(=O)(=O)c3cccc4cccnc34)c(F)c2)C1)c1ccccn1] |
| 125 | 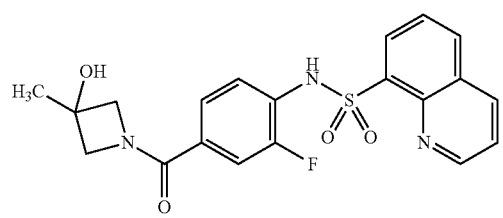 [SMILES: CC1(O)CN(C(=O)c2ccc(NS(=O)(=O)c3cccc4cccnc34)c(F)c2)C1] |
| 126 | 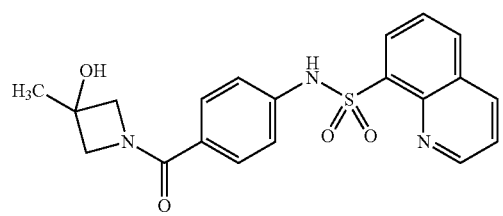 [SMILES: CC1(O)CN(C(=O)c2ccc(NS(=O)(=O)c3cccc4cccnc34)cc2)C1] |
| 127 | 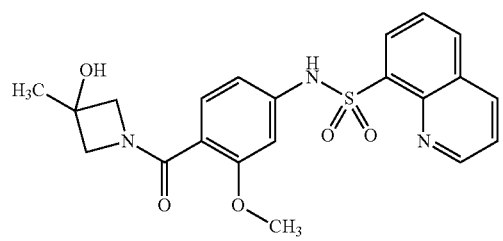 [SMILES: COc1cc(NS(=O)(=O)c2cccc3cccnc23)ccc1C(=O)N1CC(C)(O)C1] |
| 128 | 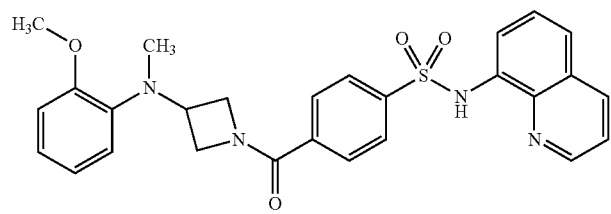 [SMILES: COc1ccccc1N(C)C1CN(C(=O)c2ccc(S(=O)(=O)Nc3cccc4cccnc34)cc2)C1] |
| 129 | 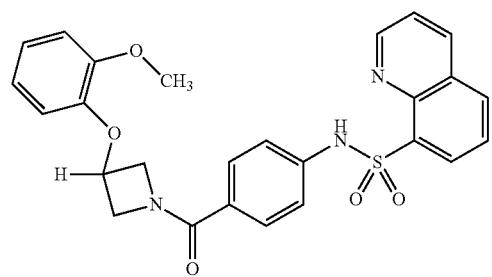 [SMILES: COc1ccccc1OC1CN(C(=O)c2ccc(NS(=O)(=O)c3cccc4cccnc34)cc2)C1] |

| Compound | Structure |
|---|---|
| 130 | 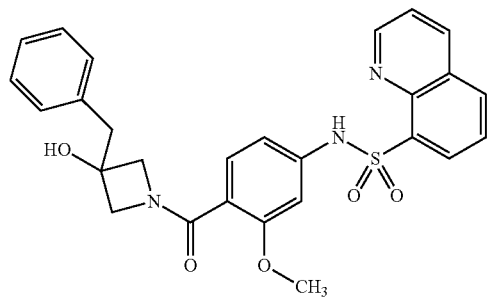 [SMILES: COc1cc(NS(=O)(=O)c2cccc3cccnc23)ccc1C(=O)N1CC(O)(Cc2ccccc2)C1] |
| 131 | 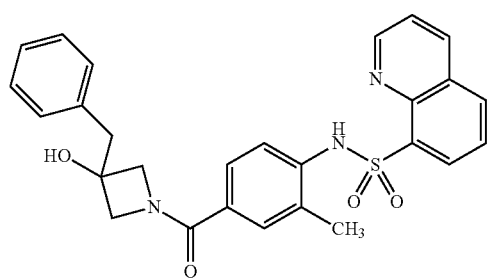 [SMILES: Cc1cc(C(=O)N2CC(O)(Cc3ccccc3)C2)ccc1NS(=O)(=O)c1cccc2cccnc12] |
| 132 | 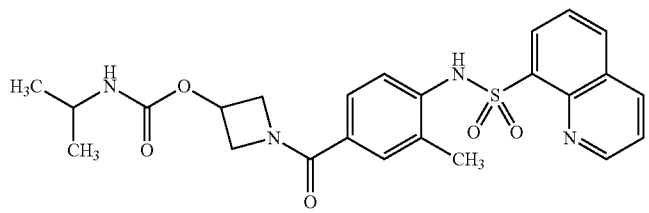 [SMILES: Cc1cc(C(=O)N2CC(OC(=O)NC(C)C)C2)ccc1NS(=O)(=O)c1cccc2cccnc12] |
| 133 | 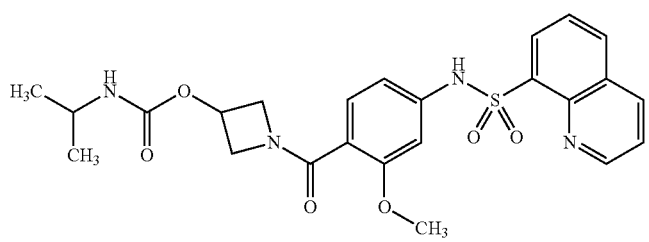 [SMILES: COc1cc(NS(=O)(=O)c2cccc3cccnc23)ccc1C(=O)N1CC(OC(=O)NC(C)C)C1] |
| 134 | 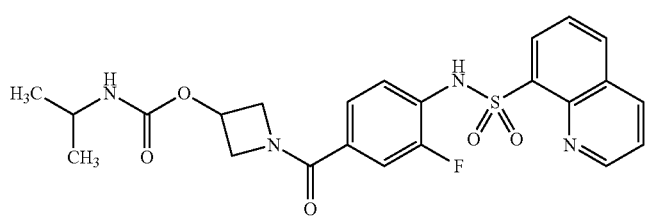 [SMILES: CC(C)NC(=O)OC1CN(C(=O)c2ccc(NS(=O)(=O)c3cccc4cccnc34)c(F)c2)C1] |
| 135 | 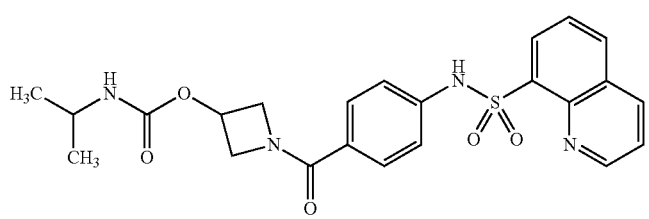 [SMILES: CC(C)NC(=O)OC1CN(C(=O)c2ccc(NS(=O)(=O)c3cccc4cccnc34)cc2)C1] |

| Compound | Structure |
|---|---|
| 136 | 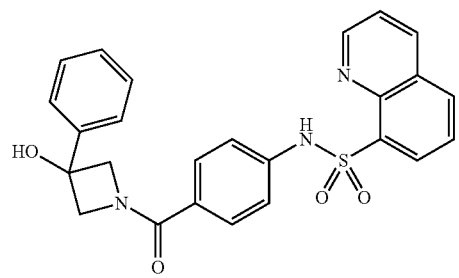 [SMILES: O=C(c1ccc(NS(=O)(=O)c2cccc3cccnc23)cc1)N1CC(O)(c2ccccc2)C1] |
| 137 | 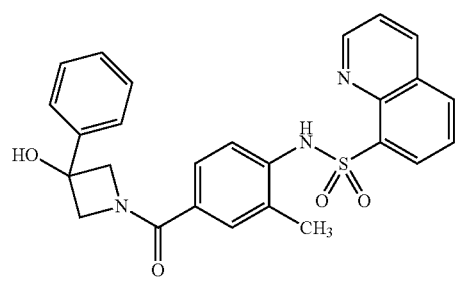 [SMILES: Cc1cc(C(=O)N2CC(O)(c3ccccc3)C2)ccc1NS(=O)(=O)c1cccc2cccnc12] |
| 138 | 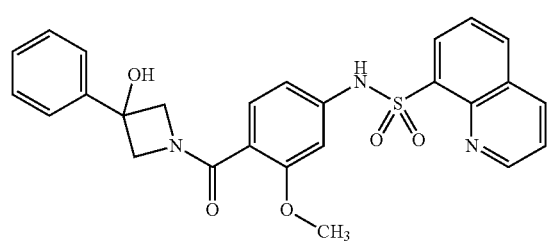 [SMILES: COc1cc(NS(=O)(=O)c2cccc3cccnc23)ccc1C(=O)N1CC(O)(c2ccccc2)C1] |
| 139 | 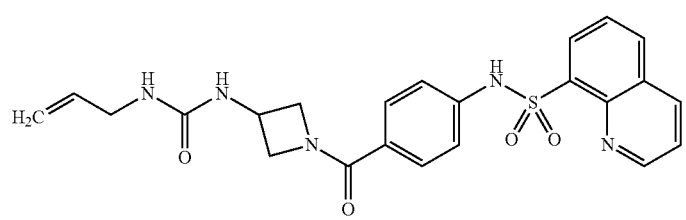 [SMILES: C=CCNC(=O)NC1CN(C(=O)c2ccc(NS(=O)(=O)c3cccc4cccnc34)cc2)C1] |
| 140 | 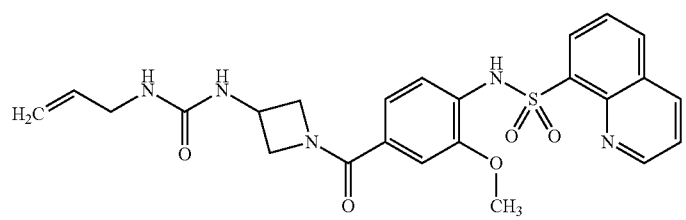 [SMILES: C=CCNC(=O)NC1CN(C(=O)c2ccc(NS(=O)(=O)c3cccc4cccnc34)c(OC)c2)C1] |
| 141 | 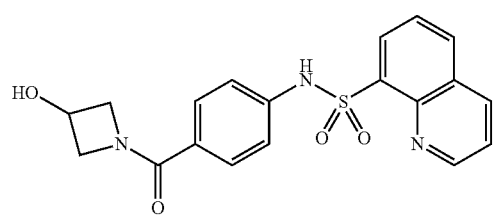 [SMILES: O=C(c1ccc(NS(=O)(=O)c2cccc3cccnc23)cc1)N1CC(O)C1] |

-continued
| Compound | Structure |
|---|---|
| 142 | 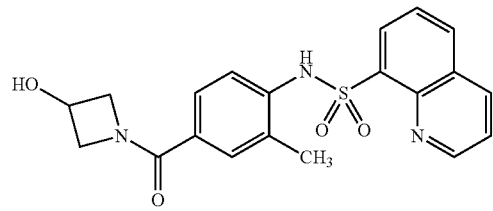 [SMILES: Cc1cc(C(=O)N2CC(O)C2)ccc1NS(=O)(=O)c1cccc2cccnc12] |
| 143 | 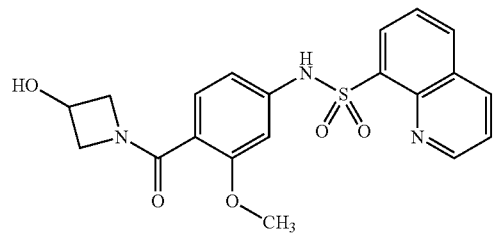 [SMILES: COc1cc(NS(=O)(=O)c2cccc3cccnc23)ccc1C(=O)N1CC(O)C1] |
| 144 | 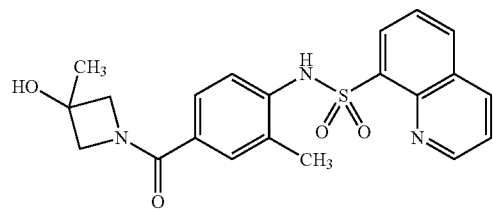 [SMILES: Cc1cc(C(=O)N2CC(C)(O)C2)ccc1NS(=O)(=O)c1cccc2cccnc12] |
| 145 | 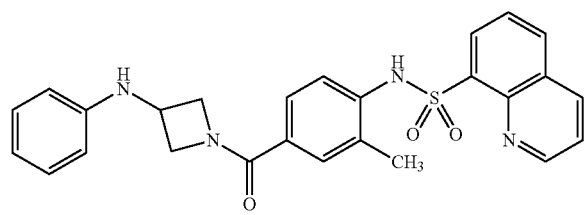 [SMILES: Cc1cc(C(=O)N2CC(Nc3ccccc3)C2)ccc1NS(=O)(=O)c1cccc2cccnc12] |
| 146 | 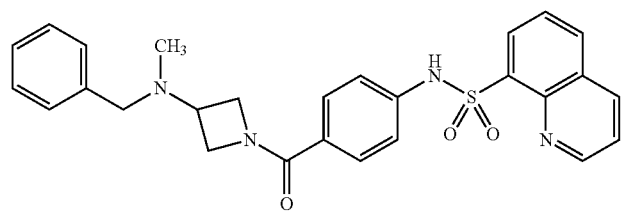 [SMILES: CN(Cc1ccccc1)C1CN(C(=O)c2ccc(NS(=O)(=O)c3cccc4cccnc34)cc2)C1] |
| 147 | 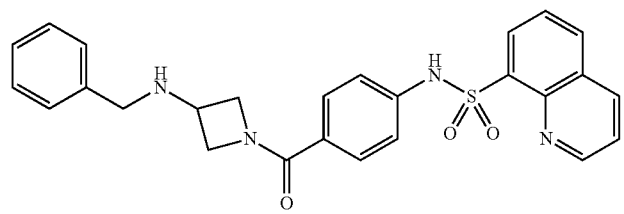 [SMILES: O=C(c1ccc(NS(=O)(=O)c2cccc3cccnc23)cc1)N1CC(NCc2ccccc2)C1] |
| 148 | 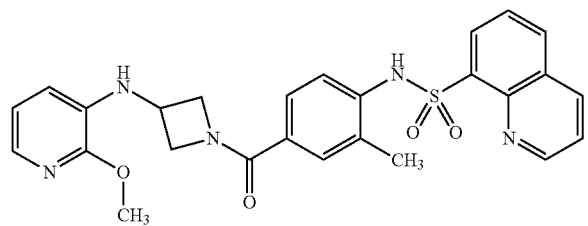 [SMILES: COc1ncccc1NC1CN(C(=O)c2ccc(NS(=O)(=O)c3cccc4cccnc34)c(C)c2)C1] |

| Compound | Structure |
|---|---|
| 149 | 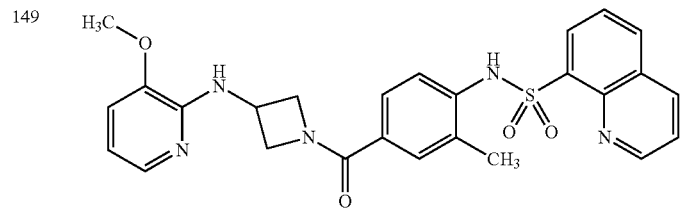 |
| 150 | 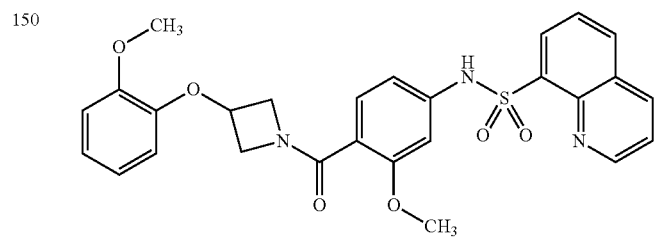 |
| 151 | 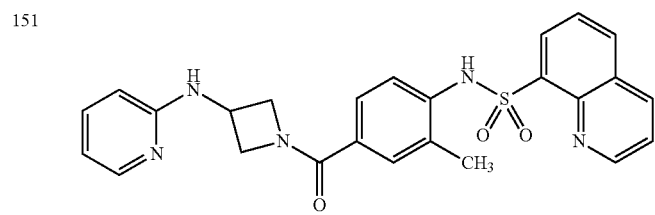 |
| 152 | 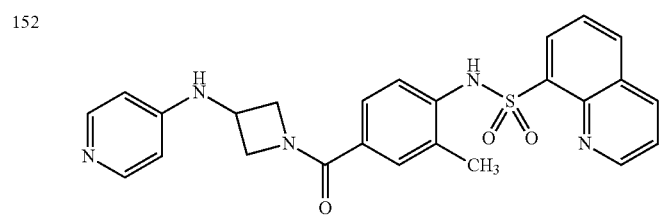 |
| 153 | 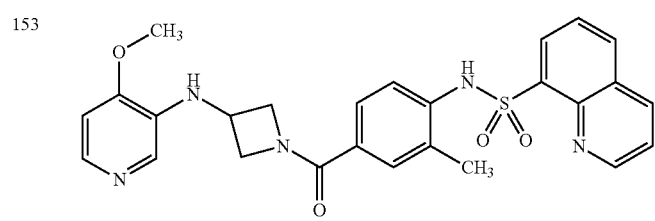 |
| 154 | 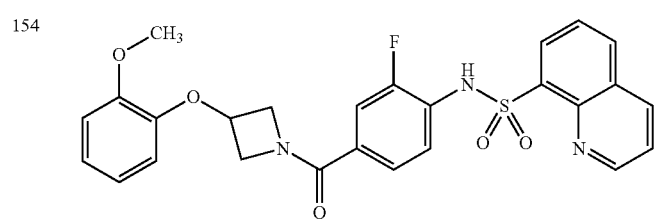 |
| 155 | 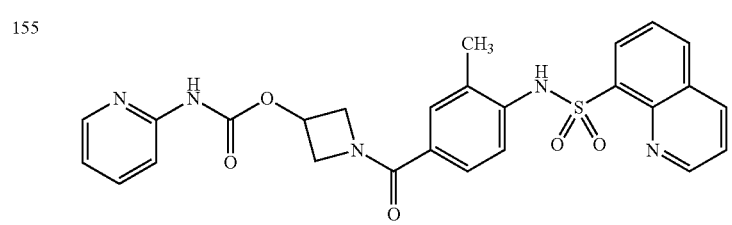 |

-continued
| Compound | Structure |
|---|---|
| 156 | 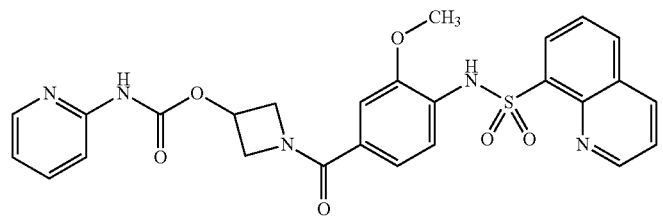 [SMILES: COc1cc(C(=O)N2CC(OC(=O)Nc3ccccn3)C2)ccc1NS(=O)(=O)c1cccc2cccnc12] |
| 157 | 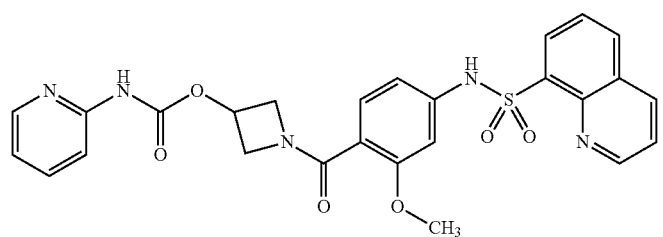 [SMILES: COc1cc(NS(=O)(=O)c2cccc3cccnc23)ccc1C(=O)N1CC(OC(=O)Nc2ccccn2)C1] |
| 158 | 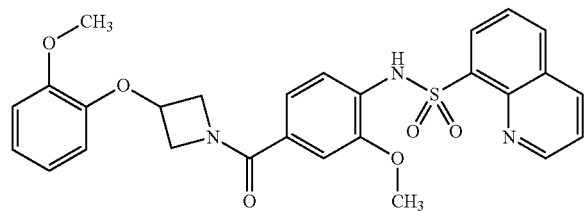 [SMILES: COc1cc(C(=O)N2CC(Oc3ccccc3OC)C2)ccc1NS(=O)(=O)c1cccc2cccnc12] |
| 159 | 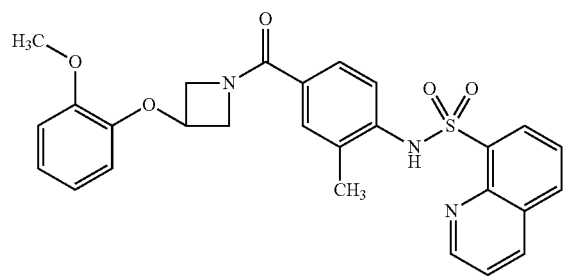 [SMILES: COc1ccccc1OC1CN(C(=O)c2ccc(NS(=O)(=O)c3cccc4cccnc34)c(C)c2)C1] |
| 160 | 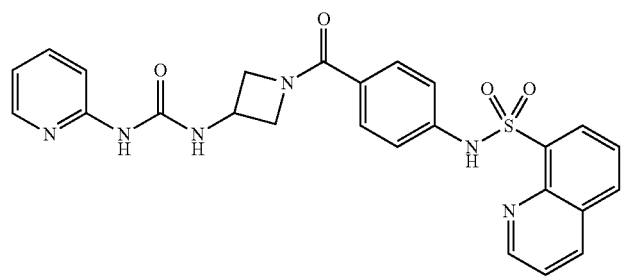 [SMILES: O=C(Nc1ccccn1)NC1CN(C(=O)c2ccc(NS(=O)(=O)c3cccc4cccnc34)cc2)C1] |
| 161 | 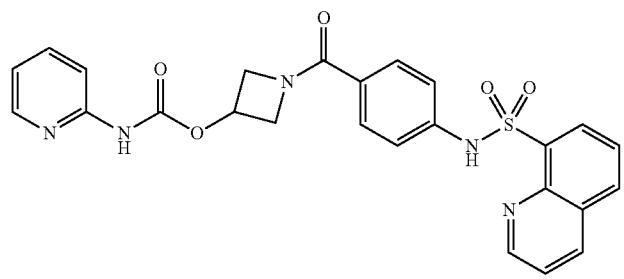 [SMILES: O=C(Nc1ccccn1)OC1CN(C(=O)c2ccc(NS(=O)(=O)c3cccc4cccnc34)cc2)C1] |

-continued
| Compound | Structure |
|---|---|
| 162 | 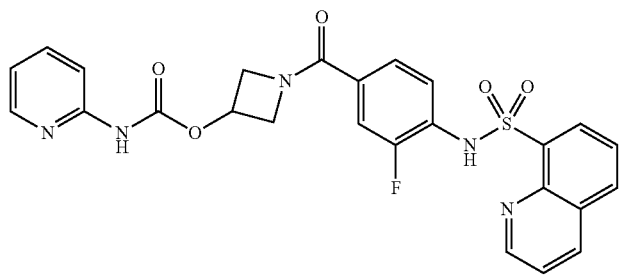 [SMILES: O=C(Nc1ccccn1)OC1CN(C(=O)c2ccc(NS(=O)(=O)c3cccc4cccnc34)c(F)c2)C1] |
| 163 | 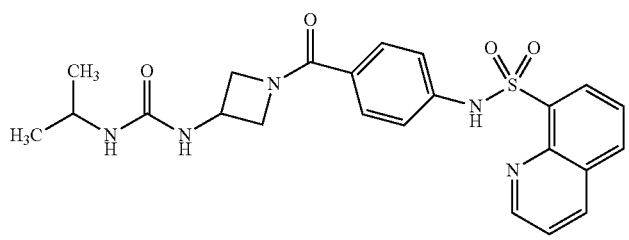 [SMILES: CC(C)NC(=O)NC1CN(C(=O)c2ccc(NS(=O)(=O)c3cccc4cccnc34)cc2)C1] |
| 164 | 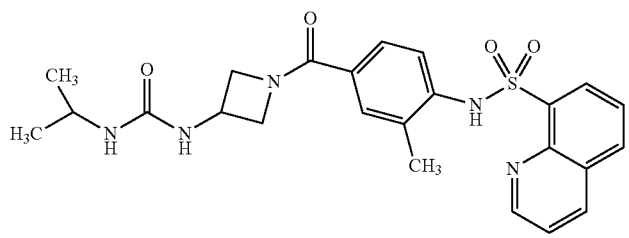 [SMILES: Cc1cc(C(=O)N2CC(NC(=O)NC(C)C)C2)ccc1NS(=O)(=O)c1cccc2cccnc12] |
| 165 | 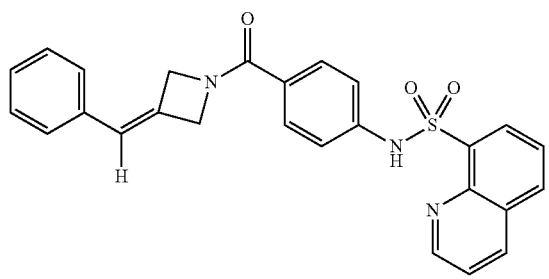 [SMILES: O=C(c1ccc(NS(=O)(=O)c2cccc3cccnc23)cc1)N1CC(=Cc2ccccc2)C1] |
| 166 | 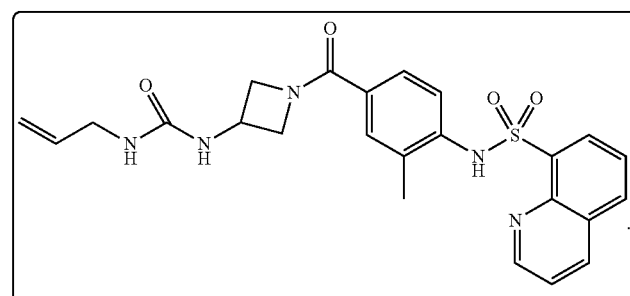 |

11. The compound of claim 10, selected from
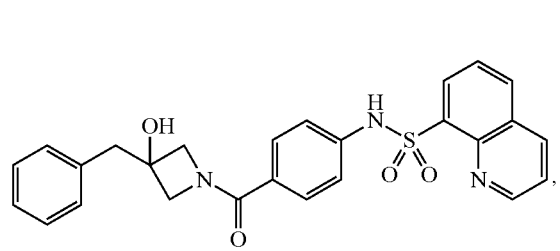
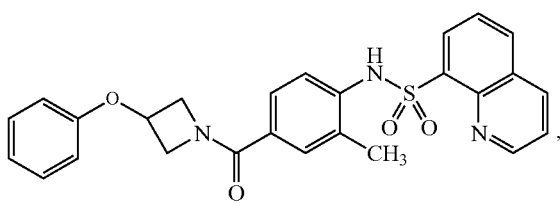
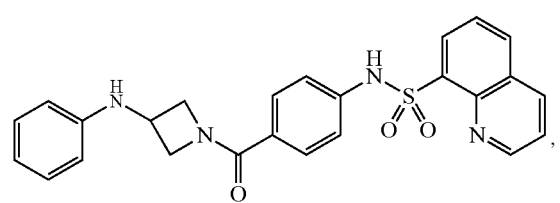
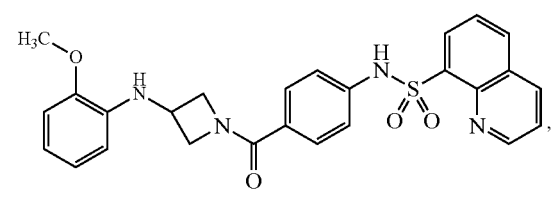
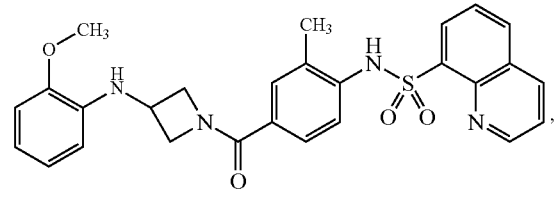
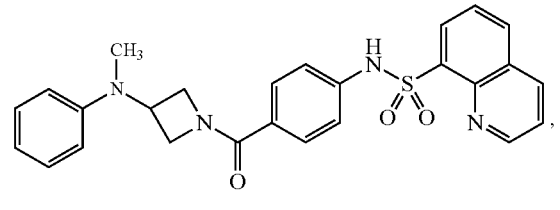
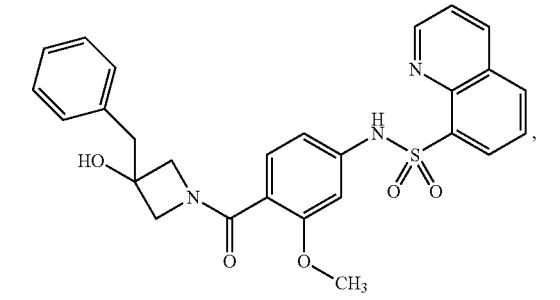
-continued
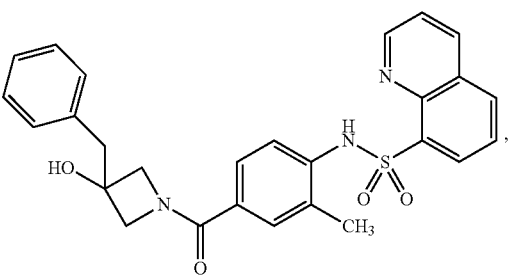
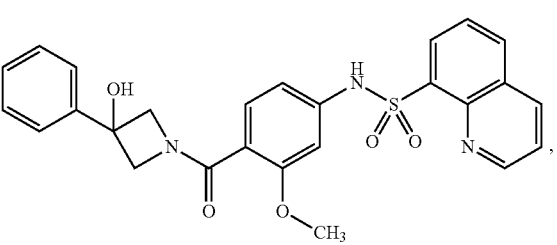
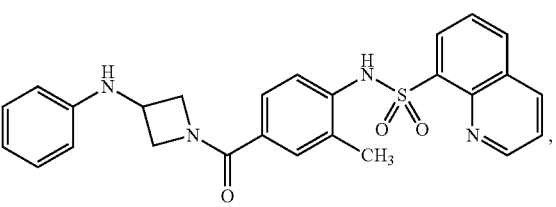
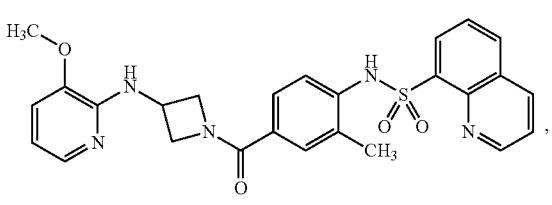
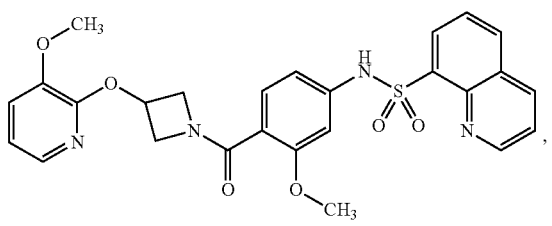
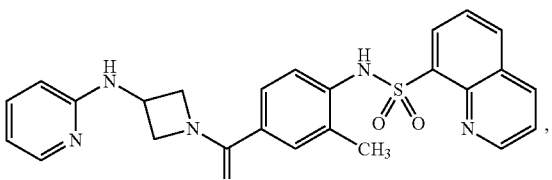
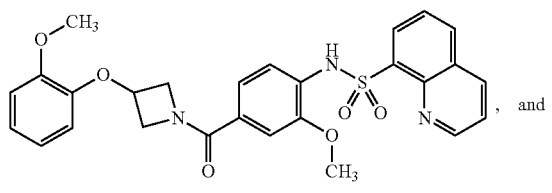, and -continued 12. A pharmaceutical composition comprising a compound of claim 1 or a pharmaceutically acceptable salt thereof and a pharmaceutically acceptable carrier.

13. A method of modulating PKM2 activity in a subject in need thereof, the method comprising administering to said subject a pharmaceutical composition of claim 12.

14. A method of treating a cancer associated with PKM2 activity in a subject in need thereof, the method comprising administering to the subject a pharmaceutical composition of claim 12.

* * * * *